US012649731B2

(12) United States Patent
Saito et al.

(10) Patent No.: US 12,649,731 B2
(45) Date of Patent: Jun. 9, 2026

(54) ELECTROLUMINESCENT ELEMENT, ORGANIC ELECTROLUMINESCENT ELEMENT, AND ELECTRONIC APPLIANCE

(71) Applicant: IDEMITSU KOSAN CO., LTD., Chiyoda-ku (JP)

(72) Inventors: Masatoshi Saito, Sodegaura (JP); Kei Yoshida, Sodegaura (JP); Yoshinori Aoyama, Sodegaura (JP); Masato Mitani, Sodegaura (JP); Sayaka Mizutani, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 544 days.

(21) Appl. No.: 18/260,403

(22) PCT Filed: Dec. 22, 2021

(86) PCT No.: PCT/JP2021/047690
§ 371 (c)(1),
(2) Date: Jul. 5, 2023

(87) PCT Pub. No.: WO2022/149476
PCT Pub. Date: Jul. 14, 2022

(65) Prior Publication Data

US 2024/0301281 A1 Sep. 12, 2024

(30) Foreign Application Priority Data

Jan. 8, 2021 (JP) ................................ 2021-002221

(51) Int. Cl.
*C07D 409/14* (2006.01)
*C09K 11/06* (2006.01)
(Continued)

(52) U.S. Cl.
CPC ............ *C07D 409/14* (2013.01); *C09K 11/06* (2013.01); *H10K 50/11* (2023.02); *H10K 50/166* (2023.02);
(Continued)

(58) Field of Classification Search
CPC .... C07D 409/14; H10K 50/166; H10K 50/11; H10K 85/6572; C09K 11/06; C09K 2211/1466
(Continued)

(56) References Cited

U.S. PATENT DOCUMENTS

| | | | |
|---|---|---|---|
| 7,651,791 B2 | 1/2010 | Nakano et al. |
| 2014/0001456 A1 | 1/2014 | Mizutani et al. |

(Continued)

FOREIGN PATENT DOCUMENTS

| | | |
|---|---|---|
| EP | 3 842 428 A1 | 6/2021 |
| KR | 10-2017-0089599 A | 8/2017 |

(Continued)

OTHER PUBLICATIONS

WO-2020045822-A1 English translation (Year: 2020).*
(Continued)

*Primary Examiner* — Anita Nassiri-Motlagh
(74) *Attorney, Agent, or Firm* — Oblon, McClelland, Maier & Neustadt, L.L.P.

(57) ABSTRACT

A compound represented by the following formula (1):

(1)

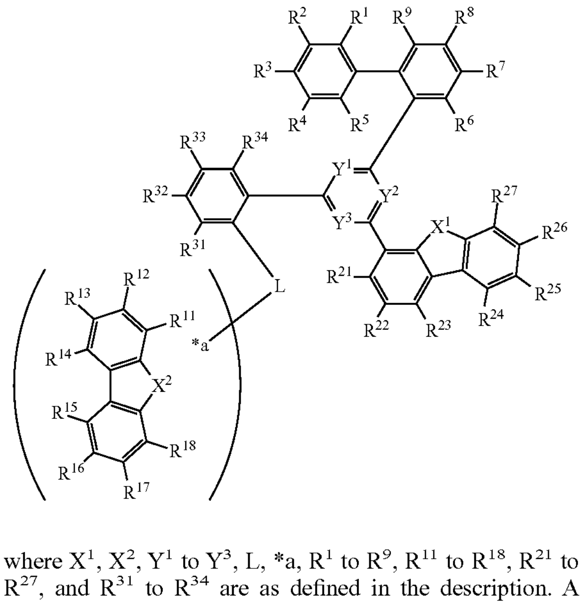

where $X^1$, $X^2$, $Y^1$ to $Y^3$, L, *a, $R^1$ to $R^9$, $R^{11}$ to $R^{18}$, $R^{21}$ to $R^{27}$, and $R^{31}$ to $R^{34}$ are as defined in the description. A
(Continued)

material for an organic electroluminescent device, the material including the compound of formula (1).

19 Claims, 1 Drawing Sheet

(51) Int. Cl.

| | |
|---|---|
| ***H10K 50/11*** | (2023.01) |
| ***H10K 50/16*** | (2023.01) |
| ***H10K 85/60*** | (2023.01) |

(52) U.S. Cl.
CPC .. *H10K 85/6572* (2023.02); *C09K 2211/1466* (2013.01)

(58) Field of Classification Search
USPC .................................................... 252/301.16
See application file for complete search history.

(56) References Cited

U.S. PATENT DOCUMENTS

| | | | |
|---|---|---|---|
| 2014/0312338 | A1 | 10/2014 | Mizutani et al. |
| 2018/0337348 | A1 | 11/2018 | Jung et al. |
| 2021/0163452 | A1 | 6/2021 | Yoo et al. |
| 2023/0047894 | A1 | 2/2023 | Shirasaki et al. |

FOREIGN PATENT DOCUMENTS

| | | | |
|---|---|---|---|
| KR | 10-2018-0063710 | A | 6/2018 |
| KR | 10-2019-0006353 | A | 1/2019 |
| KR | 10-2020-0145214 | A | 12/2020 |
| WO | WO 2013/077352 | A1 | 5/2013 |
| WO | WO 2013/077362 | A1 | 5/2013 |
| WO | WO 2018/016742 | A1 | 1/2018 |
| WO | WO 2019/112214 | A1 | 6/2019 |
| WO | WO-2020/045822 | A1 | 3/2020 |
| WO | WO 2020/111586 | A1 | 6/2020 |
| WO | WO 2020/116615 | A1 | 6/2020 |

OTHER PUBLICATIONS

KR-20200145214-A English translation (Year: 2020).*

Extended European Search Report issued Dec. 12, 2024 in European Patent Application No. 21917696.3, 9 pages.

Combined Chinese Office Action and Search Report issued Nov. 1, 2025 in Chinese Patent Application No. 202180089246.9 (with unedited computer-generated English translation), 23 pages.

European Office Action issued Jan. 21, 2026 in European Patent Application No. 21 917 696.3, 4 pgs.

Office Action issued Aug. 29, 2023, in corresponding Japanese Patent Application No. 2022-573997 (with English Translation), 3 pages.

International Search Report and Written Opinion issued Feb. 15, 2022, in PCT/JP2021/047690 (with English Translation), 11 pages.

* cited by examiner

ELECTROLUMINESCENT ELEMENT, ORGANIC ELECTROLUMINESCENT ELEMENT, AND ELECTRONIC APPLIANCE

CROSS REFERENCE TO RELATED APPLICATIONS

This application is a National Stage entry under 35 U.S.C. § 371 of PCT/JP2021/047690, filed on Dec. 22, 2021, and claims priority to Japanese Patent Application No. 2021-002221, filed on Jan. 8, 2021. The entire contents of both are incorporated herein by reference.

TECHNICAL FIELD

The present invention relates to a compound, a material for organic electroluminescent device, an organic electroluminescent device, and an electronic appliance including the organic electroluminescent device.

BACKGROUND ART

In general, an organic electroluminescent device (hereinafter sometimes referred to as "organic EL device") is composed of an anode, a cathode, and an organic layer interposed between the anode and the cathode. When a voltage is applied between the two electrodes, electrons are injected from the cathode side and holes are injected from the anode side into a light emitting region, the injected electrons and holes are recombined in the light emitting region to generate an excited state, and light is emitted when the excited state returns to the ground state. Accordingly development of a material that efficiently transports electrons or holes into the light emitting region to promote recombination of electrons and holes is important for acquiring a high-performance organic EL device.

PTLs 1 to 8 disclose compounds to be used as a material for organic electroluminescent device.

CITATION LIST

Patent Literature

PTL 1: KR 2017089599 A
PTL 2: KR 2018063710 A
PTL 3: WO 2018/016742
PTL 4: U.S. Pat. No. 7,651,791 B
PTL 5: WO 2013/077352
PTL 6: WO 2013/077362
PTL 7: WO 2019/112214
PTL 8: WO 2020/116615

SUMMARY OF INVENTION

Technical Problem

Although many compounds for organic EL device have conventionally been reported, a compound that further increases the performance of an organic EL device remains to be desired.

The present invention has been made for solving the above problem, and an object of the present invention is to provide a compound that further improves the performance of an organic EL device, an organic EL device having further improved device performance, and an electronic appliance including such an organic EL device.

Solution to Problem

As a result of intensive and extensive studies on the performance of organic EL devices containing compounds described in PTLs 1 to 8, the present inventors have found that an organic EL device containing a compound represented by the following formula (1) shows a higher efficiency.

In an aspect, the present invention provides a compound represented by the following formula (1).

(1)

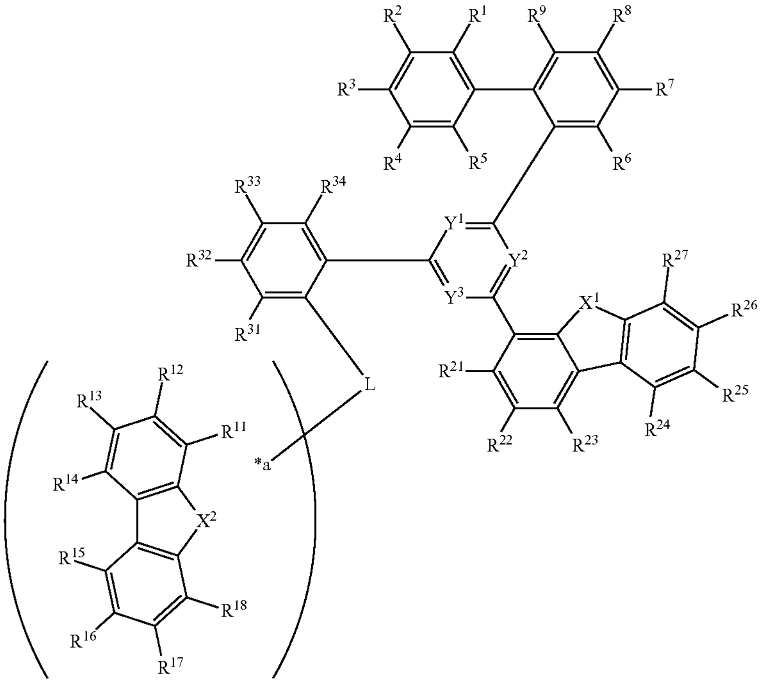

(In the formula, $R^1$ to $R^9$ are each independently selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a canoe group;

provided that, in one or more pairs selected from $R^1$ and $R^2$, $R^2$ and $R^3$, $R^3$ and $R^4$, $R^4$ and $R^5$, $R^6$ and $R^7$, $R^7$ and $R^8$, and $R^8$ and $R^9$, adjacent two may bind to each other to form a substituted or unsubstituted ring structure, or $R^1$ and $R^9$ may bind to each other to form —$Cr^a$b—that crosslinks two benzene rings;

$R^a$ and $R^b$ are each independently selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a cyan group;

two selected from $Y^1$ to $Y^3$ are a nitrogen atom and the remaining one is CR, or all of $Y^1$ to $Y^3$ are a nitrogen atom.

R is selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a canoe group;

$X^1$ is an oxygen atom or a sulfur atom.

$R^{21}$ to $R^{27}$ are each a hydrogen atom.

$R^{31}$ to $R^{34}$ are each independently selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a cyano group;

provided that, in one or more pairs selected from $R^{31}$ and $R^{32}$, $R^{32}$ and $R^{33}$, and $R^{33}$ and $R^{34}$, adjacent two may bind to each other to form a substituted or unsubstituted ring structure;

L is selected from a single bond, a substituted or unsubstituted arylene group having 6 to 50 ring carbon atoms, and a substituted or unsubstituted divalent heterocyclic group having 5 to 30 ring carbon atoms;

one of $R^{11}$ to $R^{14}$ is a single bond binding to *a;

$R^{11}$ to $R^{14}$ that are not a single bond binding to *a and $R^{15}$ to $R^{18}$ are a hydrogen atom;

$X^2$ is selected from an oxygen atom, a sulfur atom, $NR^A$, and $CR^BR^C$;

$R^A$ is selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms;

$R^B$ and $R^C$ are each independently selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a cyano group;

provided that when $R^B$ and $R^C$ are each independently a substituted or unsubstituted aryl group having 6 to 50 ring carbon atoms, the two aryl groups may be crosslinked via —O— or —S—.)

In another aspect, the present invention provides a material for organic EL device, the material containing the compound represented by the formula (1).

In another aspect, the present invention provides an organic electroluminescent device including an anode, a cathode, and an organic layer disposed between the anode and the cathode, the organic layer including a light emitting layer, at least one layer of the organic layer containing the compound represented by the formula (1).

In another aspect, the present invention provides an electronic appliance including the organic electroluminescent device.

Advantageous Effects of Invention

An organic EL device containing the compound represented by the formula (1) shows a high efficiency.

DESCRIPTION OF EMBODIMENTS

Definitions

Figure 1:
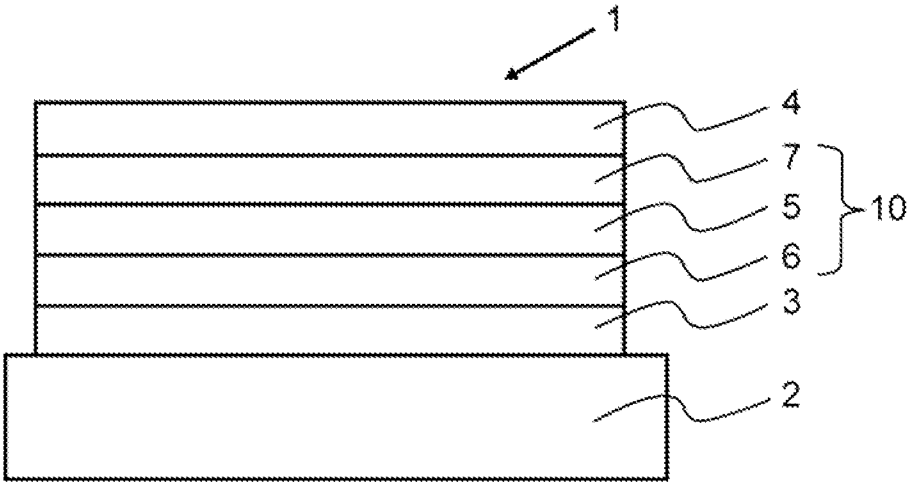
FIG. 1 is a schematic view showing an example of a layer structure of an organic EL device according to an aspect of the present invention.

In the description herein, the hydrogen atom encompasses isotopes thereof having different numbers of neutrons, i.e., a light hydrogen atom (protium), a heavy hydrogen atom (deuterium), and tritium.

In the description herein, the bonding site where the symbol, such as "R", or "D" representing a deuterium atom is not shown is assumed to have a hydrogen atom, i.e., a protium atom, a deuterium atom, or a tritium atom, bonded thereto.

In the description herein, the number of ring carbon atoms shows the number of carbon atoms among the atoms constituting the ring itself of a compound having a structure including atoms bonded to form a ring (such as a monocyclic compound, a condensed ring compound, a bridged compound, a carbocyclic compound, and a heterocyclic compound). In the case where the ring is substituted by a substituent, the carbon atom contained in the substituent is not included in the number of ring carbon atoms. The same definition is applied to the "number of ring carbon atoms" described hereinafter unless otherwise indicated. For example, a benzene ring has 6 ring carbon atoms, a naphthalene ring has 10 ring carbon atoms, a pyridine ring has 5 ring carbon atoms, and a furan ring has 4 ring carbon atoms. For example, 9,9-diphenylfluorenyl group has 13 ring carbon atoms, and 9,9'-spirobifluorenyl group has 25 ring carbon atoms.

In the case where a benzene ring has, for example, an alkyl group substituted thereon as a substituent, the number of carbon atoms of the alkyl group is not included in the number of ring carbon atoms of the benzene ring. Accordingly a benzene ring having an alkyl group substituted thereon has 6 ring carbon atoms. In the case where a naphthalene ring has, for example, an alkyl group substituted thereon as a substituent, the number of carbon atoms of the alkyl group is not included in the number of ring carbon atoms of the naphthalene ring. Accordingly a naphthalene ring having an alkyl group substituted thereon has 10 ring carbon atoms.

In the description herein, the number of ring atoms shows the number of atoms constituting the ring itself of a compound having a structure including atoms bonded to form a ring (such as a monocyclic ring, a condensed ring, and a set of rings) (such as a monocyclic compound, a condensed ring compound, a bridged compound, a carbocyclic compound, and a heterocyclic compound). The atom that does not constitute the ring (such as a hydrogen atom terminating the bond of the atom constituting the ring) and, in the case where the ring is substituted by a substituent, the atom contained in the substituent are not included in the number of ring atoms. The same definition is applied to the "number of ring atoms" described hereinafter unless otherwise indicated. For example, a pyridine ring has 6 ring atoms, a quinazoline ring has 10 ring atoms, and a furan ring has 5 ring atoms. For example, the number of hydrogen atoms bonded to a pyridine ring or atoms constituting a substituent is not included in the number of ring atoms of the pyridine ring. Accordingly a pyridine ring having a hydrogen atom or a substituent bonded thereto has 6 ring atoms. For example, the number of hydrogen atoms bonded to carbon atoms of a quinazoline ring or atoms constituting a substituent is not included in the number of ring atoms of the quinazoline ring. Accordingly a quinazoline ring having a hydrogen atom or a substituent bonded thereto has 10 ring atoms.

In the description herein, the expression "having XX to YY carbon atoms" in the expression "substituted or unsubstituted ZZ group having XX to YY carbon atoms" means the number of carbon atoms of the unsubstituted ZZ group, and, in the case where the ZZ group is substituted, the number of carbon atoms of the substituent is not included. Herein, "YY" is larger than "XX", "XX" represents an integer of 1 or more, and "YY" represents an integer of 2 or more.

In the description herein, the expression "having XX to YY atoms" in the expression "substituted or unsubstituted ZZ group having XX to YY atoms" means the number of atoms of the unsubstituted ZZ group, and, in the case where the ZZ group is substituted, the number of atoms of the substituent is not included. Herein, "YY" is larger than "XX", "XX" represents an integer of 1 or more, and "YY" represents an integer of 2 or more.

In the description herein, an unsubstituted ZZ group means the case where the "substituted or unsubstituted ZZ group" is an "unsubstituted ZZ group", and a substituted ZZ group means the case where the "substituted or unsubstituted ZZ group" is a "substituted ZZ group".

In the description herein, the expression "unsubstituted" in the expression "substituted or unsubstituted ZZ group" means that hydrogen atoms in the ZZ group are not substituted by a substituent. The hydrogen atoms in the "unsubstituted ZZ group" each are a protium atom, a deuterium atom, or a tritium atom.

In the description herein, the expression "substituted" in the expression "substituted or unsubstituted ZZ group" means that one or more hydrogen atom in the ZZ group is substituted by a substituent. The expression "substituted" in the expression "BB group substituted by an AA group" similarly means that one or more hydrogen atom in the BB group is substituted by the AA group.

Substituents in Description

The substituents described in the description herein will be explained.

In the description herein, the number of ring carbon atoms of the "unsubstituted aryl group" is 6 to 50, preferably 6 to 30, and more preferably 6 to 18, unless otherwise indicated in the description.

In the description herein, the number of ring atoms of the "unsubstituted heterocyclic group" is 5 to 50, preferably 5 to 30, and more preferably 5 to 18, unless otherwise indicated in the description.

In the description herein, the number of carbon atoms of the "unsubstituted alkyl group" is 1 to 50, preferably 1 to 20, and more preferably 1 to 6, unless otherwise indicated in the description.

In the description herein, the number of carbon atoms of the "unsubstituted alkenyl group" is 2 to 50, preferably 2 to 20, and more preferably 2 to 6, unless otherwise indicated in the description.

In the description herein, the number of carbon atoms of the "unsubstituted alkynyl group" is 2 to 50, preferably 2 to 20, and more preferably 2 to 6, unless otherwise indicated in the description.

In the description herein, the number of ring carbon atoms of the "unsubstituted cycloalkyl group" is 3 to 50, preferably 3 to 20, and more preferably 3 to 6, unless otherwise indicated in the description.

In the description herein, the number of ring carbon atoms of the "unsubstituted arylene group" is 6 to 50, preferably 6 to 30, and more preferably 6 to 18, unless otherwise indicated in the description.

In the description herein, the number of ring atoms of the "unsubstituted divalent heterocyclic group" is 5 to 50, preferably 5 to 30, and more preferably 5 to 18, unless otherwise indicated in the description.

In the description herein, the number of carbon atoms of the "unsubstituted alkylene group" is 1 to 50, preferably 1 to 20, and more preferably 1 to 6, unless otherwise indicated in the description.

Substituted or Unsubstituted Aryl Group

In the description herein, specific examples (set of specific examples G1) of the "substituted or unsubstituted aryl group" include the unsubstituted aryl groups (set of specific examples G1A) and the substituted aryl groups (set of specific examples G1B) shown below. (Herein, the unsubstituted aryl group means the case where the "substituted or unsubstituted aryl group" is an "unsubstituted aryl group", and the substituted aryl group means the case where the "substituted or unsubstituted aryl group" is a "substituted aryl group".) In the description herein, the simple expression "aryl group" encompasses both the "unsubstituted aryl group" and the "substituted aryl group".

The "substituted aryl group" means a group formed by substituting one or more hydrogen atom of the "unsubstituted aryl group" by a substituent. Examples of the "substituted aryl group" include groups formed by one or more hydrogen atom of each of the "unsubstituted aryl groups" in the set of specific examples G1A by a substituent, and the examples of the substituted aryl groups in the set of specific examples G1B. The examples of the "unsubstituted aryl group" and the examples of the "substituted aryl group" enumerated herein are mere examples, and the "substituted aryl group" in the description herein encompasses groups formed by substituting a hydrogen atom bonded to the carbon atom of the aryl group itself of each of the "substituted aryl groups" in the set of specific examples G1B by a substituent, and groups formed by substituting a hydrogen atom of the substituent of each of the "substituted aryl groups" in the set of specific examples G1B by a substituent.

Unsubstituted Aryl Group (Set of Specific Examples G1A):

- a phenyl group,
- a p-biphenyl group,
- a m-biphenyl group,
- an o-biphenyl group,
- a p-terphenyl-4-yl group,
- a p-terphenyl-3-yl group,
- a p-terphenyl-2-yl group,
- a m-terphenyl-4-yl group,
- a m-terphenyl-3-yl group,
- a m-terphenyl-2-yl group,
- an o-terphenyl-4-yl group,
- an o-terphenyl-3-yl group,
- an o-terphenyl-2-yl group,
- a 1-naphthyl group,
- a 2-naphthyl group,
- an anthryl group,
- a benzanthryl group,
- a phenanthryl group,
- a benzophenanthryl group,
- a phenalenyl group,
- a pyrenyl group,
- a chrysenyl group,
- a benzochrysenyl group,
- a triphenylenyl group,
- a benzotriphenylenyl group,
- a tetracenyl group,
- a pentacenyl group,
- a fluorenyl group,
- a 9,9'-spirobifluorenyl group,
- a benzofluorenyl group,
- a dibenzofluorenyl group,
- a fluoranthenyl group,
- a benzofluoranthenyl group,
- a perylenyl group, and
- monovalent aryl groups derived by removing one hydrogen atom from each of the ring structures represented by the following general formulae (TEMP-1) to (TEMP-15):

(TEMP-1)

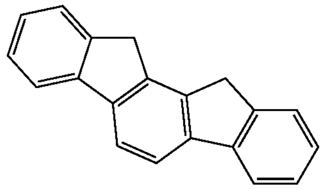

(TEMP-2)

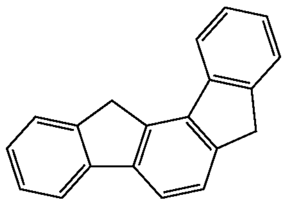

-continued (TEMP-3)

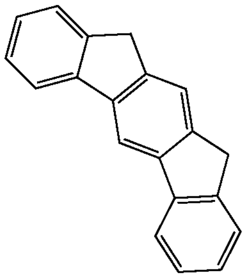

(TEMP-4)

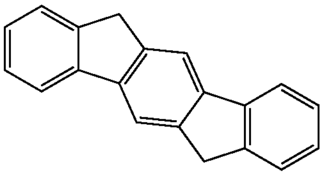

(TEMP-5)

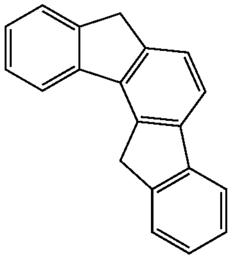

(TEMP-6)

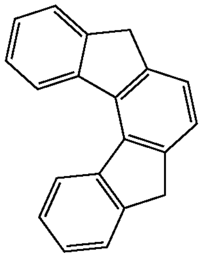

(TEMP-7)

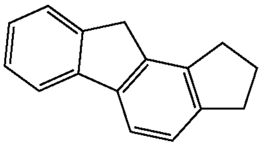

(TEMP-8)

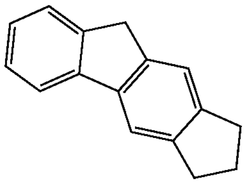

(TEMP-9)

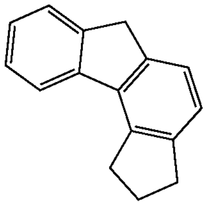

-continued (TEMP-10)

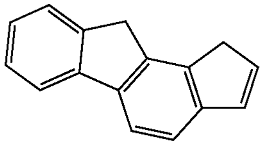

(TEMP-11)

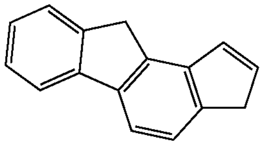

(TEMP-12)

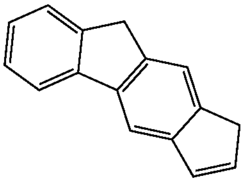

(TEMP-13)

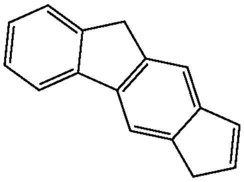

(TEMP-14)

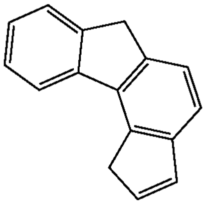

(TEMP-15)

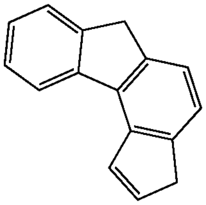

Substituted Aryl Group (Set of Specific Examples G1B):

an o-tolyl group,
a m-tolyl group,
a p-tolyl group,
a p-xylyl group,
a m-xylyl group,
an o-xylyl group,
a p-isopropylphenyl group,
a m-isopropylphenyl group,
an o-isopropylphenyl group,
a p-t-butylphenyl group,
a m-t-butylphenyl group,
a o-t-butylphenyl group,
a 3,4,5-trimethylphenyl group,
a 9,9-dimethylfluorenyl group,
a 9,9-diphenylfluorenyl group,
a 9,9-bis(4-methylphenyl)fluorenyl group,
a 9,9-bis(4-isopropylphenyl)fluorenyl group,
a 9,9-bis(4-t-butylphenyl)fluorenyl group,
a cyanophenyl group,
a triphenylsilylphenyl group,
a trimethylsilylphenyl group,
a phenylnaphthyl group,
a naphthylphenyl group, and
groups formed by substituting one or more hydrogen atom of each of monovalent aryl groups derived from the ring structures represented by the general formulae (TEMP-1) to (TEMP-15) by a substituent.

Substituted or Unsubstituted Heterocyclic Group

In the description herein, the "heterocyclic group" means a cyclic group containing at least one hetero atom in the ring atoms. Specific examples of the hetero atom include a nitrogen atom, an oxygen atom, a sulfur atom, a silicon atom, a phosphorus atom, and a boron atom.

In the description herein, the "heterocyclic group" is a monocyclic group or a condensed ring group.

In the description herein, the "heterocyclic group" is an aromatic heterocyclic group or a non-aromatic heterocyclic group.

In the description herein, specific examples (set of specific examples G2) of the "substituted or unsubstituted heterocyclic group" include the unsubstituted heterocyclic groups (set of specific examples G2A) and the substituted heterocyclic groups (set of specific examples G2B) shown below. (Herein, the unsubstituted heterocyclic group means the case where the "substituted or unsubstituted heterocyclic group" is an "unsubstituted heterocyclic group", and the substituted heterocyclic group means the case where the "substituted or unsubstituted heterocyclic group" is a "substituted heterocyclic group".) In the description herein, the simple expression "heterocyclic group" encompasses both the "unsubstituted heterocyclic group" and the "substituted heterocyclic group".

The "substituted heterocyclic group" means a group formed by substituting one or more hydrogen atom of the "unsubstituted heterocyclic group" by a substituent. Specific examples of the "substituted heterocyclic group" include groups formed by substituting a hydrogen atom of each of the "unsubstituted heterocyclic groups" in the set of specific examples G2A by a substituent, and the examples of the substituted heterocyclic groups in the set of specific examples G2B. The examples of the "unsubstituted heterocyclic group" and the examples of the "substituted heterocyclic group" enumerated herein are mere examples, and the "substituted heterocyclic group" in the description herein encompasses groups formed by substituting a hydrogen atom bonded to the ring atom of the heterocyclic group itself of each of the "substituted heterocyclic groups" in the set of specific examples G2B by a substituent, and groups formed by substituting a hydrogen atom of the substituent of each of the "substituted heterocyclic groups" in the set of specific examples G2B by a substituent.

The set of specific examples G2A includes, for example, the unsubstituted heterocyclic group containing a nitrogen atom (set of specific examples G2A1), the unsubstituted heterocyclic group containing an oxygen atom (set of specific examples G2A2), the unsubstituted heterocyclic group containing a sulfur atom (set of specific examples G2A3), and monovalent heterocyclic groups derived by removing one hydrogen atom from each of the ring structures represented by the following general formulae (TEMP-16) to (TEMP-33) (set of specific examples G2A4).

The set of specific examples G2B includes, for example, the substituted heterocyclic groups containing a nitrogen atom (set of specific examples G2B1), the substituted heterocyclic groups containing an oxygen atom (set of specific examples G2B2), the substituted heterocyclic groups containing a sulfur atom (set of specific examples G2B3), and groups formed by substituting one or more hydrogen atom of each of monovalent heterocyclic groups derived from the ring structures represented by the following general formulae (TEMP-16) to (TEMP-33) by a substituent (set of specific examples G2B4).

Unsubstituted Heterocyclic Group containing Nitrogen Atom (Set of Specific Examples G2A1):

a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolinyl group,
a phthalazinyl group,
a quinazolinyl group,
a quinoxalinyl group,
a benzimidazolyl group,
an indazolyl group,
a phenanthrolinyl group,
a phenanthridinyl group,
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

Unsubstituted Heterocyclic Group containing Oxygen Atom (Set of Specific Examples G2A2):

a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

Unsubstituted Heterocyclic Group containing Sulfur Atom (Set of Specific Examples G2A3):

a thienyl group,
a thiazolyl group,
an isothiazolyl group,
a thiadiazolyl group,
a benzothiophenyl group (benzothienyl group),
an isobenzothiophenyl group (isobenzothienyl group),
a dibenzothiophenyl group (dibenzothienyl group),
a naphthobenzothiophenyl group (naphthobenzothienyl group),
a benzothiazolyl group,
a benzisothiazolyl group,
a phenothiazinyl group,
a dinaphthothiophenyl group (dinaphthothienyl group),
an azadibenzothiophenyl group (azadibenzothienyl group),
a diazadibenzothiophenyl group (diazadibenzothienyl group),
an azanaphthobenzothiophenyl group (azanaphthobenzothienyl group), and
a diazanaphthobenzothiophenyl group (diazanaphthobenzothienyl group).

Monovalent Heterocyclic Group derived by removing One Hydrogen Atom from Ring Structures represented by General Formulae (TEMP-16) to (TEMP-33) (Set of Specific Examples G2A4)

(TEMP-16)

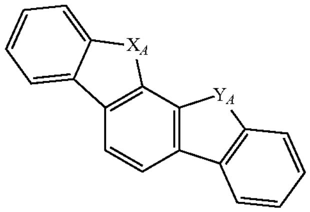

(TEMP-17)

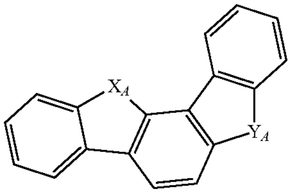

(TEMP-18)

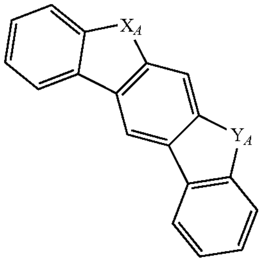

(TEMP-19)

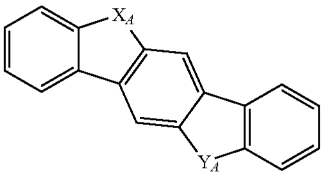

-continued (TEMP-20)

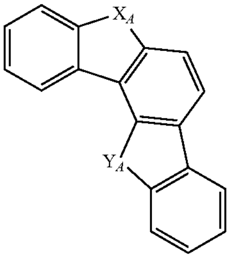

(TEMP-21)

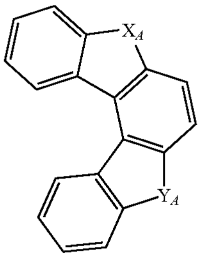

(TEMP-22)

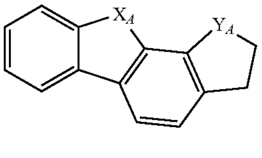

(TEMP-23)

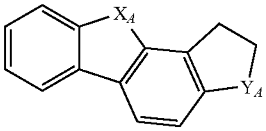

(TEMP-24)

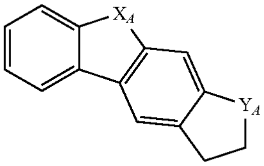

(TEMP-25)

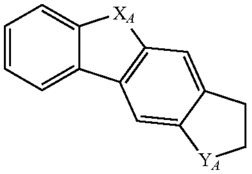

(TEMP-26)

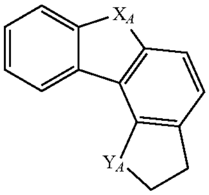

(TEMP-27)

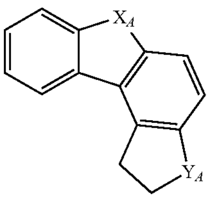

-continued (TEMP-28)

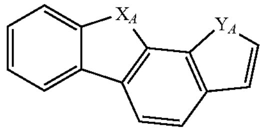

(TEMP-29)

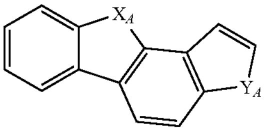

(TEMP-30)

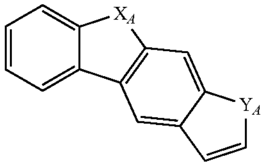

(TEMP-31)

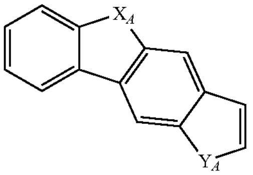

(TEMP-32)

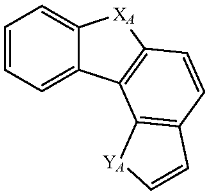

(TEMP-33)

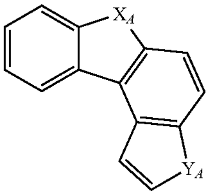

In the general formulae (TEMP-16) to (TEMP-33), $X_A$ and $Y_A$ each independently represent an oxygen atom, a sulfur atom, NH, or $CH_2$, provided that at least one of $X_A$ and $Y_A$ represents an oxygen atom, a sulfur atom, or NH.

In the general formulae (TEMP-16) to (TEMP-83), in the case where at least one of $X_A$ and $Y_A$ represents NH or $CH_2$, the monovalent heterocyclic groups derived from the ring structures represented by the general formulae (TEMP-16) to (TEMP-33) include monovalent groups formed by removing one hydrogen atom from the NH or $CH_2$.

Substituted Heterocyclic Group containing Nitrogen Atom (Set of Specific Examples G2B1):

a (9-phenyl)carbazolyl group,
a (9-biphenyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenyltriazinyl group, a diphenyltriazinyl group,
a phenylquinazolinyl group, and
a biphenylquinazolinyl group.

Substituted Heterocyclic Group containing Oxygen Atom (Set of Specific Examples G2B2):

a phenyldibenzofuranyl group,
a methyldibenzofuranyl group,
a t-butyldibenzofuranyl group, and
a monovalent residual group of spiro[9H-xanthene-9,9'-[9H]fluorene].

Substituted Heterocyclic Group containing Sulfur Atom (Set of Specific Examples G2B3):

a phenyldibenzothiophenyl group,
a methyldibenzothiophenyl group,
a t-butyldibenzothiophenyl group, and
a monovalent residual group of spiro[9H-thioxanthene-9,9'-[9H]fluorene].

Group formed by substituting one or more Hydrogen Atom of Monovalent Heterocyclic Group derived from Ring Structures represented by General Formulae (TEMP-16) to (TEMP-33) by Substituent (Set of Specific Examples G2B4)

The "one or more hydrogen atom of the monovalent heterocyclic group" means one or more hydrogen atom selected from the hydrogen atom bonded to the ring carbon atom of the monovalent heterocyclic group, the hydrogen atom bonded to the nitrogen atom in the case where at least one of $X_A$ and $Y_A$ represents NH, and the hydrogen atom of the methylene group in the case where one of $X_A$ and $Y_A$represents $CH_2$.

Substituted or Unsubstituted Alkyl Group

In the description herein, specific examples (set of specific examples G3) of the "substituted or unsubstituted alkyl group" include the unsubstituted alkyl groups (set of specific examples G3A) and the substituted alkyl groups (set of specific examples G3B) shown below. (Herein, the unsubstituted alkyl group means the case where the "substituted or unsubstituted alkyl group" is an "unsubstituted alkyl group", and the substituted alkyl group means the case where the "substituted or unsubstituted alkyl group" is a "substituted alkyl group".) In the description herein, the simple expression "alkyl group" encompasses both the "unsubstituted alkyl group" and the "substituted alkyl group".

The "substituted alkyl group" means a group formed by substituting one or more hydrogen atom of the "unsubstituted alkyl group" by a substituent. Specific examples of the "substituted alkyl group" include groups formed by substituting one or more hydrogen atom of each of the "unsubstituted alkyl groups" (set of specific examples G3A) by a substituent, and the examples of the substituted alkyl groups (set of specific examples G3B). In the description herein, the alkyl group in the "unsubstituted alkyl group" means a chain-like alkyl group. Accordingly the "unsubstituted alkyl group" encompasses an "unsubstituted linear alkyl group" and an "unsubstituted branched alkyl group". The examples of the "unsubstituted alkyl group" and the examples of the "substituted alkyl group" enumerated herein are mere examples, and the "substituted alkyl group" in the description herein encompasses groups formed by substituting a hydrogen atom of the alkyl group itself of each of the "substituted alkyl groups" in the set of specific examples G3B by a substituent, and groups formed by substituting a hydrogen atom of the substituent of each of the "substituted alkyl groups" in the set of specific examples G3B by a substituent.

Unsubstituted Alkyl Group (Set of Specific Examples G3A):

a methyl group,
an ethyl group,
a n-propyl group,
an isopropyl group,
a n-butyl group,
an isobutyl group,
a s-butyl group, and
a t-butyl group.

Substituted Alkyl Group (Set of Specific Examples G3B):

a heptafluoropropyl group (including isomers),
a pentafluoroethyl group,
a 2,2,2-trifluoroethyl group, and
a trifluoromethyl group.

Substituted or Unsubstituted Alkenyl Group

In the description herein, specific examples (set of specific examples G4) of the "substituted or unsubstituted alkenyl group" include the unsubstituted alkenyl groups (set of specific examples G4A) and the substituted alkenyl groups (set of specific examples G4B) shown below. (Herein, the unsubstituted alkenyl group means the case where the "substituted or unsubstituted alkenyl group" is an "unsubstituted alkenyl group", and the substituted alkenyl group means the case where the "substituted or unsubstituted alkenyl group" is a "substituted alkenyl group".) In the description herein, the simple expression "alkenyl group" encompasses both the "unsubstituted alkenyl group" and the "substituted alkenyl group".

The "substituted alkenyl group" means a group formed by substituting one or more hydrogen atom of the "unsubstituted alkenyl group" by a substituent. Specific examples of the "substituted alkenyl group" include the "unsubstituted alkenyl groups" (set of specific examples G4A) that each have a substituent, and the examples of the substituted alkenyl groups (set of specific examples G4B). The examples of the "unsubstituted alkenyl group" and the examples of the "substituted alkenyl group" enumerated herein are mere examples, and the "substituted alkenyl group" in the description herein encompasses groups formed by substituting a hydrogen atom of the alkenyl group itself of each of the "substituted alkenyl groups" in the set of specific examples G4B by a substituent, and groups formed by substituting a hydrogen atom of the substituent of each of the "substituted alkenyl groups" in the set of specific examples G4B by a substituent.

Unsubstituted Alkenyl Group (Set of Specific Examples G4A):

a vinyl group,
an allyl group,
a 1-butenyl group,
a 2-butenyl group, and
a 3-butenyl group.

Substituted Alkenyl Group (Set of Specific Examples G4B):

a 1,3-butanedienyl group,
a 1-methylvinyl group,
a 1-methylallyl group,
a 1,1-dimethylallyl group,
a 2-methylallyl group, and
a 1,2-dimethylallyl group.

Substituted or Unsubstituted Alkynyl Group

In the description herein, specific examples (set of specific examples G5) of the "substituted or unsubstituted alkynyl group" include the unsubstituted alkynyl group (set of specific examples G5A) shown below. (Herein, the unsubstituted alkynyl group means the case where the "substituted or unsubstituted alkynyl group" is an "unsubstituted alkynyl group".) In the description herein, the simple expression "alkynyl group" encompasses both the "unsubstituted alkynyl group" and the "substituted alkynyl group".

The “substituted alkynyl group” means a group formed by substituting one or more hydrogen atom of the “unsubstituted alkynyl group” by a substituent. Specific examples of the “substituted alkenyl group” include groups formed by substituting one or more hydrogen atom of the “unsubstituted alkynyl group” (set of specific examples G5A) by a substituent.

Unsubstituted Alkynyl Group (Set of Specific Examples G5A):

an ethynyl group.

Substituted or Unsubstituted Cycloalkyl Group

In the description herein, specific examples (set of specific examples G6) of the “substituted or unsubstituted cycloalkyl group” include the unsubstituted cycloalkyl groups (set of specific examples G6A) and the substituted cycloalkyl group (set of specific examples G6B) shown below. (Herein, the unsubstituted cycloalkyl group means the case where the “substituted or unsubstituted cycloalkyl group” is an “unsubstituted cycloalkyl group”, and the substituted cycloalkyl group means the case where the “substituted or unsubstituted cycloalkyl group” is a “substituted cycloalkyl group”.) In the description herein, the simple expression “cycloalkyl group” encompasses both the “unsubstituted cycloalkyl group” and the “substituted cycloalkyl group”.

The “substituted cycloalkyl group” means a group formed by substituting one or more hydrogen atom of the “unsubstituted cycloalkyl group” by a substituent. Specific examples of the “substituted cycloalkyl group” include groups formed by substituting one or more hydrogen atom of each of the “unsubstituted cycloalkyl groups” (set of specific examples G6A) by a substituent, and the example of the substituted cycloalkyl group (set of specific examples G6B). The examples of the “unsubstituted cycloalkyl group” and the examples of the “substituted cycloalkyl group” enumerated herein are mere examples, and the “substituted cycloalkyl group” in the description herein encompasses groups formed by substituting one or more hydrogen atom bonded to the carbon atoms of the cycloalkyl group itself of the “substituted cycloalkyl group” in the set of specific examples G6B by a substituent, and groups formed by substituting a hydrogen atom of the substituent of the “substituted cycloalkyl group” in the set of specific examples G6B by a substituent.

Unsubstituted Cycloalkyl Group (Set of Specific Examples G6A):

a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

Substituted Cycloalkyl Group (Set of Specific Examples G6B):

a 4-methylcyclohexyl group.

Group represented by —Si($R_{901}$)($R_{902}$)($R_{903}$)

In the description herein, specific examples (set of specific examples G7) of the group represented by —Si($R_{901}$)($R_{902}$)($R_{903}$) include:

—Si(G1)(G1)(G1),
—Si(G1)(G2)(G2),
—Si(G1)(G1)(G2),
—Si(G2)(G2)(G2),
—Si(G3)(G3)(G3), and
—Si(G6)(G6)(G6).

Herein,

G1 represents the “substituted or unsubstituted aryl group” described in the set of specific examples G1, G2 represents the “substituted or unsubstituted heterocyclic group” described in the set of specific examples G2, G3 represents the “substituted or unsubstituted alkyl group” described in the set of specific examples G3, and G6 represents the “substituted or unsubstituted cycloalkyl group” described in the set of specific examples G6.

Plural groups represented by G1 in —Si(G1)(G1)(G1) are the same as or different from each other.

Plural groups represented by G2 in —Si(G1)(G2)(G2) are the same as or different from each other.

Plural groups represented by G1 in —Si(G1)(G1)(G2) are the same as or different from each other.

Plural groups represented by G2 in —Si(G2)(G2)(G2) are the same as or different from each other.

Plural groups represented by G3 in —Si(G3)(G3)(G3) are the same as or different from each other.

Plural groups represented by G6 in —Si(G6)(G6)(G6) are the same as or different from each other.

Group Represented by —O—($R_{904}$)

In the description herein, specific examples (set of specific examples G8) of the group represented by —O—($R_{904}$) include:

—O(G1),
—O(G2),
—O(G3), and
—O(G6).

Herein,

G1 represents the “substituted or unsubstituted aryl group” described in the set of specific examples G1, G2 represents the “substituted or unsubstituted heterocyclic group” described in the set of specific examples G2, G3 represents the “substituted or unsubstituted alkyl group” described in the set of specific examples G3, and G6 represents the “substituted or unsubstituted cycloalkyl group” described in the set of specific examples G6.

Group represented by —S—($R_{905}$)

In the description herein, specific examples (set of specific examples G9) of the group represented by —S—($R_{905}$) include:

—S(G1),
—S(G2),
—S(G3), and
—S(G6).

Herein,

G1 represents the “substituted or unsubstituted aryl group” described in the set of specific examples G1, G2 represents the “substituted or unsubstituted heterocyclic group” described in the set of specific examples G2, G3 represents the “substituted or unsubstituted alkyl group” described in the set of specific examples G3, and G6 represents the “substituted or unsubstituted cycloalkyl group” described in the set of specific examples G6.

Group represented by —N($R_{906}$)($R_{907}$)

In the description herein, specific examples (set of specific examples G10) of the group represented by —N($R_{906}$)($R_{907}$) include:

—N(G1)(G1),
—N(G2)(G2),

—N(G1)(G2),

—N(G3)(G3), and

—N(G6)(G6).

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Plural groups represented by G1 in —N(G1)(G1) are the same as or different from each other.

Plural groups represented by G2 in —N(G2)(G2) are the same as or different from each other.

Plural groups represented by G3 in —N(G3)(G3) are the same as or different from each other.

Plural groups represented by G6 in —N(G6)(G6) are the same as or different from each other.

Halogen Atom

In the description herein, specific examples (set of specific examples G11) of the "halogen atom" include a fluorine atom, a chlorine atom, a bromine atom, and an iodine atom.

Substituted or Unsubstituted Fluoroalkyl Group

In the description herein, the "substituted or unsubstituted fluoroalkyl group" means a group formed by substituting at least one hydrogen atom bonded to the carbon atom constituting the alkyl group in the "substituted or unsubstituted alkyl group" by a fluorine atom, and encompasses a group formed by substituting all the hydrogen atoms bonded to the carbon atoms constituting the alkyl group in the "substituted or unsubstituted alkyl group" by fluorine atoms (i.e., a perfluoroalkyl group). The number of carbon atoms of the "unsubstituted fluoroalkyl group" is 1 to 50, preferably 1 to 30, and more preferably 1 to 18, unless otherwise indicated in the description. The "substituted fluoroalkyl group" means a group formed by substituting one or more hydrogen atom of the "fluoroalkyl group" by a substituent. In the description herein, the "substituted fluoroalkyl group" encompasses a group formed by substituting one or more hydrogen atom bonded to the carbon atom of the alkyl chain in the "substituted fluoroalkyl group" by a substituent, and a group formed by substituting one or more hydrogen atom of the substituent in the "substituted fluoroalkyl group" by a substituent. Specific examples of the "unsubstituted fluoroalkyl group" include examples of groups formed by substituting one or more hydrogen atom in each of the "alkyl group" (set of specific examples G3) by a fluorine atom.

Substituted or Unsubstituted Haloalkyl Group

In the description herein, the "substituted or unsubstituted haloalkyl group" means a group formed by substituting at least one hydrogen atom bonded to the carbon atom constituting the alkyl group in the "substituted or unsubstituted alkyl group" by a halogen atom, and encompasses a group formed by substituting all the hydrogen atoms bonded to the carbon atoms constituting the alkyl group in the "substituted or unsubstituted alkyl group" by halogen atoms. The number of carbon atoms of the "unsubstituted haloalkyl group" is 1 to 50, preferably 1 to 30, and more preferably 1 to 18, unless otherwise indicated in the description. The "substituted haloalkyl group" means a group formed by substituting one or more hydrogen atom of the "haloalkyl group" by a substituent. In the description herein, the "substituted haloalkyl group" encompasses a group formed by substituting one or more hydrogen atom bonded to the carbon atom of the alkyl chain in the "substituted haloalkyl group" by a substituent, and a group formed by substituting one or more hydrogen atom of the substituent in the "substituted haloalkyl group" by a substituent. Specific examples of the "unsubstituted haloalkyl group" include examples of groups formed by substituting one or more hydrogen atom in each of the "alkyl group" (set of specific examples G3) by a halogen atom. A haloalkyl group may be referred to as a halogenated alkyl group in some cases.

Substituted or Unsubstituted Alkoxy Group

In the description herein, specific examples of the "substituted or unsubstituted alkoxy group" include a group represented by —O(G3), wherein G3 represents the "substituted or unsubstituted alkyl group" described in the set of specific examples G3. The number of carbon atoms of the "unsubstituted alkoxy group" is 1 to 50, preferably 1 to 30, and more preferably 1 to 18, unless otherwise indicated in the description.

Substituted or Unsubstituted Alkylthio Group

In the description herein, specific examples of the "substituted or unsubstituted alkylthio group" include a group represented by —S(G3), wherein G3 represents the "substituted or unsubstituted alkyl group" described in the set of specific examples G3. The number of carbon atoms of the "unsubstituted alkylthio group" is 1 to 50, preferably 1 to 30, and more preferably 1 to 18, unless otherwise indicated in the description.

Substituted or Unsubstituted Aryloxy Group

In the description herein, specific examples of the "substituted or unsubstituted aryloxy group" include a group represented by —O(G1), wherein G1 represents the "substituted or unsubstituted aryl group" described in the set of specific examples G1. The number of ring carbon atoms of the "unsubstituted aryloxy group" is 6 to 50, preferably 6 to 30, and more preferably 6 to 18, unless otherwise indicated in the description.

Substituted or Unsubstituted Arylthio Group

In the description herein, specific examples of the "substituted or unsubstituted arylthio group" include a group represented by —S(G1), wherein G1 represents the "substituted or unsubstituted aryl group" described in the set of specific examples G1. The number of ring carbon atoms of the "unsubstituted arylthio group" is 6 to 50, preferably 6 to 30, and more preferably 6 to 18, unless otherwise indicated in the description.

Substituted or Unsubstituted Trialkylsilyl Group

In the description herein, specific examples of the "trialkylsilyl group" include a group represented by —Si(G3)(G3)(G3), wherein G3 represents the "substituted or unsubstituted alkyl group" described in the set of specific examples G3. Plural groups represented by G3 in —Si(G3)(G3)(G3) are the same as or different from each other. The number of carbon atoms of each of alkyl groups of the "substituted or unsubstituted trialkylsilyl group" is 1 to 50, preferably 1 to 20, and more preferably 1 to 6, unless otherwise indicated in the description.

Substituted or Unsubstituted Aralkyl Group

In the description herein, specific examples of the "substituted or unsubstituted aralkyl group" include a group represented by -(G3)-(G1), wherein G3 represents the "substituted or unsubstituted alkyl group" described in the set of specific examples G3, and G1 represents the "substituted or unsubstituted aryl group" described in the set of specific examples G1. Accordingly the "aralkyl group" is a group formed by substituting a hydrogen atom of an "alkyl group" by an "aryl group" as a substituent, and is one embodiment of the "substituted alkyl group". The "unsubstituted aralkyl group" is an "unsubstituted alkyl group" that is substituted by an "unsubstituted aryl group", and the number of carbon atoms of the "unsubstituted aralkyl group" is 7 to 50, preferably 7 to 30, and more preferably 7 to 18, unless otherwise indicated in the description.

Specific examples of the "substituted or unsubstituted aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a 6-naphthylmethyl group, a 1-β-naphthylethyl group, a 2-β-naphthylethyl group, a 1-β-naphthylisopropyl group, and a 2-β-naphthylisopropyl group.

In the description herein, the substituted or unsubstituted aryl group is preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-dimethylfluorenyl group, a 9,9-diphenylfluorenyl group, and the like, unless otherwise indicated in the description.

In the description herein, the substituted or unsubstituted heterocyclic group is preferably a pyridyl group, a pyrimidinyl group, a triazinyl group, a quinolyl group, an isoquinolyl group, a quinazolinyl group, a benzimidazolyl group, a phenanthrolinyl group, a carbazolyl group (e.g., a 1-carbazolyl, group, a 2-carbazolyl, group, a 3-carbazolyl, group, a 4-carbazolyl, group, or a 9-carbazolyl, group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (e.g., a (9-phenyl)carbazol-1-yl group, a (9-phenyl)carbazol-2-yl group, a (9-phenyl(carbazol-3-yl group, or a (9-phenyl) carbazol-4-yl group), a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, a phenyldibenzothiophenyl group, and the like, unless otherwise indicated in the description.

In the description herein, the carbazolyl group is specifically any one of the following groups unless otherwise indicated in the description.

(TEMP-Cz1)

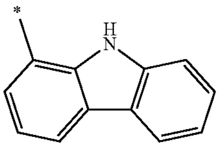

(TEMP-Cz2)

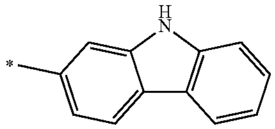

-continued (TEMP-Cz3)

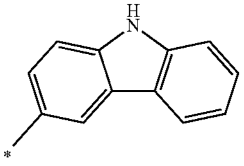

(TEMP-Cz4)

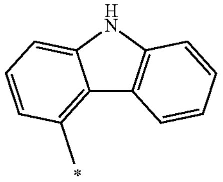

(TEMP-Cz5)

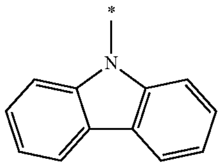

In the description herein, the (9-phenyl)carbazolyl group is specifically any one of the following groups unless otherwise indicated in the description.

(TEMP-Cz6)

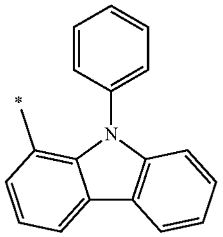

(TEMP-Cz7)

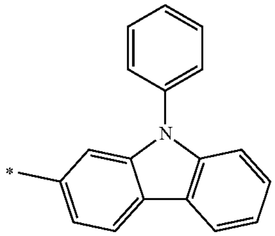

(TEMP-Cz8)

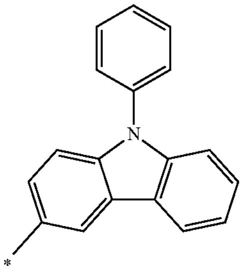

-continued (TEMP-Cz9)

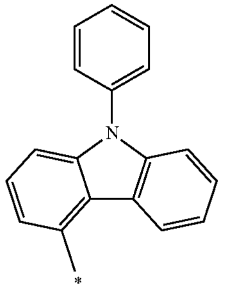

In the general formulae (TEMP-Cz1) to (TEMP-Cz9), represents a bonding site.

In the description herein the dibenzofuranyl group and the dibenzothiophenyl group are specifically any one of the following groups unless otherwise indicated in the description, (TEMP-34)

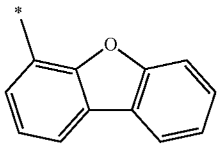

(TEMP-35)

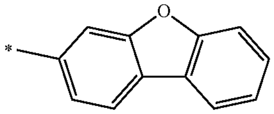

(TEMP-36)

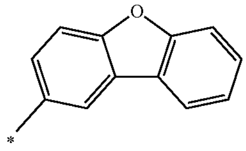

(TEMP-37)

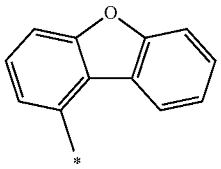

(TEMP-38)

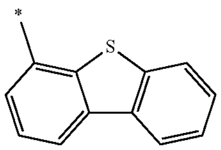

(TEMP-39)

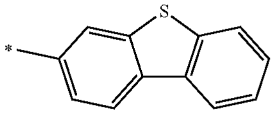

(TEMP-40)

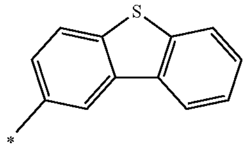

-continued (TEMP-41)

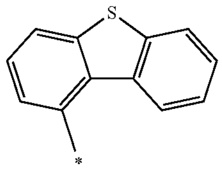

In the general formulae (TEMP-34) to (TEMP-41), * represents a bonding site.

In the description herein, the substituted or unsubstituted alkyl group is preferably a methyl group, an ethyl group, a propyl group, an isopropyl group, a n-butyl group, an isobutyl group, a t-butyl group, or the like unless otherwise indicated in the description.

Substituted or Unsubstituted Arylene Group

In the description herein, the "substituted or unsubstituted arylene group" is a divalent group derived by removing one hydrogen atom on the aryl ring from the "substituted or unsubstituted aryl group" described above unless otherwise indicated in the description. Specific examples (set of specific examples G12) of the "substituted or unsubstituted arylene group" include divalent groups derived by removing one hydrogen atom on the aryl ring from the "substituted or unsubstituted aryl groups" described in the set of specific examples G1.

Substituted or Unsubstituted Divalent Heterocyclic Group

In the description herein, the "substituted or unsubstituted divalent heterocyclic group" is a divalent group derived by removing one hydrogen atom on the heterocyclic ring from the "substituted or unsubstituted heterocyclic group" described above unless otherwise indicated in the description. Specific examples (set of specific examples G13) of the "substituted or unsubstituted divalent heterocyclic group" include divalent groups derived by removing one hydrogen atom on the heterocyclic ring from the "substituted or unsubstituted heterocyclic groups" described in the set of specific examples G2.

Substituted or Unsubstituted Alkylene Group

In the description herein, the "substituted or unsubstituted alkylene group" is a divalent group derived by removing one hydrogen atom on the alkyl chain from the "substituted or unsubstituted alkyl group" described above unless otherwise indicated in the description. Specific examples (set of specific examples G14) of the "substituted or unsubstituted alkylene group" include divalent groups derived by removing one hydrogen atom on the alkyl chain from the "substituted or unsubstituted alkyl groups" described in the set of specific examples G3.

In the description herein, the substituted or unsubstituted arylene group is preferably any one of the groups represented by the following general formulae (TEMP-42) to (TEMP-68) unless otherwise indicated in the description.

(TEMP-42)

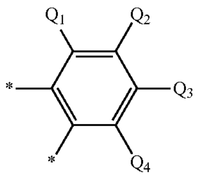

-continued
(TEMP-43)
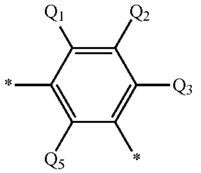
(TEMP-44)
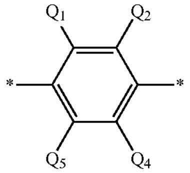
(TEMP-45)
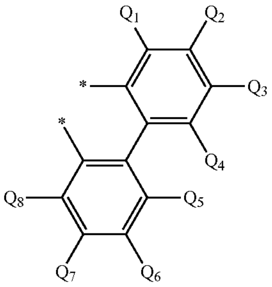
(TEMP-46)
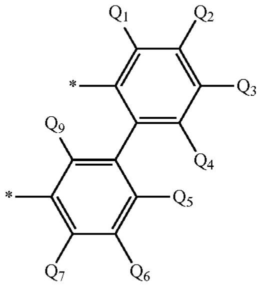
(TEMP-47)
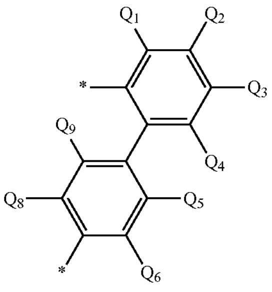
(TEMP-48)
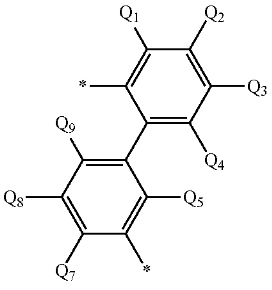
-continued
(TEMP-49)
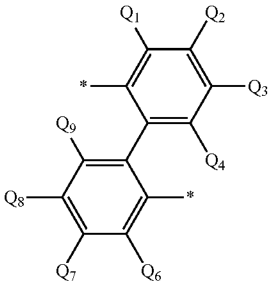
(TEMP-50)
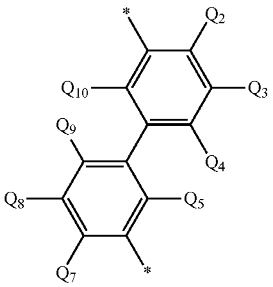
(TEMP-51)
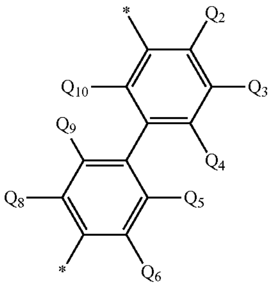
(TEMP-52)
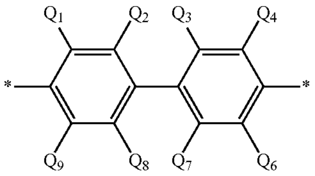
In the general formulae (TEMP-42) to (TEMP-52), $Q_1$ to $Q_{10}$ each independently represent a hydrogen atom or substituent.
In the general formulae (TEMP-42) to (TEMP-52) * represents a bonding site.
(TEMP-53)
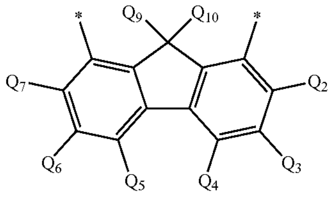

-continued
(TEMP-54)
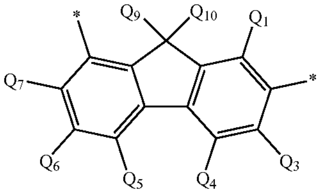
(TEMP-55)
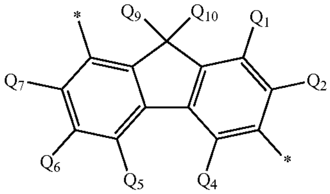
(TEMP-56)
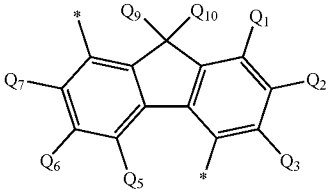
(TEMP-57)
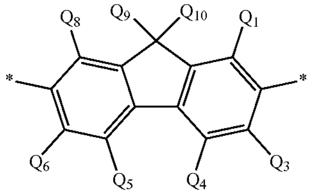
(TEMP-58)
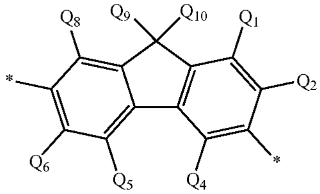
(TEMP-59)
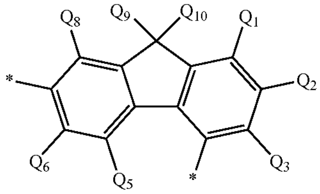
(TEMP-60)
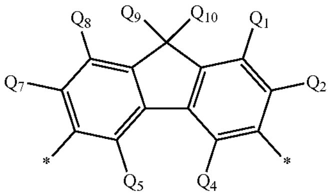
(TEMP-61)
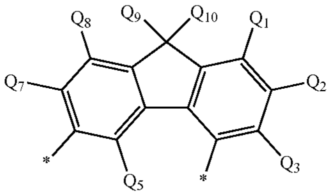
-continued
(TEMP-62)
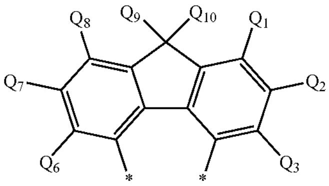
In the general formulae (TEMP-53) to (TEMP-62), $Q_1$ to $Q_{10}$ each independently represent a hydrogen atom or a substituent.
The formulae $Q_9$ and $Q_{10}$ may be bonded to each other to form a ring via a single bond.
In the general formulae (TEMP-53) to (TEMP-62),* represents a bonding site.
(TEMP-63)
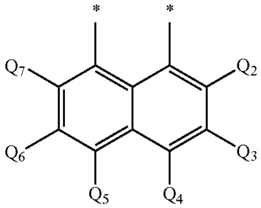
(TEMP-64)
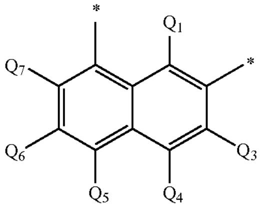
(TEMP-65)
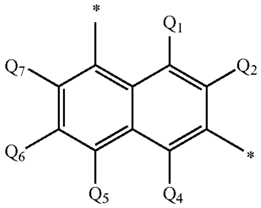
(TEMP-66)
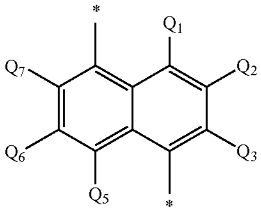
(TEMP-67)
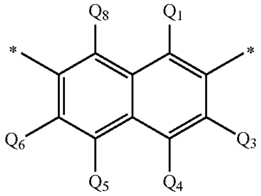

-continued (TEMP-68)

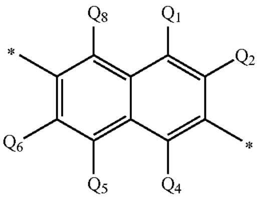

In the general formulae (TEMP-63) to (TEMP-68), $Q_1$ to $Q_8$ each independently represent a hydrogen atom or a substituent.

In the general formulae (TEMP-63) to (TEMP-68), * represents a bonding site.

In the description herein, the substituted or unsubstituted divalent heterocyclic group is preferably the groups represented by the following general formulae, (TEMP-69) to (TEMP-102) unless otherwise indicated in the description.

(TEMP-69)

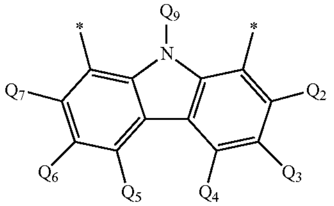

(TEMP-70)

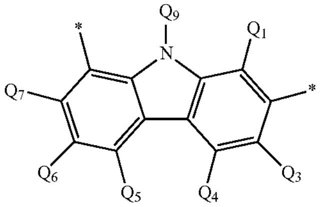

(TEMP-71)

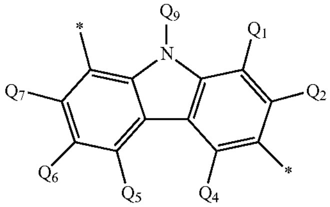

(TEMP-72)

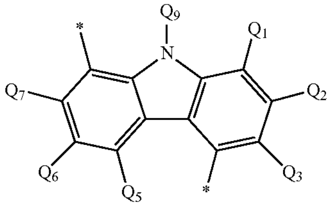

(TEMP-73)

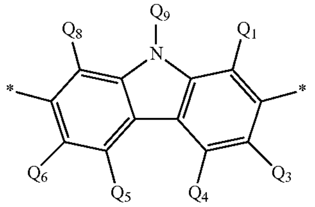

-continued (TEMP-74)

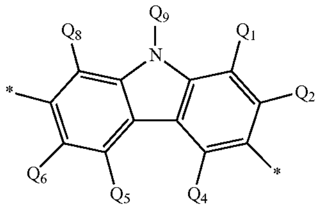

(TEMP-75)

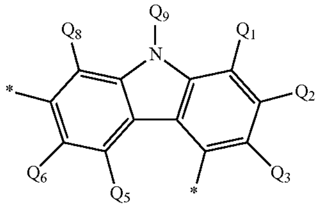

(TEMP-76)

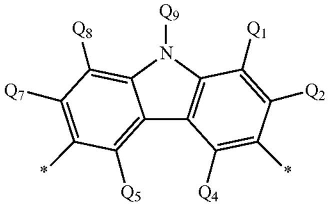

(TEMP-77)

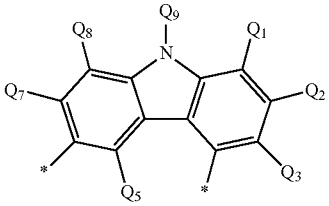

(TEMP-78)

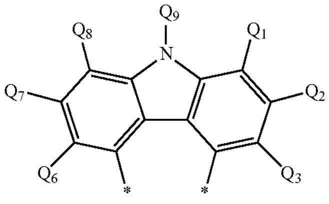

(TEMP-79)

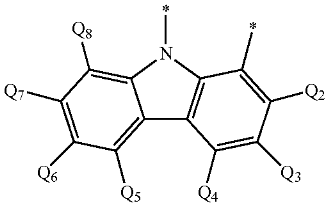

(TEMP-80)

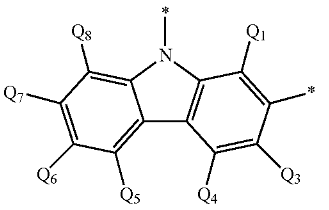

-continued
(TEMP-81)
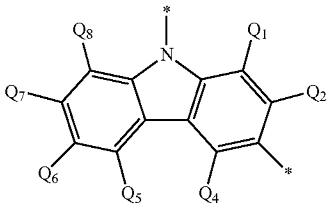
(TEMP-82)
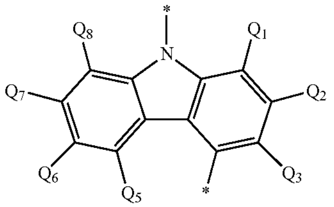
In the general formulae (TEMP-69) to (TEMP-82), $Q_1$ to $Q_9$ each independently represent a hydrogen atom or a substituent.
(TEMP-83)
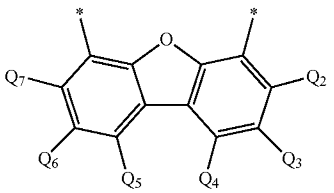
(TEMP-84)
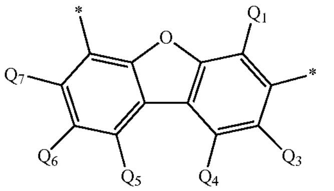
(TEMP-85)
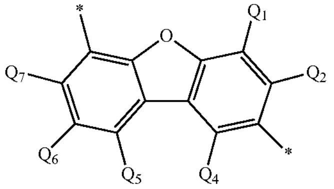
(TEMP-86)
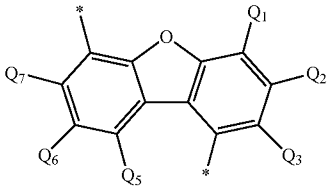
(TEMP-87)
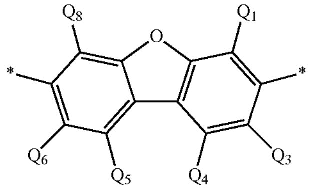
-continued
(TEMP-88)
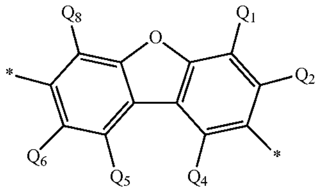
(TEMP-89)
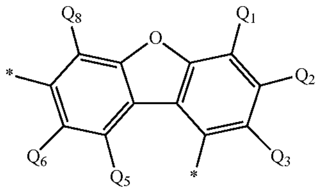
(TEMP-90)
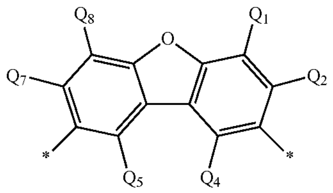
(TEMP-91)
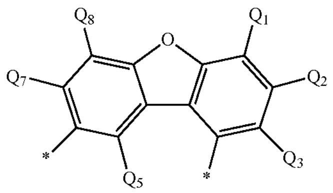
(TEMP-92)
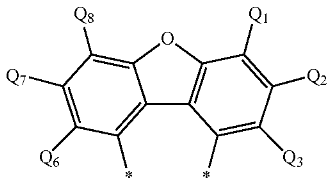
(TEMP-93)
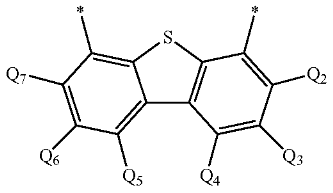
(TEMP-94)
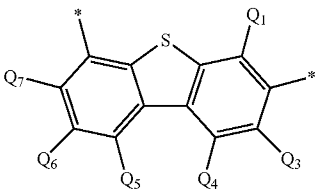
(TEMP-95)
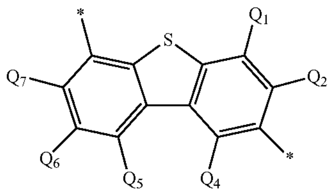

-continued (TEMP-96)

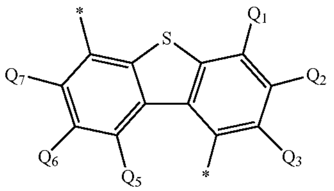

(TEMP-97)

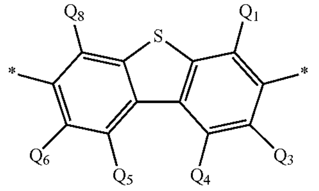

(TEMP-98)

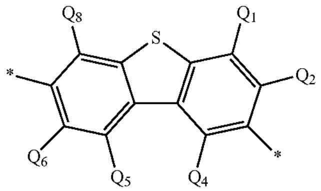

(TEMP-99)

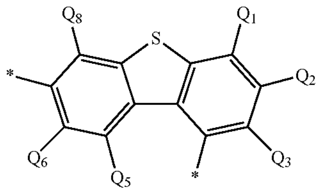

(TEMP-100)

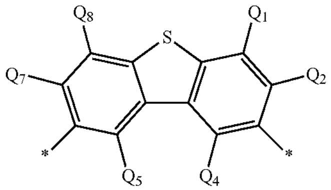

(TEMP-101)

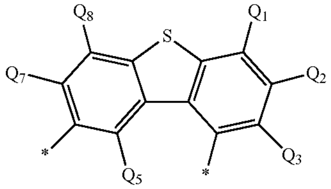

(TEMP-102)

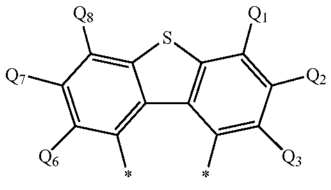

In the general formulae (TEMP-83) to (TEMP-102), $Q_1$ to $Q_8$ each independently represent a hydrogen atom or a substituent.

The above are the explanation of the "substituents in the description herein".

Case Forming Ring by Bonding

In the description herein, the case where "one or more combinations of combinations each including adjacent two or more each are bonded to each other to form a substituted or unsubstituted monocyclic ring, or each are bonded to each other to form a substituted or unsubstituted condensed ring, or each are not bonded to each other" means a case where "one or more combinations of combinations each including adjacent two or more each are bonded to each other to form a substituted or unsubstituted monocyclic ring", a case where "one or more combinations of combinations each including adjacent two or more each are bonded to each other to form a substituted or unsubstituted condensed ring", and a case where "one or more combinations of combinations each including adjacent two or more each are not bonded to each other".

In the description herein, the case where "one or more combinations of combinations each including adjacent two or more each are bonded to each other to form a substituted or unsubstituted monocyclic ring" and the case where "one or more combinations of combinations each including adjacent two or more each are bonded to each other to form a substituted or unsubstituted condensed ring" (which may be hereinafter collectively referred to as a "case forming a ring by bonding") will be explained below. The cases will be explained for the anthracene compound represented by the following general formula (TEMP-103) having an anthracene core skeleton as an example.

(TEMP-103)

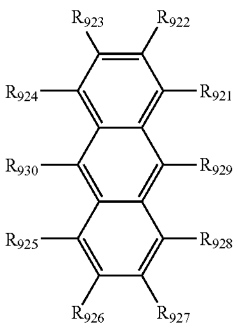

For example, in the case where "one or more combinations of combinations each including adjacent two or more each are bonded to each other to form a ring" among $R_{921}$ to $R_{930}$, the combinations each including adjacent two as one combination include a combination of $R_{921}$ and $R_{922}$, combination of $R_{922}$ and $R_{923}$, a combination of $R_{923}$ and $R_{924}$, a combination of $R_{924}$ and $R_{930}$, a combination of $R_{930}$ and $R_{925}$, a combination of $R_{925}$ and $R_{926}$, a combination of $R_{926}$ and $R_{927}$, a combination of $R_{927}$ and $R_{928}$, a combination of $R_{928}$ and $R_{929}$, and a combination of $R_{929}$ and $R_{921}$.

The "one or more combinations" mean that two or more combinations each including adjacent two or more may form rings simultaneously. For example, in the case where $R_{921}$ and $R_{922}$ are bonded to each other to form a ring $Q_A$, and simultaneously $R_{925}$ and $R_{926}$ are bonded to each other to form a ring $Q_B$, the anthracene compound represented by the general formula (TEMP-103) is represented by the following general formula (TEMP-104).

(TEMP-104)

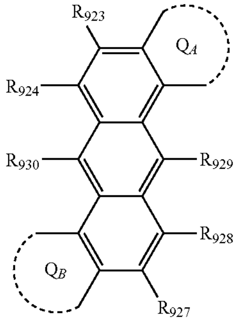

The case where the "combination including adjacent two or more forms rings" encompasses not only the case where adjacent two included in the combination are bonded as in the aforementioned example, but also the case where adjacent three or more included in the combination are bonded. For example, this case means that $R_{921}$ and $R_{922}$ are bonded to each other to form a ring $Q_A$, $R_{922}$ and $R_{923}$ are bonded to each other to form a ring $Q_C$, and adjacent three ($R_{921}$, $R_{922}$, and $R_{923}$) included in the combination are bonded to each other to form rings, which are condensed to the anthracene core skeleton, and in this case, the anthracene compound represented by the general formula (TEMP-103) is represented by the following general formula (TEMP-105). In the following general formula (TEMP-105), the ring $Q_A$ and the ring $Q_C$ share $R_{922}$.

(TEMP-105)

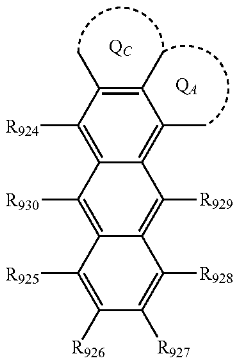

The formed "monocyclic ring" or "condensed ring" may be a saturated ring or an unsaturated ring in terms of structure of the formed ring itself. In the case where the "one combination including adjacent two" forms a "monocyclic ring" or a "condensed ring", the "monocyclic ring" or the "condensed ring" may form a saturated ring or an unsaturated ring. For example, the ring $Q_A$ and the ring $Q_B$ formed in the general formula (TEMP-104) each are a "monocyclic ring" or a "condensed ring". The ring $Q_A$ and the ring $Q_C$ formed in the general formula (TEMP-105) each are a "condensed ring". The ring $Q_A$ and the ring $Q_C$ in the general formula (TEMP-105) form a condensed ring through condensation of the ring $Q_A$ and the ring $Q_C$. In the case where the ring $Q_A$ in the general formula (TEMP-104) is a benzene ring, the ring $Q_A$ is a monocyclic ring. In the case where the ring $Q_A$ in the general formula (TEMP-104) is a naphthalene ring, the ring $Q_A$ is a condensed ring.

The "unsaturated ring" means an aromatic hydrocarbon ring or an aromatic heterocyclic ring. The "saturated ring" means an aliphatic hydrocarbon ring or a non-aromatic heterocyclic ring.

Specific examples of the aromatic hydrocarbon ring include the structures formed by terminating the groups exemplified as the specific examples in the set of specific examples G1 with a hydrogen atom.

Specific examples of the aromatic heterocyclic ring include the structures formed by terminating the aromatic heterocyclic groups exemplified as the specific examples in the set of specific examples G2 with a hydrogen atom.

Specific examples of the aliphatic hydrocarbon ring include the structures formed by terminating the groups exemplified as the specific examples in the set of specific examples G6 with a hydrogen atom.

The expression "to form a ring" means that the ring is formed only with the plural atoms of the core structure or with the plural atoms of the core structure and one or more arbitrary element. For example, the ring $Q_A$ formed by bonding $R_{921}$ and $R_{922}$ each other shown in the general formula (TEMP-104) means a ring formed with the carbon atom of the anthracene skeleton bonded to $R_{921}$, the carbon atom of the anthracene skeleton bonded to $R_{922}$, and one or more arbitrary element. As a specific example, in the case where the ring $Q_A$ is formed with $R_{921}$ and $R_{922}$, and in the case where a monocyclic unsaturated ring is formed with the carbon atom of the anthracene skeleton bonded to $R_{921}$, the carbon atom of the anthracene skeleton bonded to $R_{922}$, and four carbon atoms, the ring formed with $R_{921}$ and $R_{922}$ is a benzene ring.

Herein, the "arbitrary element" is preferably at least one kind of an element selected from the group consisting of a carbon element, a nitrogen element, an oxygen element, and a sulfur element, unless otherwise indicated in the description. For the arbitrary element (for example, for a carbon element or a nitrogen element), a bond that does not form a ring may be terminated with a hydrogen atom or the like, and may be substituted by an "arbitrary substituent" described later. In the case where an arbitrary element other than a carbon element is contained, the formed ring is a heterocyclic ring.

The number of the "one or more arbitrary element" constituting the monocyclic ring or the condensed ring is preferably 2 or more and 15 or less, more preferably 3 or more and 12 or less, and further preferably 3 or more and 5 or less, unless otherwise indicated in the description.

What is preferred between the "monocyclic ring" and the "condensed ring" is the "monocyclic ring" unless otherwise indicated in the description.

What is preferred between the "saturated ring" and the "unsaturated ring" is the "unsaturated ring" unless otherwise indicated in the description.

The "monocyclic ring" is preferably a benzene ring unless otherwise indicated in the description.

The "unsaturated ring" is preferably a benzene ring unless otherwise indicated in the description.

In the case where the "one or more combinations of combinations each including adjacent two or more" each are "bonded to each other to form a substituted or unsubstituted monocyclic ring", or each are "bonded to each other to form a substituted or unsubstituted condensed ring", it is preferred that the one or more combinations of combinations each including adjacent two or more each are bonded to each other to form a substituted or unsubstituted "unsaturated ring" containing the plural atoms of the core skeleton and 1 or more and 15 or less at least one kind of an element selected from the group consisting of a carbon element, a nitrogen element, an oxygen element, and a sulfur element, unless otherwise indicated in the description.

In the case where the "monocyclic ring" or the "condensed ring" has a substituent, the substituent is, for example, an "arbitrary substituent" described later. In the case where the "monocyclic ring" or the "condensed ring" has a substituent, specific examples of the substituent include the substituents explained in the section "Substituents in Description" described above.

In the case where the "saturated ring" or the "unsaturated ring" has a substituent, the substituent is, for example, an "arbitrary substituent" described later. In the case where the "monocyclic ring" or the "condensed ring" has a substituent, specific examples of the substituent include the substituents explained in the section "Substituents in Description" described above.

The above are the explanation of the case where "one or more combinations of combinations each including adjacent two or more" each are "bonded to each other to form a substituted or unsubstituted monocyclic ring", and the case where "one or more combinations of combinations each including adjacent two or more" each are "bonded to each other to form a substituted or unsubstituted condensed ring" (i.e., the "case forming a ring by bonding").

Substituent for "Substituted or Unsubstituted"

In one embodiment in the description herein, the substituent for the case of "substituted or unsubstituted" (which may be hereinafter referred to as an "arbitrary substituent") is, for example, a group selected from the group consisting of an unsubstituted alkyl group having 1 to 50 carbon atoms,
an unsubstituted alkenyl group having 2 to 50 carbon atoms,
an unsubstituted alkynyl group having 2 to 50 carbon atoms,
an unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
an unsubstituted aryl group having 6 to 50 ring carbon atoms, and
an unsubstituted heterocyclic group having 5 to 50 ring atoms,
wherein $R_{901}$ to $R_{907}$ each independently represent
a hydrogen atom,
a substituted or unsubstituted alkyl group having 1 to 50 carbon atoms
a substituted or unsubstituted cycloalkyl group having 3 to 50 ring carbon atoms,
a substituted or unsubstituted aryl group having 6 to 50 ring carbon atoms, or
a substituted or unsubstituted heterocyclic group having 5 to 50 ring atoms.

In the case where two or more groups each represented by $R_{901}$ exist, the two or more groups each represented by $R_{901}$ are the same as or different from each other, in the case where two or more groups each represented by $R_{902}$ exist, the two or more groups each represented by $R_{902}$ are the same as or different from each other, in the case where two or more groups each represented by $R_{903}$ exist, the two or more groups each represented by $R_{903}$ are the same as or different from each other, in the case where two or more groups each represented by $R_{904}$ exist, the two or more groups each represented by $R_{904}$ are the same as or different from each other, in the case where two or more groups each represented by $R_{905}$ exist, the two or more groups each represented by $R_{905}$ are the same as or different from each other, in the case where two or more groups each represented by $R_{906}$ exist, the two or more groups each represented by $R_{906}$ are the same as or different from each other, and in the case where two or more groups each represented by $R_{907}$ exist, the two or more groups each represented by $R_{907}$ are the same as or different from each other.

In one embodiment, the substituent for the case of "substituted or unsubstituted" may be a group selected from the group consisting of an alkyl group having 1 to 50 carbon atoms,
an aryl group having 6 to 50 ring carbon atoms, and
a heterocyclic group having 5 to 50 ring atoms.

In one embodiment, the substituent for the case of "substituted or unsubstituted" may be a group selected from the group consisting of an alkyl group having 1 to 18 carbon atoms,
an aryl group having 6 to 18 ring carbon atoms, and
a heterocyclic group having 5 to 18 ring atoms.

The specific examples of the groups for the arbitrary substituent described above are the specific examples of the substituent described in the section "Substituents in Description" described above.

In the description herein, the arbitrary adjacent substituents may form a "saturated ring" or an "unsaturated ring", preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, and more preferably form a benzene ring, unless otherwise indicated.

In the description herein, the arbitrary substituent may further have a substituent unless otherwise indicated in the description. The definition of the substituent that the arbitrary substituent further has may be the same as the arbitrary substituent.

In the description herein, a numerical range shown by "AA to BB" means a range including the numerical value AA as the former of "AA to BB" as the lower limit value and the numerical value BB as the latter of "AA to BB" as the upper limit value.

The compound of the present invention will be described below.

The compound of the present invention is represented by the following formula (1). Hereinafter, the compound of the present invention that is represented by the formula (1) or each formula described later is sometimes simply referred to as "inventive compound".

(1)

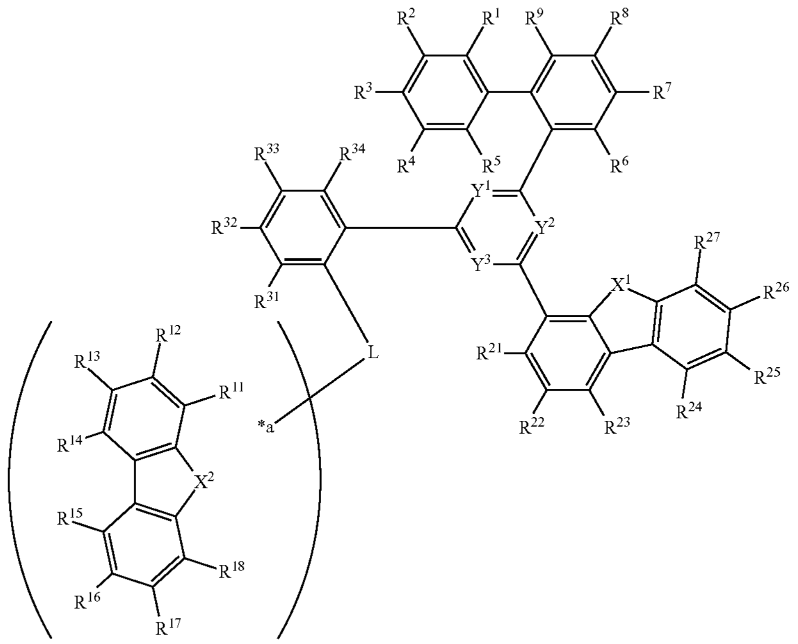

Hereinafter, signs in the formula (1) and formulas shown later will be described. Unless otherwise specified, the same sign has the same meaning.

$R^1$ to $R^9$ are each independently selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a cyano group, preferably selected from a hydrogen atom, a substituted or unsubstituted alkyl group having 1 to 50 carbon atoms, and a substituted or unsubstituted aryl group having 6 to 50 ring carbon atoms, and more preferably is a hydrogen atom. All of $R^1$ to $R^9$ may be a hydrogen atom.

Details of the substituted or unsubstituted alkyl group having 1 to 50 carbon atoms represented by $R^1$ to $R^9$ are as described in the section of "Substituents in Description".

The unsubstituted alkyl group is preferably a methyl group, an ethyl group, an n-propyl group, an isopropyl group, an n-butyl group, an isobutyl group, an s-butyl group, a t-butyl group, or an n-pentyl group, more preferably a methyl group, an ethyl group, an isopropyl group, or a t-butyl group, and further preferably a methyl group or a t-butyl group.

Details of the substituted or unsubstituted cycloalkyl group having 3 to 50 ring carbon atoms represented by $R^1$ to $R^9$ are as described in the section of "Substituents in Description".

The unsubstituted cycloalkyl group is preferably a cyclopropyl group, a cyclobutyl group, a cyclopentyl group, a cyclohexyl group, an adamantyl group, or a norbornyl group.

Details of the substituted or unsubstituted aryl group having 6 to 50 ring carbon atoms represented by $R^1$ to $R^9$ are as described in the section of "Substituents in Description".

The unsubstituted aryl group is preferably a phenyl group, a biphenylyl group, a terphenylyl group, a naphthyl group, an anthryl group, a phenanthryl group, a phenalenyl group, a pyrenyl group, a chrysenyl group, a triphenylenyl group, a tetracenyl group, a pentacenyl group, a fluorenyl group, a fluoranthenyl group, a perylenyl group, or a 9,9'-spirobifluorenyl group, more preferably a phenyl group, a biphenylyl group, a terphenylyl group, a naphthyl group, or a phenanthryl group, further preferably a phenyl group, a biphenylyl group, or a naphthyl group, and particularly preferably a phenyl group.

The substituted aryl group is preferably a 9,9-dimethylfluorenyl group and a 9,9-diphenylfluorenyl group.

Details of the substituted or unsubstituted heterocyclic group having 5 to 50 ring atoms represented by $R^1$ to $R^9$ are as described in the section of "Substituents in Description".

The unsubstituted heterocyclic group is preferably a pyridyl group, a pyrimidinyl group, a triazinyl group, a quinolyl group, an isoquinolyl group, a quinazolinyl group, a benzimidazolyl group, a phenanthrolinyl group, a carbazolyl group (1-carbazolyl group, 2-carbazolyl group, 3-carbazolyl group, 4-carbazolyl group, or 9-carbazolyl group), a benzocarbazolyl group, a dibenzofuranyl group, a naphthobenzofuranyl group, a dibenzothiophenyl group, or a naphthobenzothiophenyl group, more preferably a pyridyl group, a pyrimidinyl group, a carbazolyl group, a dibenzofuranyl group, a naphthobenzofuranyl group, or a dibenzothiophenyl group, and further preferably a pyridyl group, a carbazolyl group, a dibenzofuranyl group, a naphthobenzofuranyl group, or a dibenzothiophenyl group.

The substituted heterocyclic group is preferably a 9-phenylcarbazolyl group (9-phenylcarbazol-1-yl group, 9-phenylcarbazol-2-yl group, 9-phenylcarbazol-3-yl group, or 9-phenylcarbazol-4-yl group), a diphenylcarbazol-9-yl group, or a phenylcarbazol-9-yl group.

In one or more pairs selected from $R^1$ and $R^2$, $R^2$ and $R^3$, $R^3$ and $R^4$, $R^4$ and $R^5$, $R^6$ and $R^7$, $R^7$ and $R^8$, and $R^8$ and $R^9$, the adjacent two may bind to each other to form a substituted or unsubstituted ring structure, or may not bind to each other and thus not form a ring structure.

The substituted or unsubstituted ring structure is, for example, selected from a substituted or unsubstituted aromatic hydrocarbon ring, a substituted or unsubstituted aliphatic hydrocarbon ring, a substituted or unsubstituted aromatic heteroring, and a substituted or unsubstituted aliphatic heteroring.

The aromatic hydrocarbon ring is, for example, a benzene ring, a biphenylene ring, a naphthalene ring, an anthracene ring, a benzanthracene ring, a phenanthrene ring, a benzophenanthrene ring, a phenalene ring, a pyrene ring, a chrysene ring, a 1,1-dimethylindene ring, or a triphenylene ring, preferably a benzene ring or a naphthalene ring, and more preferably a benzene ring.

The aliphatic hydrocarbon ring is, for example, a cyclopentene ring, a cyclopentadiene ring, a cyclohexene ring, a cyclohexadiene ring, or an aliphatic hydrocarbon ring obtained by partially hydrogenating the aforementioned aromatic hydrocarbon ring.

The aromatic heteroring is, for example, a pyrrole ring, a furane ring, a thiophene ring, a pyridine ring, an imidazole ring, a pyrazole ring, an indole ring, an isoindole ring, a benzofuran ring, an isobenzofuran ring, a benzothiophene ring, a benzimidazole ring, an indazole ring, a dibenzofuran ring, a naphthobenzofuran ring, a dibenzothiophene ring, a naphthobenzothiophene ring, a carbazole ring, or a benzocarbazole ring.

The aliphatic heteroring is, for example, an aliphatic heteroring obtained by partially hydrogenating the aforementioned aromatic heteroring.

In an aspect of the present invention, in one pair selected from $R^1$ and $R^2$, $R^2$ and $R^3$, $R^7$ and $R^8$, and $R^8$ and $R^9$, the adjacent two preferably bind to each other to form a benzene ring.

$R^1$ and $R^9$ may bind to each other to form —$CR^aR^b$— that crosslinks two benzene rings, or may not bind to each other. Accordingly the inventive compound includes a compound represented by the following formula (1a) or (1b).

(1a)

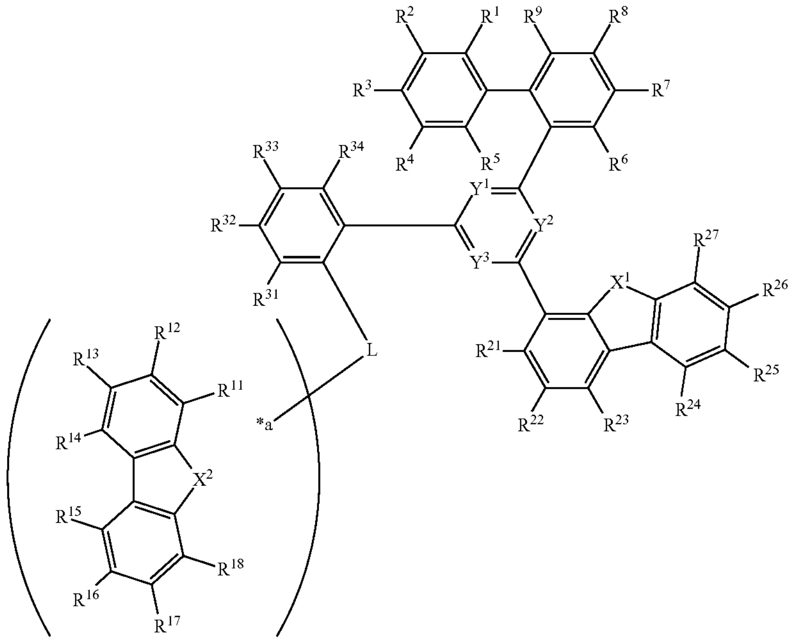

(In the formula, $R^1$ and $R^9$ do not bind to each other.)

(1b)

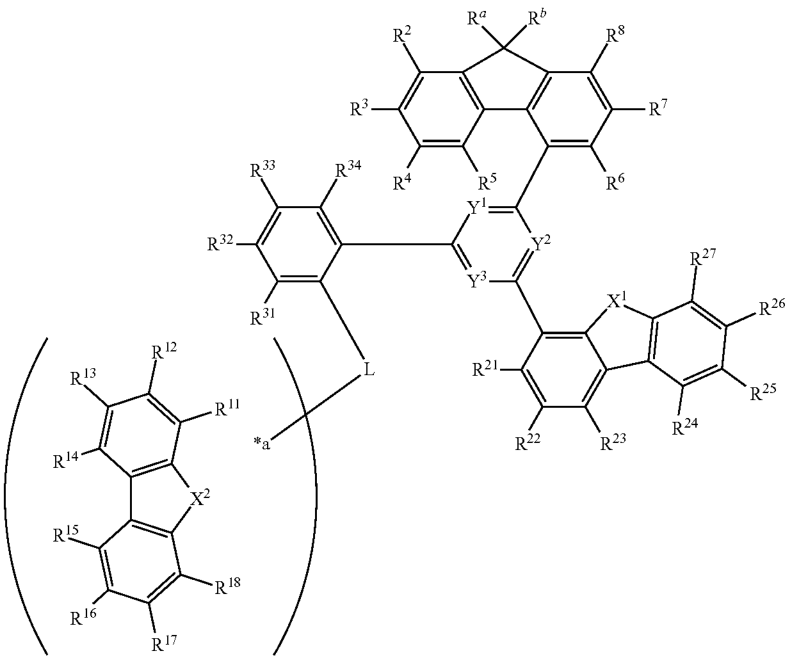

Details of $R^1$ to $R^9$ in the case where $R^1$ and $R^9$ do not bind to each other are as described above, and all of $R^1$ to $R^9$ may be a hydrogen atom.

Details of $R^2$ to $R^8$ in the case where $R^1$ and $R^9$ bind to each other to form —$CR^aR^b$— that crosslinks two benzene rings are as described above, and all of $R^2$ to $R^8$ may be a hydrogen atom.

$R^a$ and $R^b$ are each independently selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a cyano group. Preferably $R^a$ and $R^b$ are each independently selected from a substituted or unsubstituted alkyl group having 1 to 50 carbon atoms and a substituted or unsubstituted aryl group having 6 to 50 ring carbon atoms.

Details of the substituted or unsubstituted alkyl group having 1 to 50 carbon atoms represented by $R^a$ and $R^b$, the substituted or unsubstituted cycloalkyl group having 3 to 50 ring carbon atoms, the substituted or unsubstituted aryl group having 6 to 50 ring carbon atoms, and the substituted or unsubstituted heterocyclic group having 5 to 50 ring atoms are as described above for the respective groups represented by $R^1$ to $R^9$.

The structure represented by the formula (10) of the inventive compound:

(10)

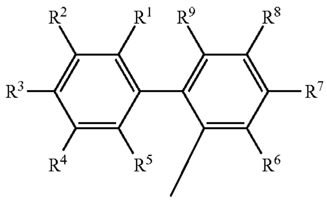

is preferably selected from the following groups.

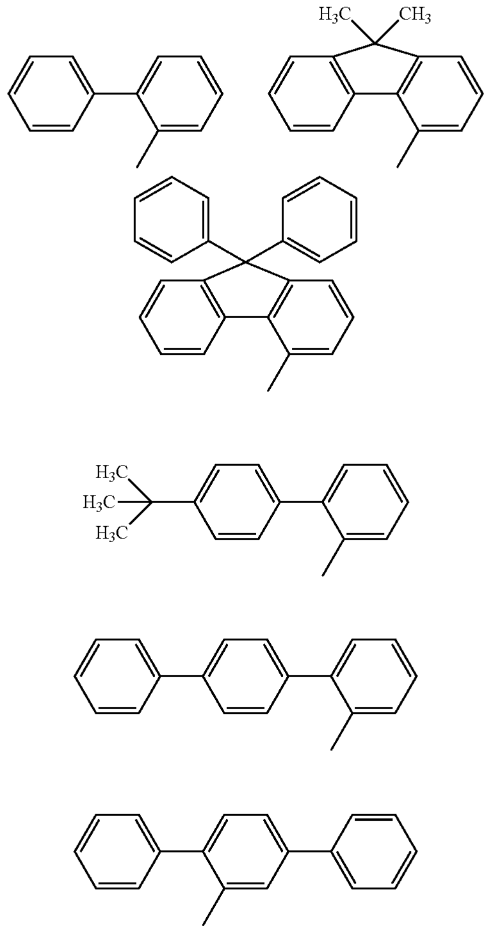

-continued

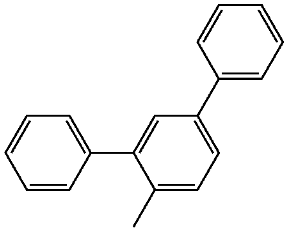

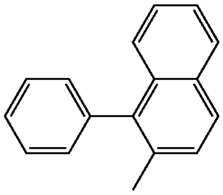

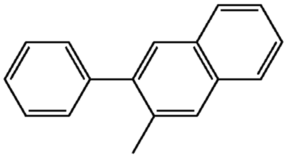

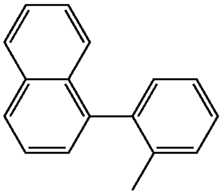

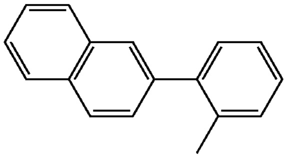

The structure represented by the formula (10) is more preferably selected from the following groups.

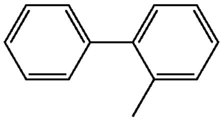

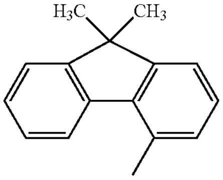

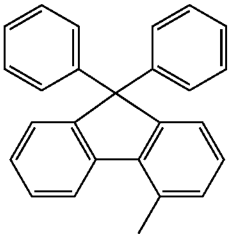

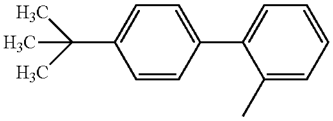

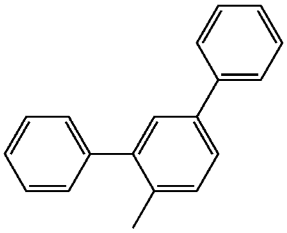

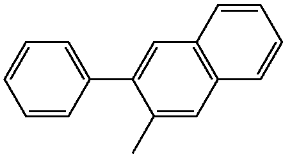

-continued

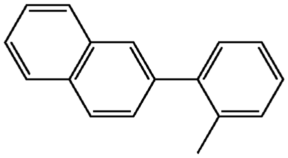

The structure represented by the formula (10) is further preferably selected from the following groups.

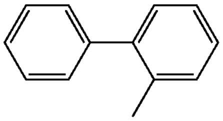

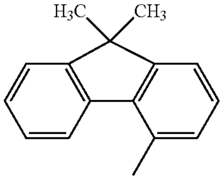

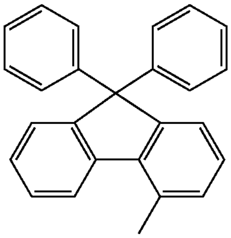

Two selected from $Y^1$ to $Y^3$ are a nitrogen atom and the remaining one is CR, or all of $Y^1$ to $Y^3$ are a nitrogen atom, and preferably all of $Y^1$ to $Y^3$ are a nitrogen atom. Accordingly the inventive compound includes a compound represented by any one of the following formulae (2a) to (2d).

(2a)

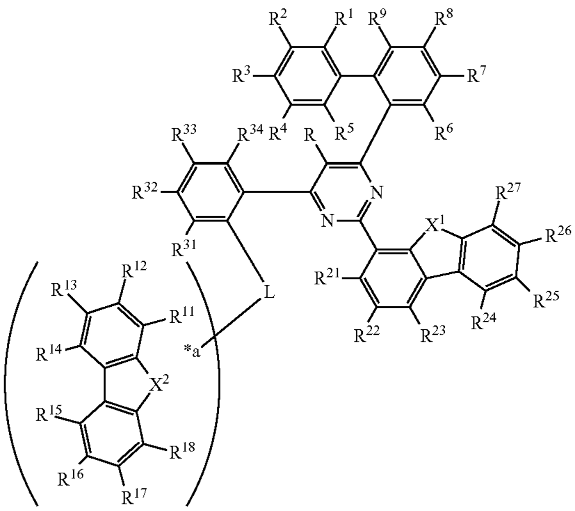

-continued (2b)

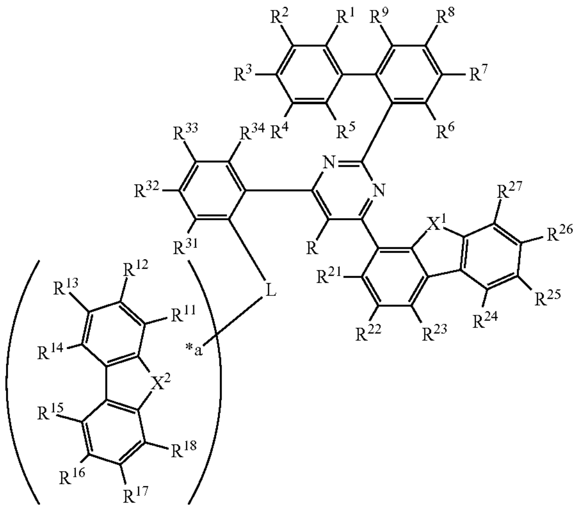

-continued (2d)

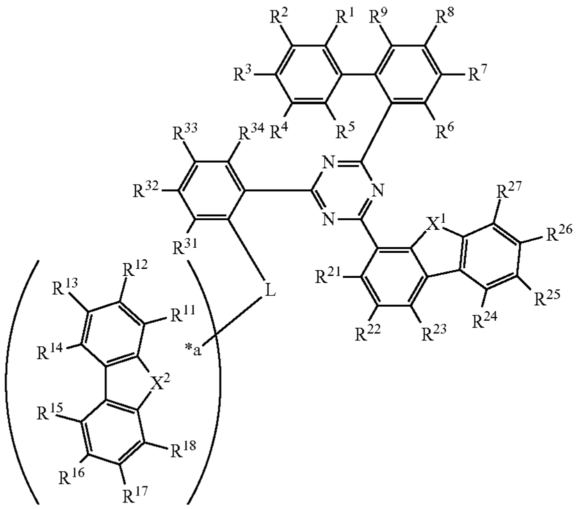

(2c)

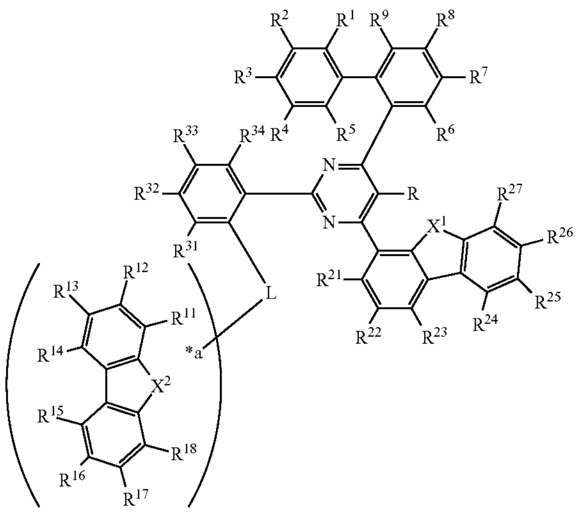

R is selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a cyano group. Preferably R is selected from a hydrogen atom, a substituted or unsubstituted alkyl group having 1 to 50 carbon atoms, and a substituted or unsubstituted aryl group having 6 to 50 ring carbon atoms, and more preferably is a hydrogen atom.

Details of the substituted or unsubstituted alkyl group having 1 to 50 carbon atoms, the substituted or unsubstituted cycloalkyl group having 3 to 50 ring carbon atoms, the substituted or unsubstituted aryl group having 6 to 50 ring carbon atoms, and the substituted or unsubstituted heterocyclic group having 5 to 50 ring atoms represented by R are as described above for the respective groups represented by $R^1$ to $R^9$.

$X^1$ is an oxygen atom or a sulfur atom, and preferably a sulfur atom. Accordingly the inventive compound includes a compound represented by the following formula (3a) or (3b).

(3a)

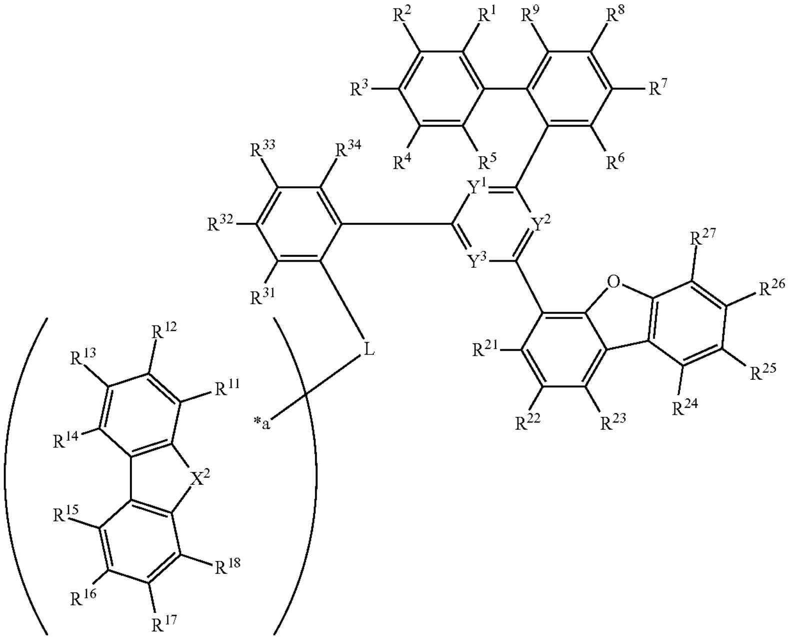

(3b)

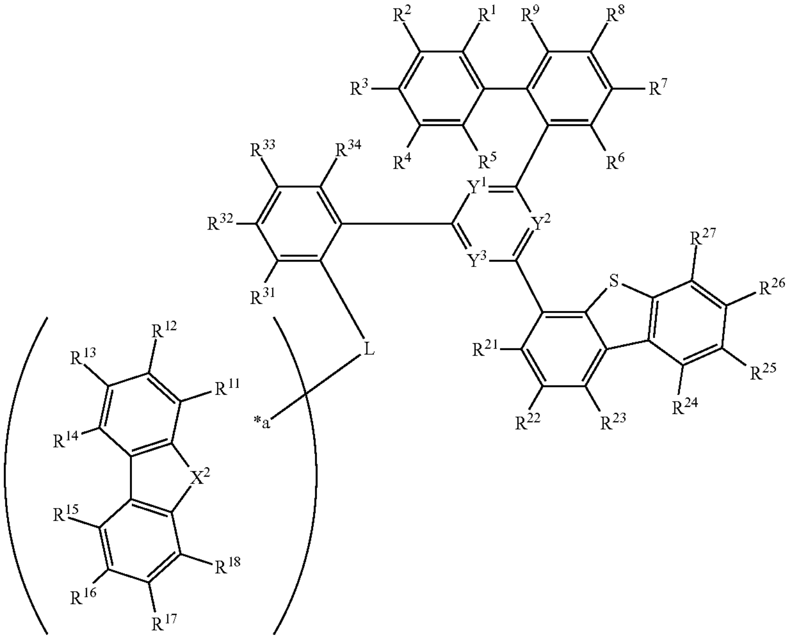

$R^{21}$ to $R^{27}$ are a hydrogen atom.

$R^{31}$ to $R^{34}$ are each independently selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a cyano group, preferably selected from a hydrogen atom, a substituted or unsubstituted alkyl group having 1 to 50 carbon atoms, and a substituted or unsubstituted aryl group having 6 to 50 ring carbon atoms, and more preferably is a hydrogen atom. All of $R^{31}$ to $R^{34}$ may be a hydrogen atom.

Details of the substituted or unsubstituted alkyl group having 1 to 50 carbon atoms, the substituted or unsubstituted cycloalkyl group having 3 to 50 ring carbon atoms, the substituted or unsubstituted aryl group having 6 to 50 ring carbon atoms, and the substituted or unsubstituted heterocyclic group having 5 to 50 ring atoms represented by $R^{31}$ to $R^{34}$ are the same as the details of the respective groups described above for $R^1$ to $R^9$.

In one or more pairs selected from $R^{31}$ and $R^{32}$, $R^{32}$ and $R^{33}$, and $R^{33}$ and $R^{34}$, the adjacent two may bind to each other to form a substituted or unsubstituted ring structure, or may not bind to each other and thus not form a ring structure.

Details of the substituted or unsubstituted ring structure are the same as the details of the substituted or unsubstituted ring structure that the adjacent two, in one or more pairs selected from $R^1$ and $R^2$, $R^2$ and $R^3$, $R^3$ and $R^4$, $R^4$ and $R^5$, $R^6$ and $R^7$, $R^7$ and $R^8$, and $R^8$ and $R^9$, bind to each other to optionally form.

L is selected from a single bond, a substituted or unsubstituted arylene group having 6 to 50 ring carbon atoms, and a substituted or unsubstituted divalent heterocyclic group having 5 to 30 ring carbon atoms, preferably a single bond or a substituted or unsubstituted arylene group having 6 to 50 ring carbon atoms, and more preferably a single bond. Accordingly the inventive compound includes a compound represented by the following formula (4a) or (4b).

(4a)

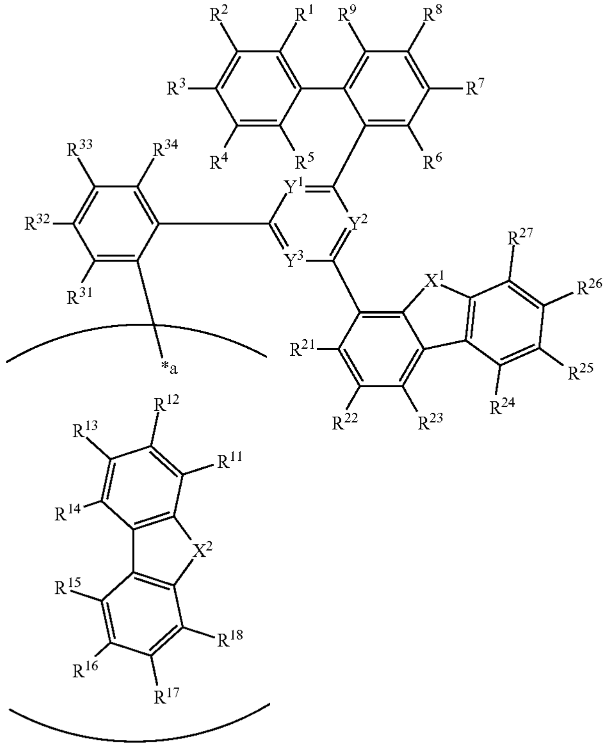

(4b)

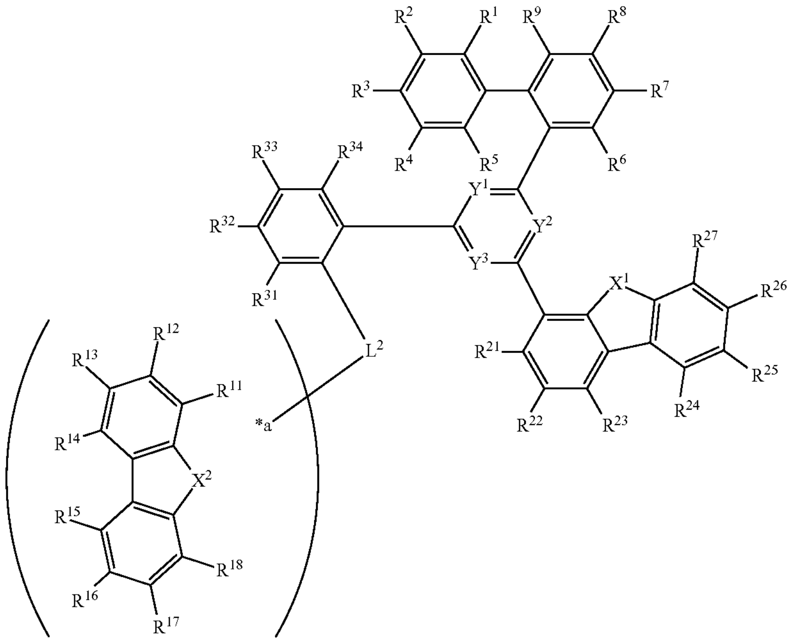

(In the formula, $L^2$ is a substituted or unsubstituted arylene group having 6 to 50 ring carbon atoms or a substituted or unsubstituted divalent heterocyclic group having 5 to 30 ring carbon atoms.)

Details of the substituted or unsubstituted arylene group having 6 to 50 ring carbon atoms represented by L or $L^2$ are as described in the section of "Substituents in Description".

The unsubstituted arylene group is preferably a divalent group derived from a group selected from a phenyl group, a biphenylyl group, a terphenylyl group, a naphthyl group, a phenanthryl group, a pyrenyl group, a chrysenyl group, a triphenylenyl group, a fluorenyl group, and a 9,9'-spirobifluorenyl group by removing one hydrogen atom on an aromatic hydrocarbon ring, more preferably a phenylene group, a biphenylylene group, or a naphthylene group, further preferably a p-phenylene group, a m-phenylene group, a p-biphenyl-4,4'-diyl group, a p-biphenyl-3,5-diyl group, a p-biphenyl-3,3'-diyl group, or a p-biphenyl-3,4'-diyl group, and particularly preferably a p-phenylene group.

As a substituent of the arylene group, a dibenzofuranyl group, a dibenzothiophenyl group, a carbazolyl group, or a 9,9-dimethylfluorenyl group is preferred, and a 2- or 4-dibenzofuranyl group, a 2- or 4-dibenzothiophenyl group, or a 2-9,9-dimethylfluorenyl group is more preferred.

Details of the substituted or unsubstituted divalent heterocyclic group having 5 to 30 ring carbon atoms represented by L or $L^2$ are as described in the section of "Substituents in Description".

The unsubstituted divalent heterocyclic group is preferably a divalent group derived from a heterocyclic group selected from a pyridyl group, a pyrimidinyl group, a triazinyl group, a quinolyl group, an isoquinolyl group, a quinazolinyl group, a benzimidazolyl group, a phenanthrolinyl group, a carbazolyl group (1-carbazolyl group, 2-carbazolyl group, 3-carbazolyl group, 4-carbazolyl group, or 9-carbazolyl group), a benzocarbazolyl group, a dibenzofuranyl group, a naphthobenzofuranyl group, a dibenzothiophenyl group, and naphthobenzothiophenyl group by removing one hydrogen atom on a heteroring or hydrocarbon ring, more preferably a divalent group derived from a monovalent heterocyclic group selected from a pyridyl group, a dibenzofuranyl group, and a dibenzothiophenyl group by removing one hydrogen atom on a heteroring or a hydrocarbon ring.

Examples of the substituted divalent heterocyclic group include a divalent group derived from a 9-phenylcarbazolyl group (9-phenylcarbazol-1-yl group, 9-phenylcarbazol-2-yl group, 9-phenylcarbazol-3-yl group, or 9-phenylcarbazol-4-yl group), a diphenylcarbazol-9-yl group, or a phenylcarbazol-9-yl group by removing one hydrogen atom on a hydrocarbon ring.

One of $R^{11}$ to $R^{14}$ is a single bond binding to *a, and $R^{11}$ to $R^{14}$ that are not a single bond binding to *a and $R^{15}$ to $R^{18}$ are a hydrogen atom. Accordingly the inventive compound includes a compound represented by any one of the following formulae (5a) to (5d).

(5a)

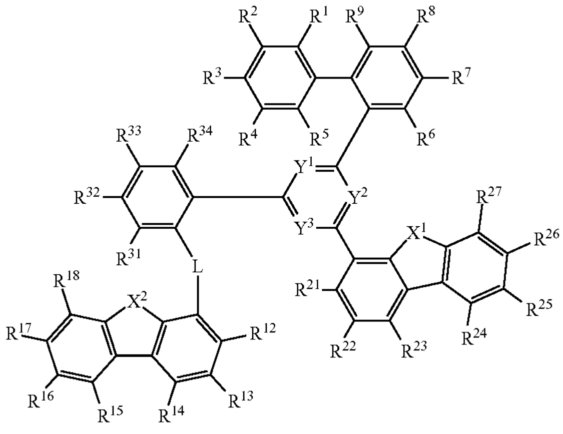

(5b)

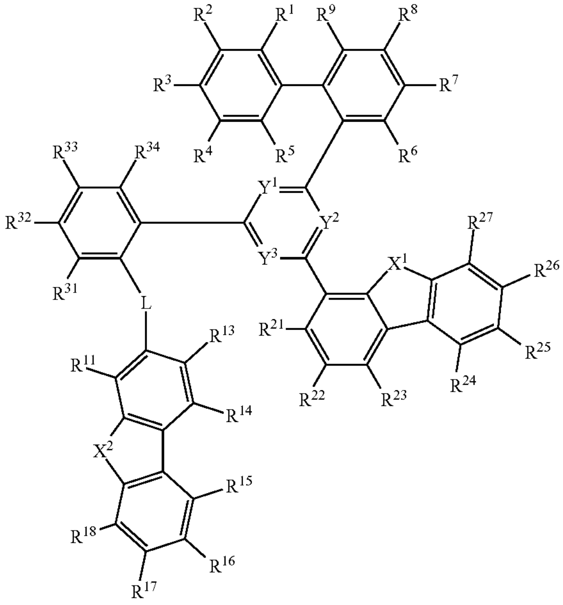

(5c)

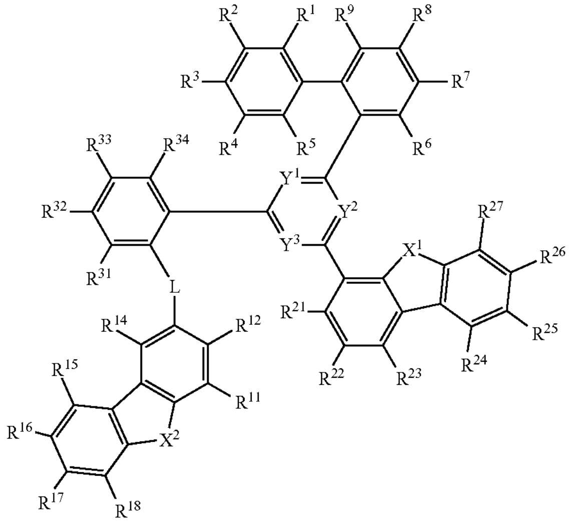

-continued (5d)

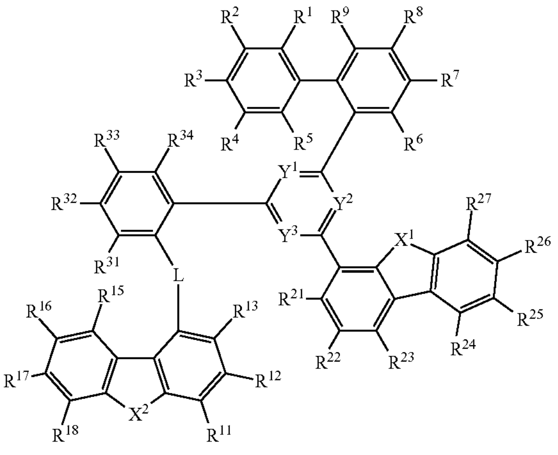

$X^2$ is selected from an oxygen atom, a sulfur atom, $NR^A$, and $CR^BR^C$, preferably is an oxygen atom or a sulfur atom, and more preferably is a sulfur atom. Accordingly the inventive compound includes a compound represented by any one of the following formulae (6a) to (6d).

(6a)

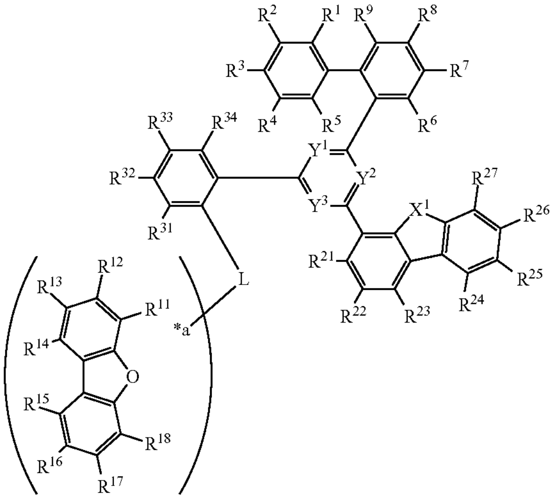

-continued (6b)

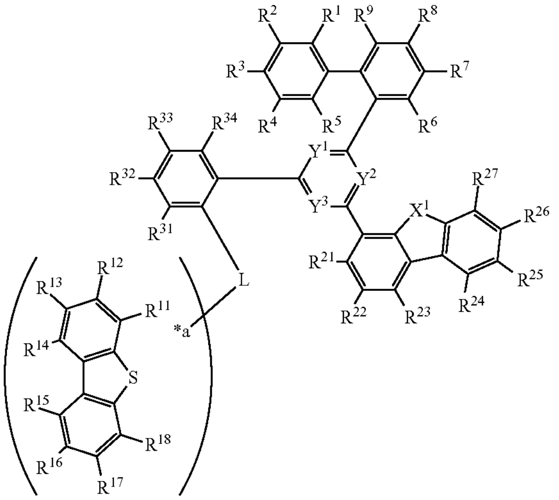

(6c)

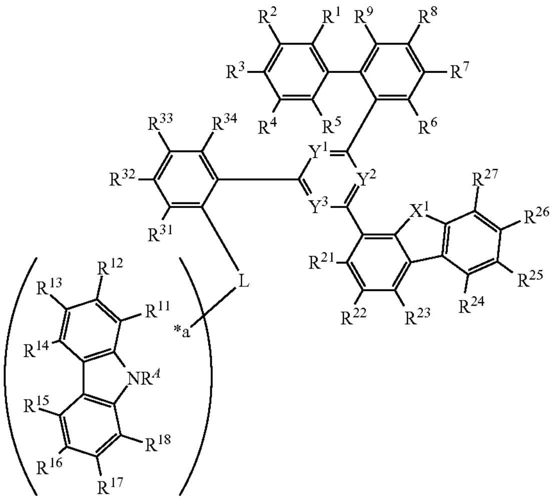

(6d)

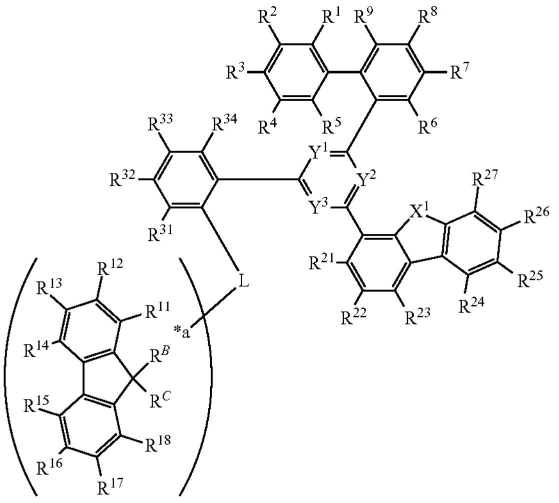

$R^A$ is selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms.

Details of the substituted or unsubstituted alkyl group having 1 to 50 carbon atoms, the substituted or unsubstituted cycloalkyl group having 3 to 50 ring carbon atoms, the substituted or unsubstituted aryl group having 6 to 50 ring carbon atoms, and the substituted or unsubstituted heterocyclic group having 5 to 50 ring atoms represented by $R^A$ are as described above for the respective groups represented by $R^1$ to $R^9$.

$R^A$ is preferably a substituted or unsubstituted aryl group having 6 to 50 ring carbon atoms, and more preferably a phenyl group.

$R^B$ and $R^C$ are each independently selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a cyano group.

Details of the substituted or unsubstituted alkyl group having 1 to 50 carbon atoms, the substituted or unsubstituted cycloalkyl group having 3 to 50 ring carbon atoms, the substituted or unsubstituted aryl group having 6 to 50 ring carbon atoms, and a substituted or unsubstituted heterocyclic group having 5 to 50 ring atoms represented by $R^B$ and $R^C$ are as described above for the respective groups represented by $R^1$ to $R^9$.

Preferably $R^B$ and $R^C$ are each independently selected from a substituted or unsubstituted alkyl group having 1 to 50 carbon atoms and a substituted or unsubstituted aryl group having 6 to 50 ring carbon atoms. More preferably $R^B$ and $R^C$ are each independently selected from a methyl group, an ethyl group, and a phenyl group, and further preferably are selected from a methyl group and phenyl group.

When $R^B$ and $R^C$ are each independently a substituted or unsubstituted aryl group having 6 to 50 ring carbon atoms, the two aryl groups may be crosslinked via —O— or —S—. Accordingly the inventive compound includes a compound represented by the following formula (7).

(7)

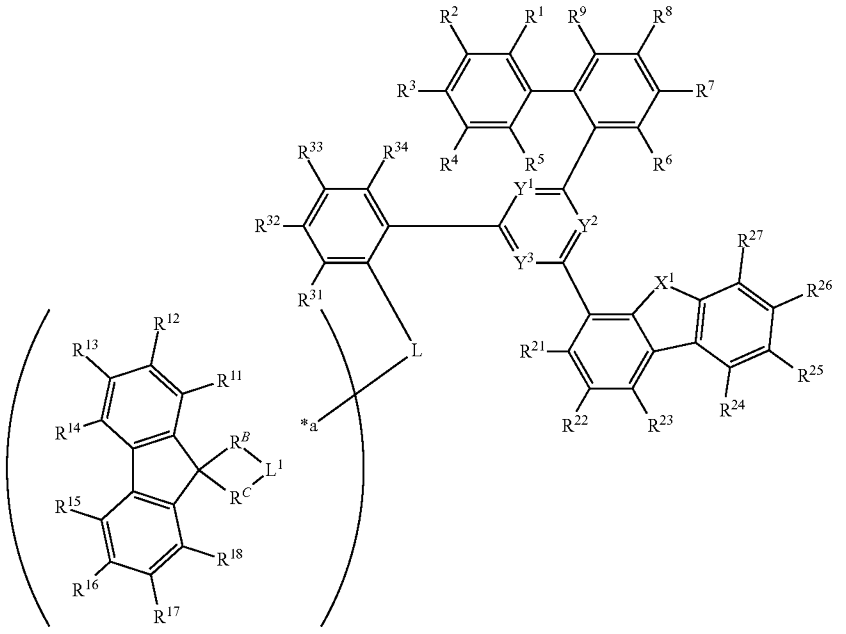

(In the formula, $R^B$ and $R^C$ are each independently a substituted or unsubstituted aryl group having 6 to 50 ring carbon atoms, and $L^1$ is an oxygen atom or a sulfur atom.)

$R^B$ and $R^C$ in the formula (7) are preferably each independently a substituted or unsubstituted phenyl group. In this case, $R^B$ and $R^C$ form a xanthene ring or a thioxanthene ring that forms a spiro-structure together with a spiro-carbon atom and $L^1$. Accordingly the compound represented by the formula (7) includes a compound represented either of the following formulae (7a) and (7b).

(7a)
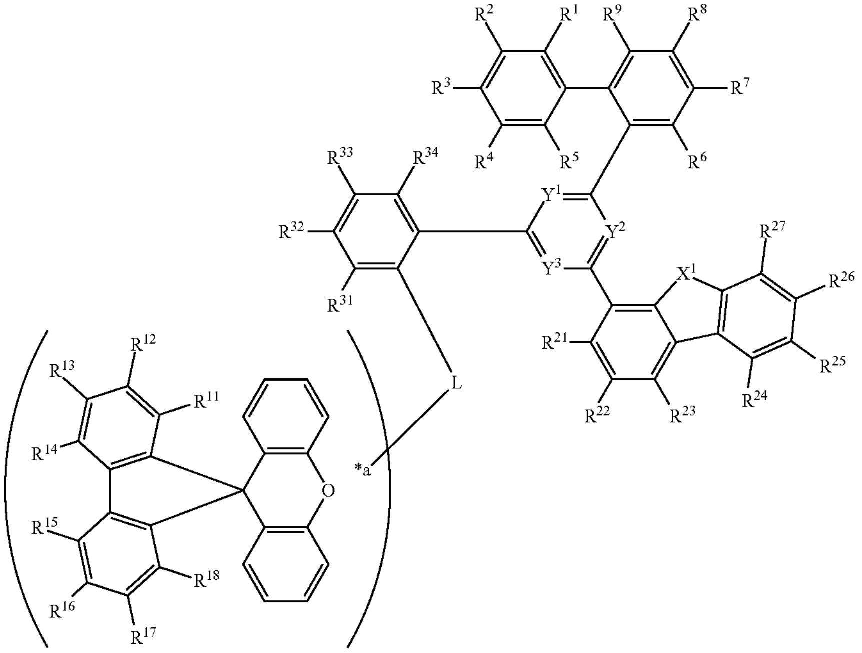
(7b)
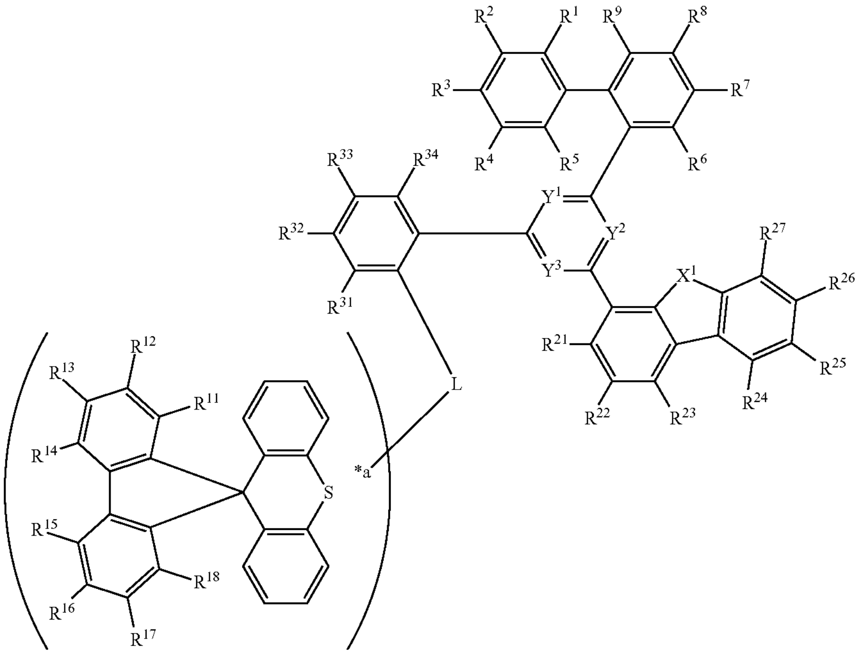
In an aspect of the present invention, the inventive compound is preferably represented by the following formula (13).

(13)
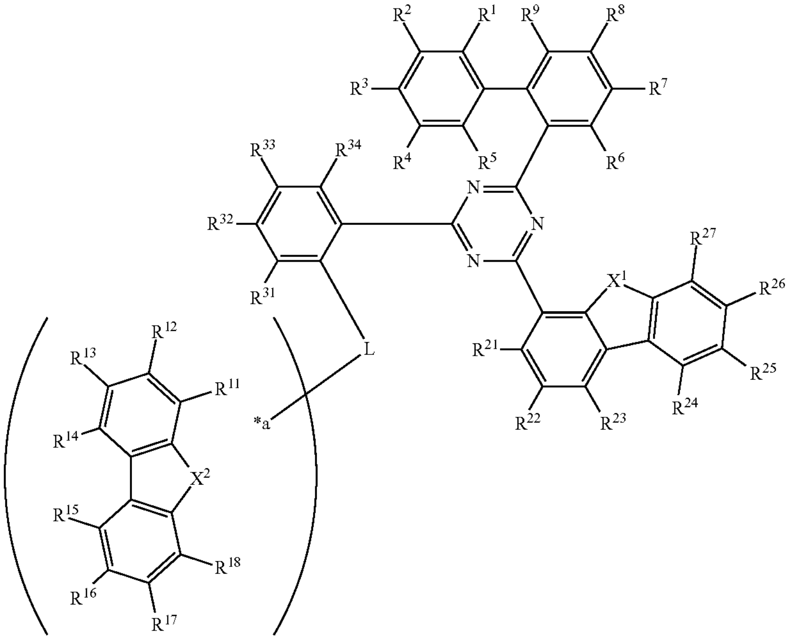
(In the formula, $X^1$, $X^2$, L, *a, $R^1$ to $R^9$, $R^{11}$ to $R^{18}$, and $R^{21}$ to $R^{27}$ are as defined for the formula (1), provided that $R^1$ and $R^9$ do not bind to each other.)
In another aspect of the present invention, the inventive compound is preferably represented by the following formula (14a) or (14b).
(14a)
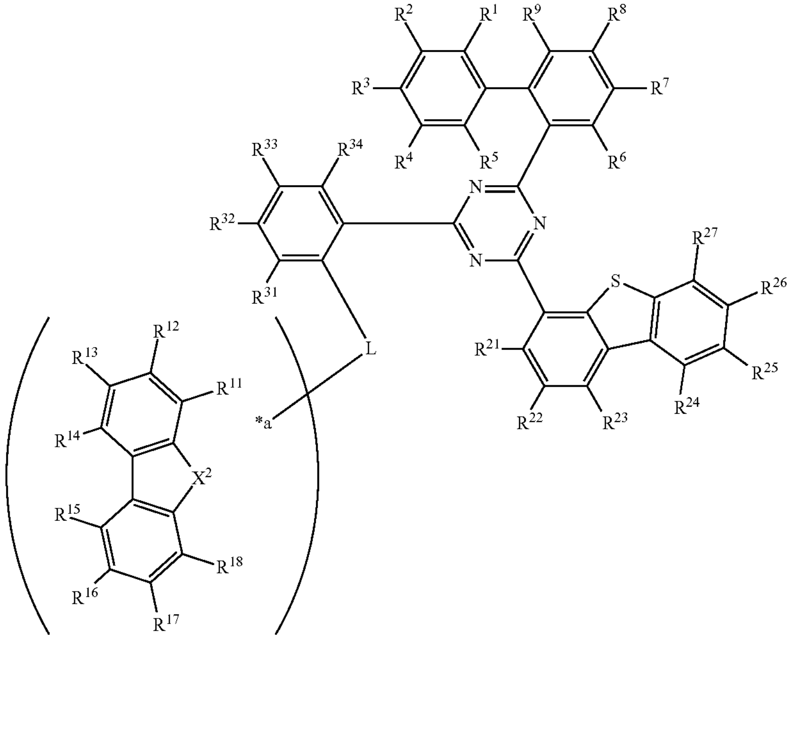

-continued
(14b)
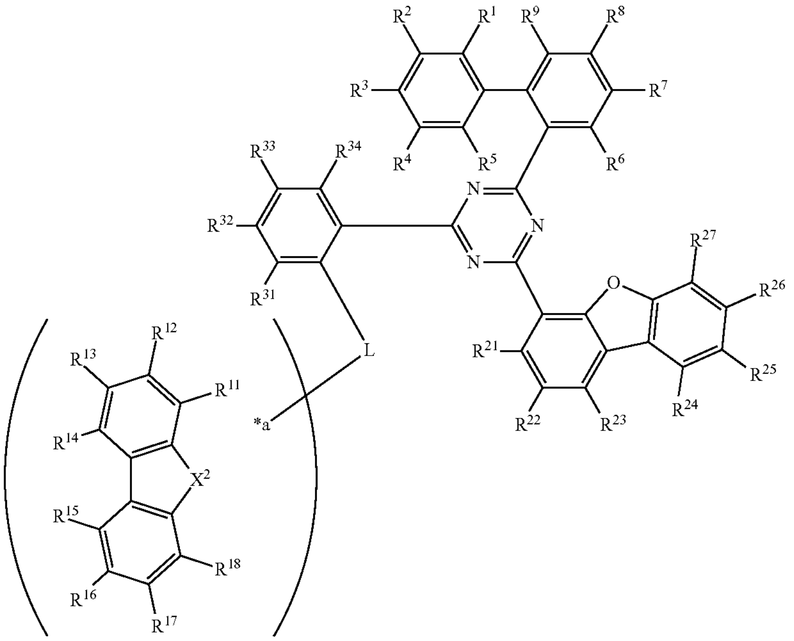
(In the formula, $X^2$, L, *a, $R^1$ to $R^9$, $R^{11}$ to $R^{18}$, and $R^{21}$ to $R^{27}$ are as defined for the formula (1).)
In another aspect of the present invention, the inventive compound is preferably represented by any one of the following formulae (15) to (18).
(15)
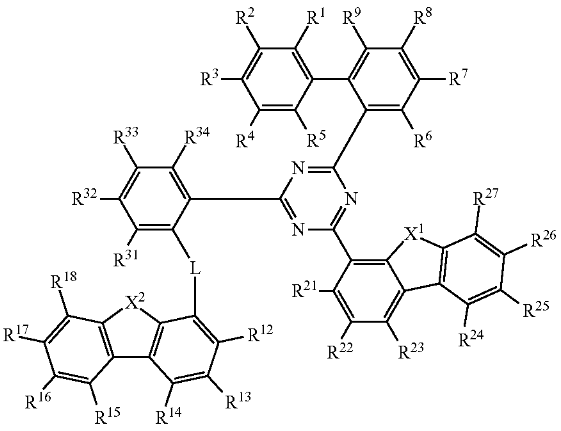
-continued
(16)
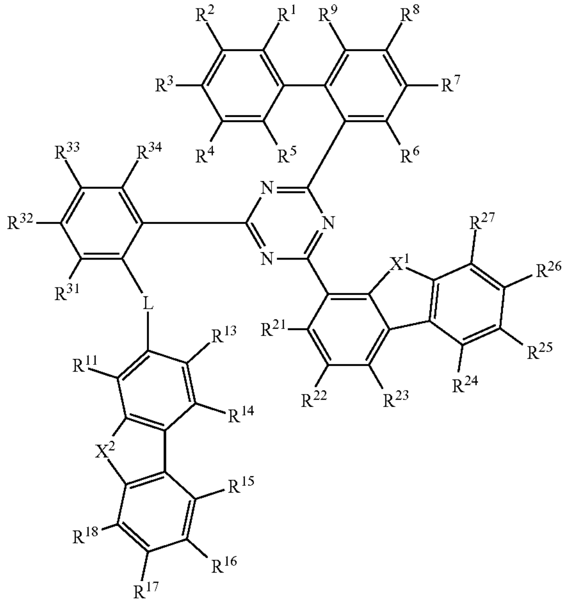

-continued
(17)
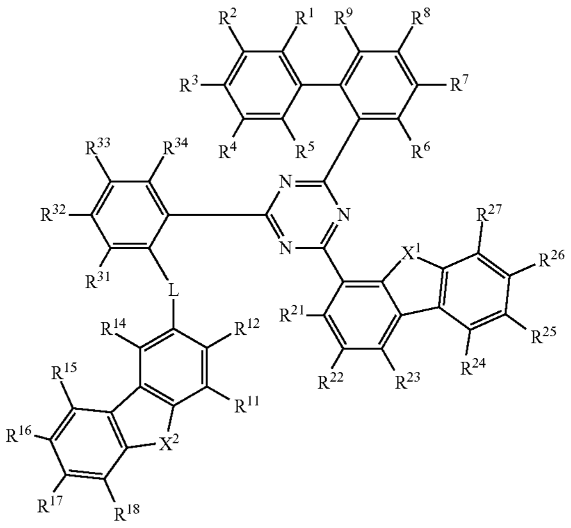
-continued
(18)
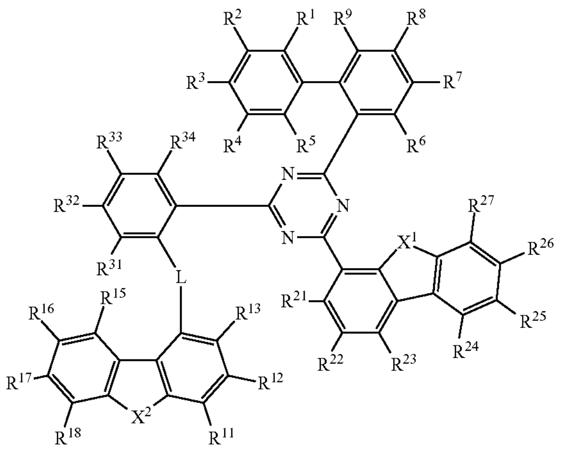
(In the formula, $X^1$, $X^2$, L, $R^1$ to $R^9$, $R^{11}$ to $R^{18}$, and $R^{21}$ to $R^{27}$ are as defined for the formula (1).)
In another aspect of the present invention, the inventive compound is preferably represented by the following formula (19).
(19)
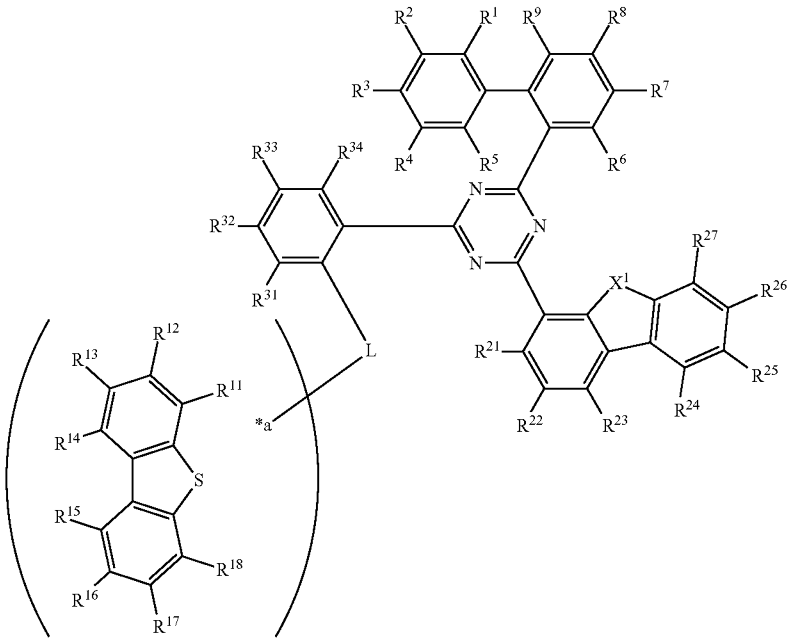

(In the formula, $X^1$, L, *a, $R^1$ to $R^9$, $R^{11}$ to $R^{18}$, and $R^{21}$ to $R^{27}$ are as defined for the formula (1).)

In another aspect of the present invention, the inventive compound is preferably represented by the following formula (20).

(20)

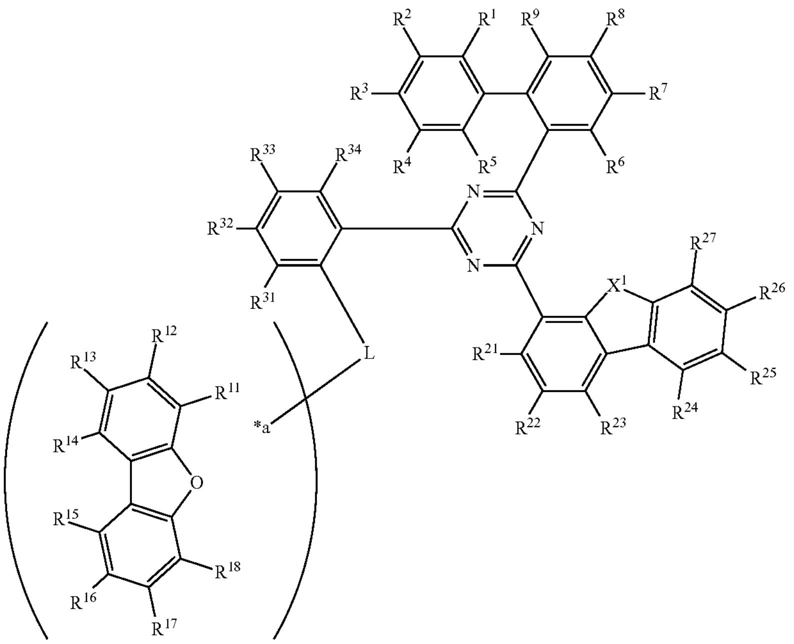

In another aspect of the present invention, the inventive compound is preferably represented by the following formula (21).

(21)

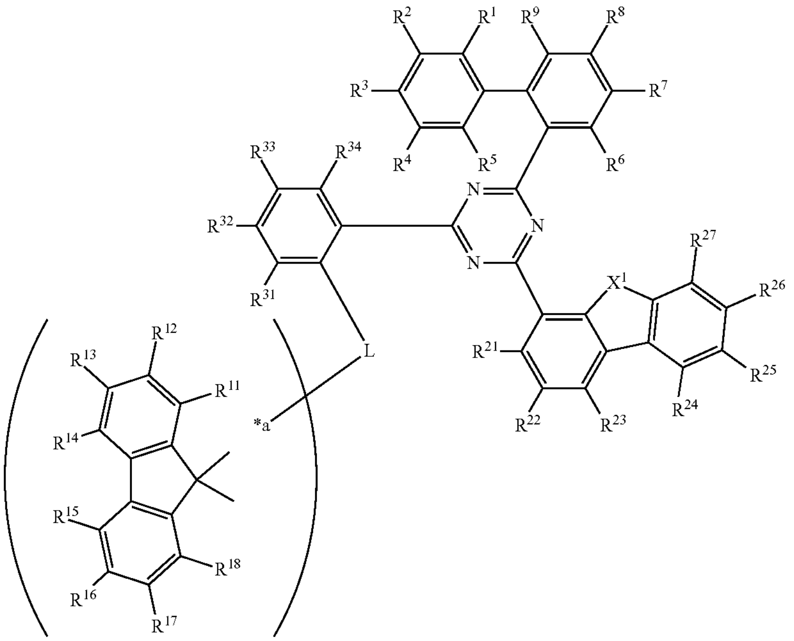

In another aspect of the present invention, the inventive compound is preferably represented by the following formula (22).

(22)
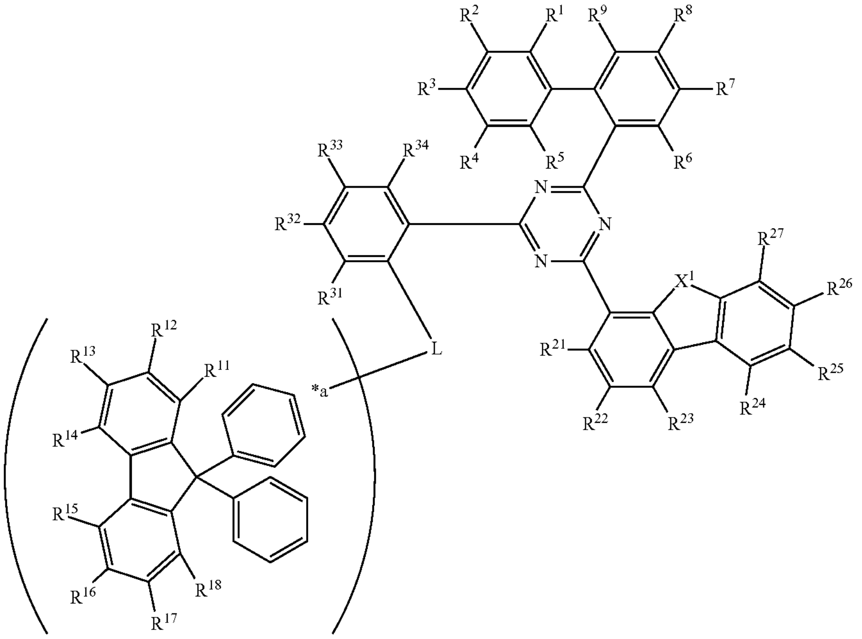
In another aspect of the present invention, the inventive compound is preferably represented by the following formula (23).
(23)
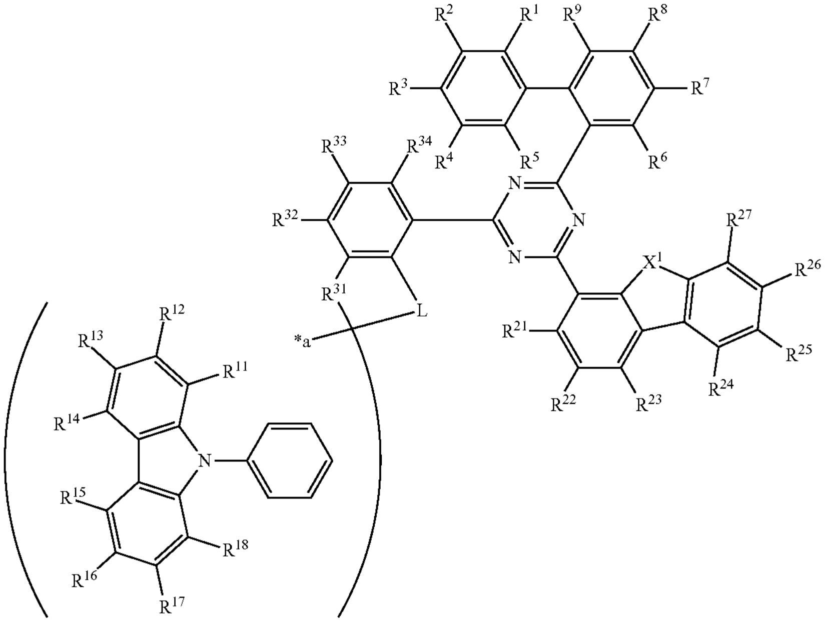
In another aspect of the present invention, the inventive compound is preferably represented by the following formula (24).

(24)

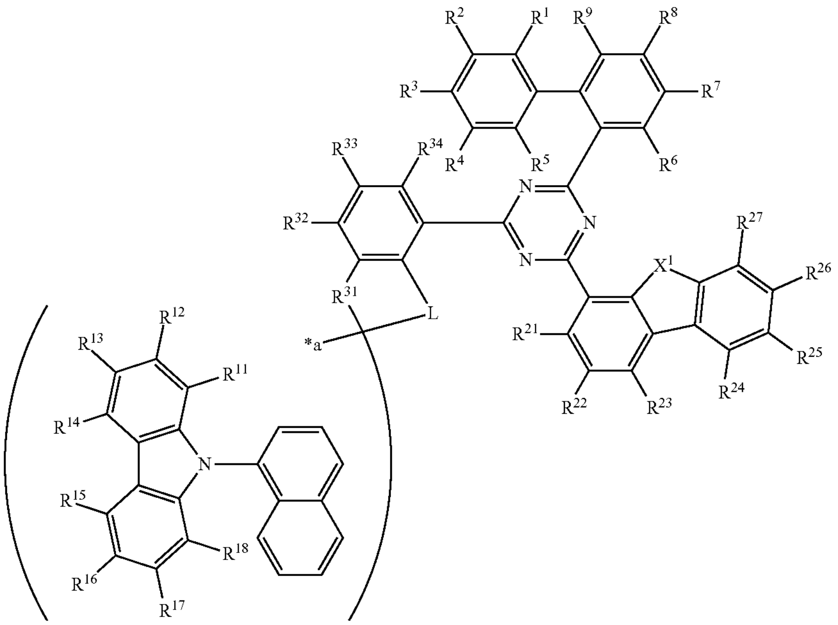

Details of the substituent (optional substituent) in the "substituted or unsubstituted" included in the definition of each group described above are as described in the section of "Substituent for "Substituted or Unsubstituted"".

As described above, the "hydrogen atom" used in this description includes a protium atom, a deuterium atom, and a tritium atom. Accordingly the inventive compound may contain a naturally occurring deuterium atom.

Alternatively a deuterium atom may be intentionally introduced into the inventive compound by using a compound obtained by deuterating a part or all of a raw material compound. Accordingly in an aspect of the present invention, the inventive compound contains at least one deuterium atom. In other words, the inventive compound may be a compound represented by the formula (1) in which at least one of the hydrogen atoms in the compound is a deuterium atom.

At least one hydrogen atom selected from hydrogen atoms represented by any of $R^1$ to $R^9$; hydrogen atoms of a substituted or unsubstituted alkyl group, cycloalkyl group, aryl group, or heterocyclic group represented by any of $R^1$ to $R^9$;

hydrogen atoms represented by any of $R^a$ and $R^b$; hydrogen atoms of a substituted or unsubstituted alkyl group, cycloalkyl group, aryl group, or heterocyclic group represented by any of $R^a$ and $R^b$;

a hydrogen atom represented by R; hydrogen atoms of a substituted or unsubstituted alkyl group, cycloalkyl group, aryl group, or heterocyclic group represented by R;

hydrogen atoms represented by $R^{21}$ to $R^{27}$;

hydrogen atoms of a substituted or unsubstituted arylene group or divalent heterocyclic group represented by L;

hydrogen atoms represented by $R^{11}$ to $R^{14}$ that are not a single bond binding to *a and $R^{15}$ to $R^{18}$;

a hydrogen atom represented by $R^A$; hydrogen atoms of a substituted or unsubstituted alkyl group, cycloalkyl group, aryl group, or heterocyclic group represented by $R^A$; and hydrogen atoms represented by any of $R^B$ and $R^C$; hydrogen atoms of a substituted or unsubstituted alkyl group, cycloalkyl group, aryl group, or heterocyclic group represented by any of $R^B$ and $R^C$ may be a deuterium atom.

The deuteration ratio of the inventive compound (the ratio of the number of deuterium atoms to the total number of hydrogen atoms in the compound of the present invention) depends on the deuteration ratios of the raw material compounds used. Since it is generally difficult to make the deuteration ratios of all the raw material compounds used into 100%, the deuteration ratio of the inventive compound is less than 100%.

The deuteration ratio of the inventive compound is 1% or more, preferably 3% or more, more preferably 5% or more, and further preferably 10% or more.

The inventive compound may be a mixture containing a deuterated compound (a compound in which a deuterium atom is intentionally introduced) and a non-deuterated compound or a mixture of two or more compounds having different deuteration ratios. The deuteration ratio of such a mixture (the number of deuterium atoms to the total number of hydrogen atoms in the inventive compound contained in the mixture) is 1% or more, preferably 3% or more, more preferably 5% or more, and further preferably 10% or more, and is less than 100%.

In the inventive compound, at least one hydrogen atom selected from hydrogen atoms represented by any of $R^1$ to $R^9$ and hydrogen atoms of a substituted or unsubstituted alkyl group, cycloalkyl group, aryl group, or heterocyclic group represented by any of $R^1$ to $R^9$ may be a deuterium atom. The deuteration ratio (the ratio of the number of deuterium atoms to the total number of hydrogen atoms of $R^1$ to $R^9$) is 1% or more, preferably 3% or more, more preferably 5% or more, and further preferably 10% or more, and is less than 100%.

In the inventive compound, at least one hydrogen atom selected from a hydrogen atom represented by R or hydrogen atoms of a substituted or unsubstituted alkyl group, cycloalkyl group, aryl group, or heterocyclic group represented by R may be a deuterium atom. The deuteration ratio (the ratio of the number of deuterium atoms to the total number of hydrogen atoms of R) is 1% or more, preferably 3% or more, more preferably 5% or more, and further preferably 10% or more, and is less than 100%.

In the inventive compound, at least one hydrogen atom selected from hydrogen atoms represented by $R^{21}$ to $R^{27}$ may be a deuterium atom. The deuteration ratio (the ratio of the number of deuterium atoms to the total number of hydrogen atoms of $R^{21}$ to $R^{27}$) is 1% or more, preferably 3% or more, more preferably 5% or more, and further preferably 10% or more, and is less than 100%.

In the inventive compound, at least one hydrogen atom selected from hydrogen atoms represented by $R^{31}$ to $R^{34}$ may be a deuterium atom. The deuteration ratio (the ratio of the number of deuterium atoms to the total number of hydrogen atoms of $R^{31}$ to $R^{34}$) is 1% or more, preferably 3% or more, more preferably 5% or more, and further preferably 10% or more, and is less than 100%.

In the inventive compound, at least one hydrogen atom selected from hydrogen atoms of a substituted or unsubstituted arylene group or divalent heterocyclic group represented by L may be a deuterium atom. The deuteration ratio (the ratio of the number of deuterium atoms to the total number of hydrogen atoms of L) is 1% or more, preferably 3% or more, more preferably 5% or more, and further preferably 10% or more, and is less than 100%.

In the inventive compound, at least one hydrogen atom selected from hydrogen atoms represented by $R^{11}$ to $R^{14}$ that are not a single bond binding to *a and $R^{15}$ to $R^{18}$ may be a deuterium atom. The deuteration ratio (the ratio of the number of deuterium atoms to the total number of hydrogen atoms of $R^{11}$ to $R^{14}$ that are not a single bond binding to *a and $R^{15}$ to $R^{18}$) is 1% or more, preferably 3% or more, more preferably 5% or more, and further preferably 10% or more, and is less than 100%.

In the inventive compound, at least one hydrogen atom selected from a hydrogen atom represented by $R^A$ or hydrogen atoms of a substituted or unsubstituted alkyl group, cycloalkyl group, aryl group, or heterocyclic group represented by $R^A$ may be a deuterium atom. The deuteration ratio (the ratio of the number of deuterium atoms to the total number of hydrogen atoms of $R^A$) is 1% or more, preferably 3% or more, more preferably 5% or more, and further preferably 10% or more, and is less than 100%.

In the inventive compound, at least one hydrogen atom selected from hydrogen atoms represented by any of $R^B$ and $R^C$ and hydrogen atoms of a substituted or unsubstituted alkyl group, cycloalkyl group, aryl group, or heterocyclic group represented by any of $R^B$ and $R^C$ may be a deuterium atom. The deuteration ratio (the ratio of the number of deuterium atoms to the total number of hydrogen atoms of $R^B$ and $R^C$) is 1% or more, preferably 3% or more, more preferably 5% or more, and further preferably 10% or more, and is less than 100%.

The inventive compound can be easily produced with reference to the following synthetic method and a known synthetic method by one skilled in the art.

Specific examples of the inventive compound are shown below, but the inventive compound is not limited to the following exemplified compounds.

In the following specific examples, D represents a deuterium atom.

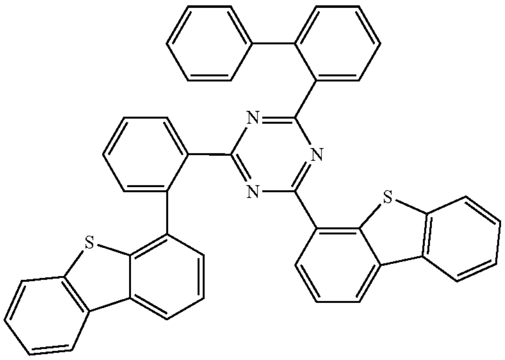

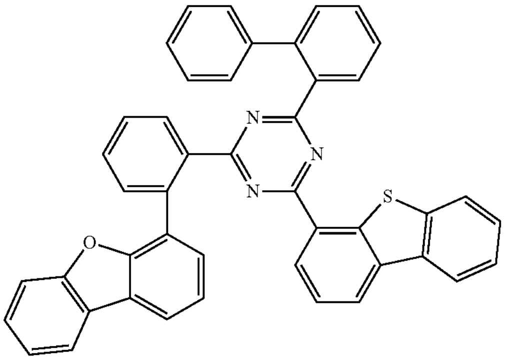

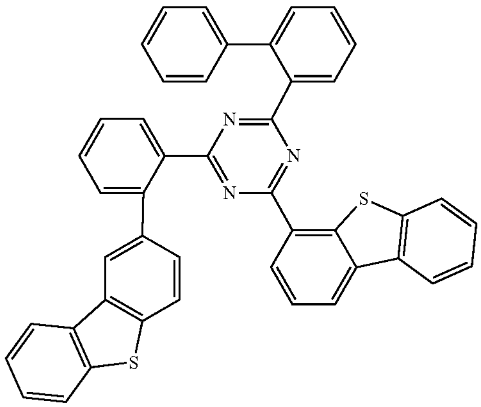

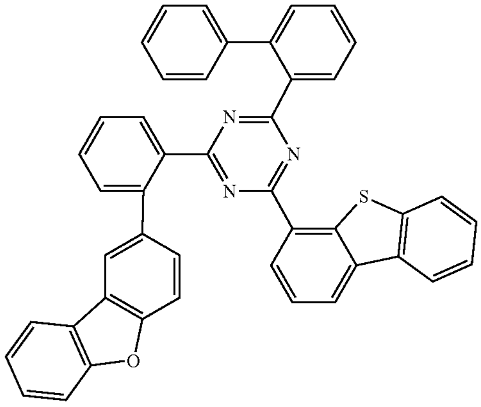

-continued
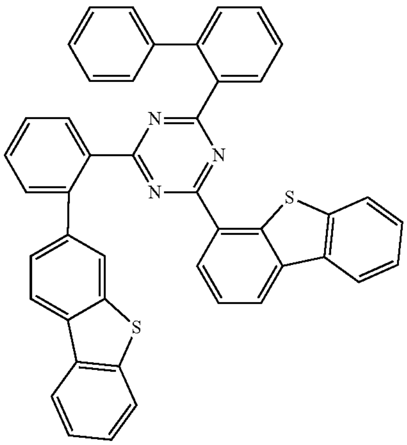
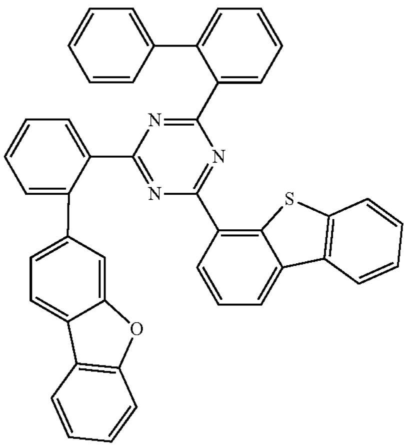
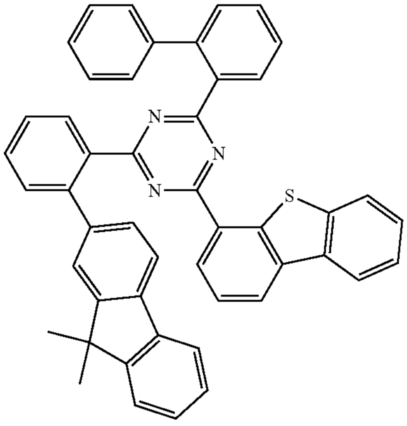
-continued
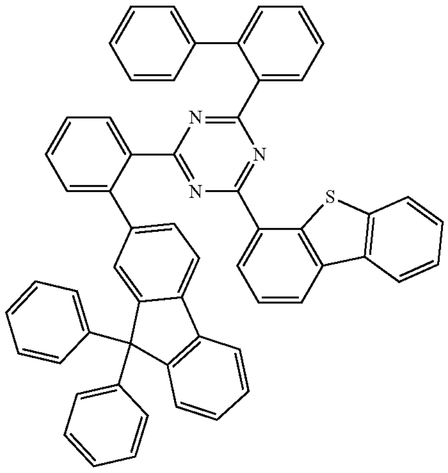
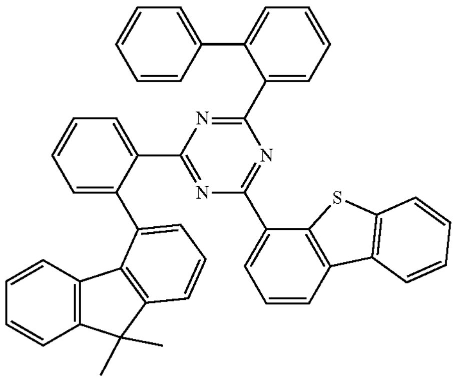
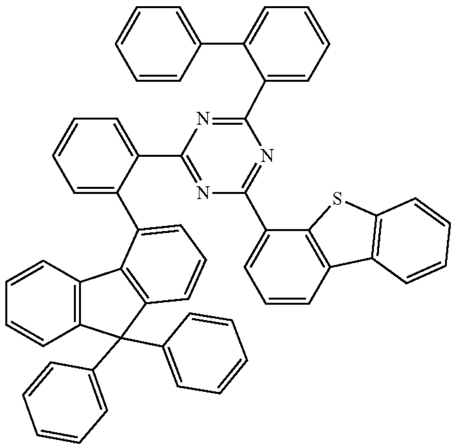
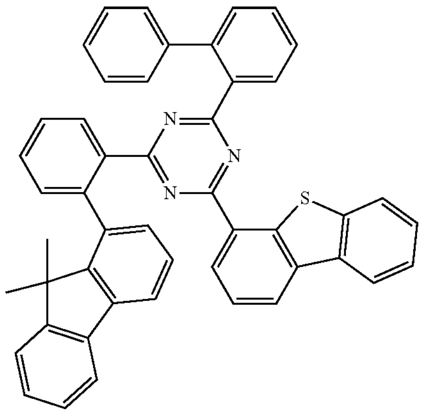

-continued
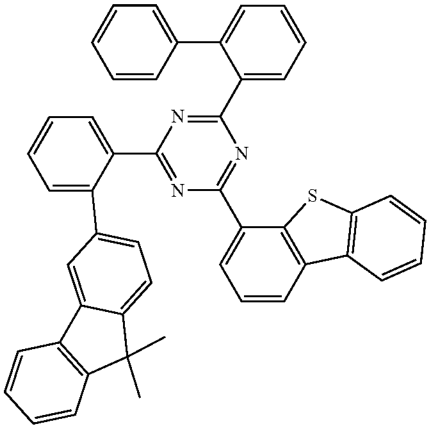
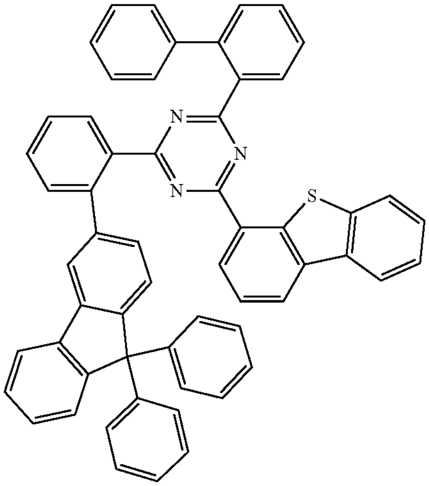
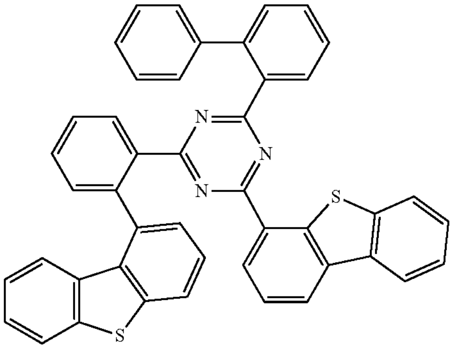
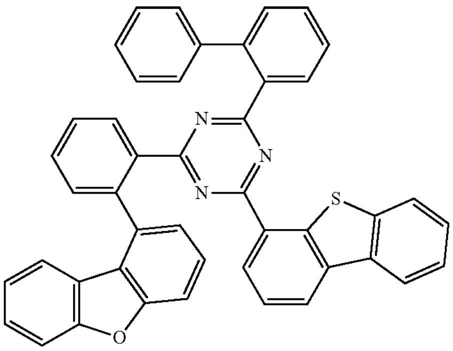
-continued
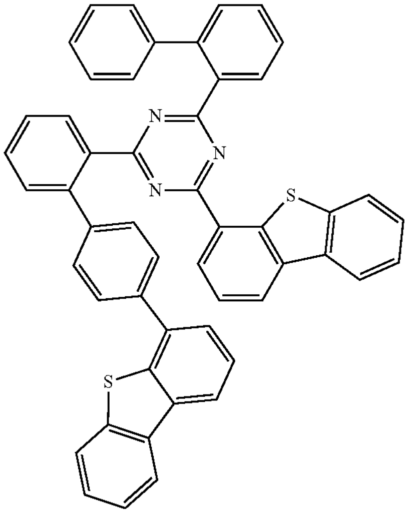
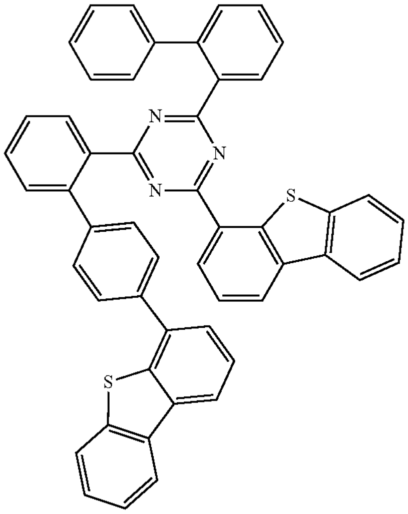
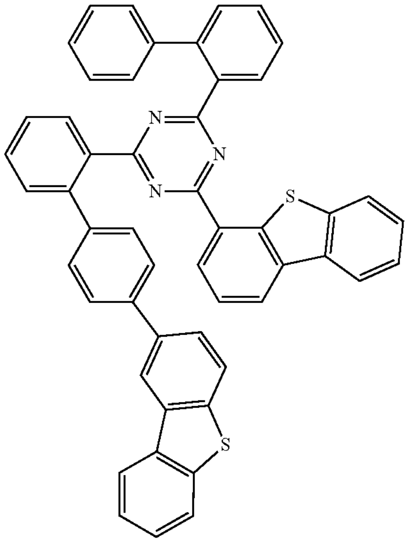

-continued
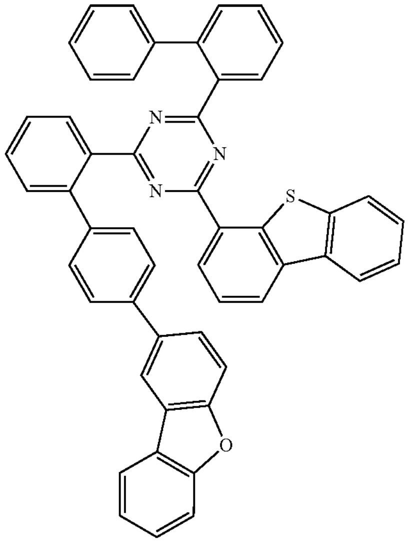
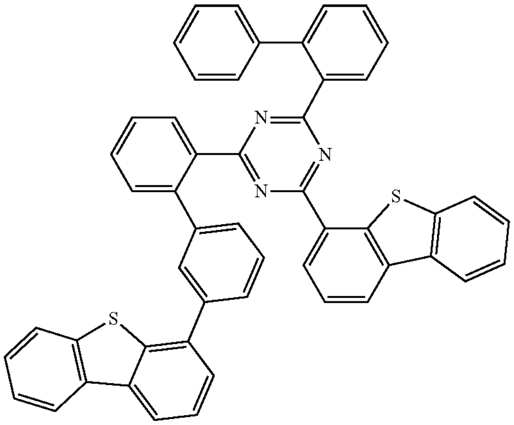
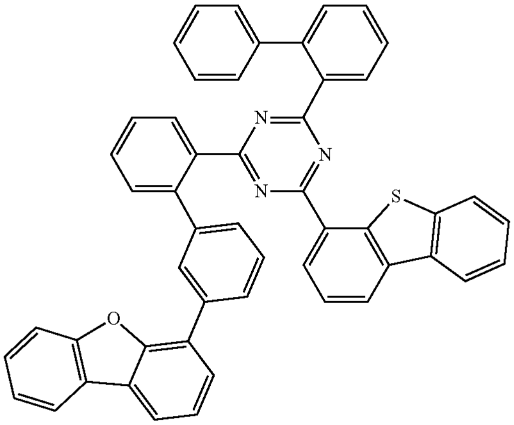
-continued
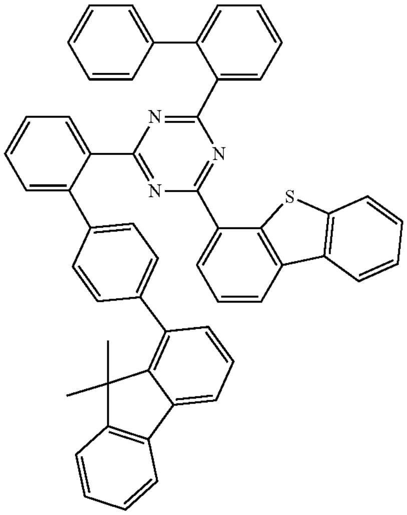
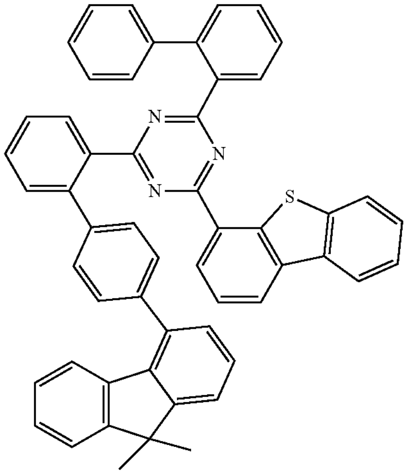
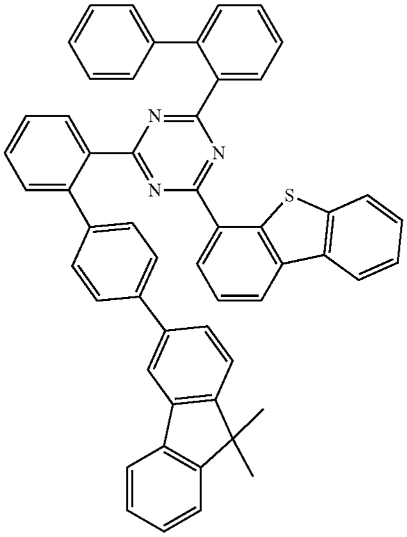

-continued
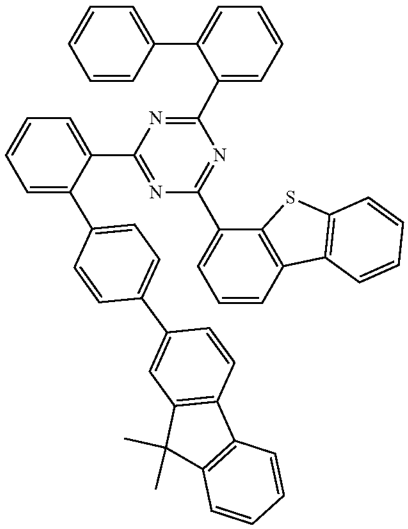
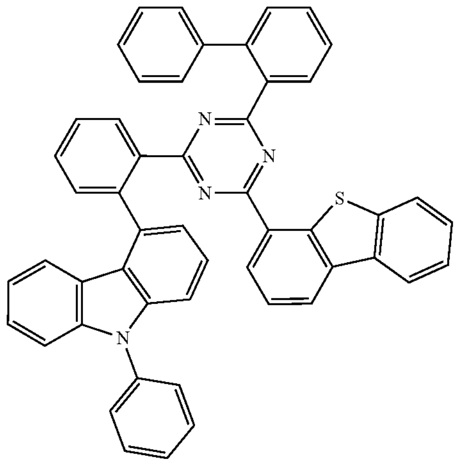
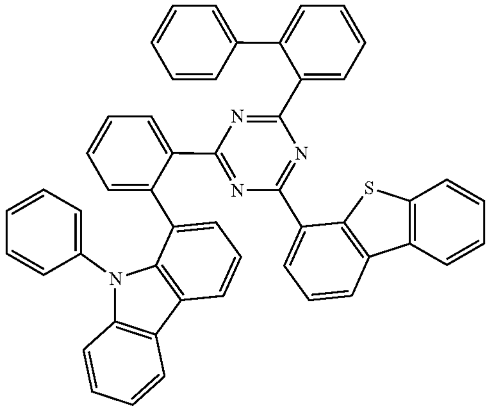
-continued
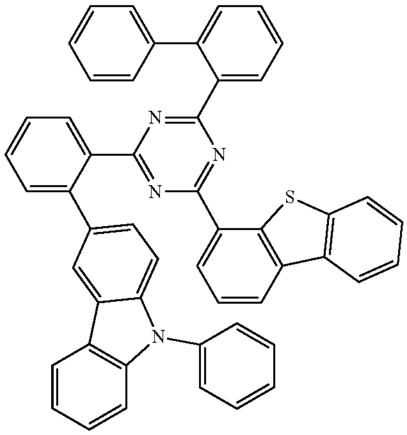
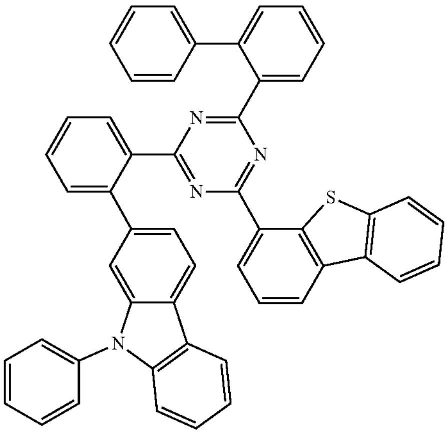
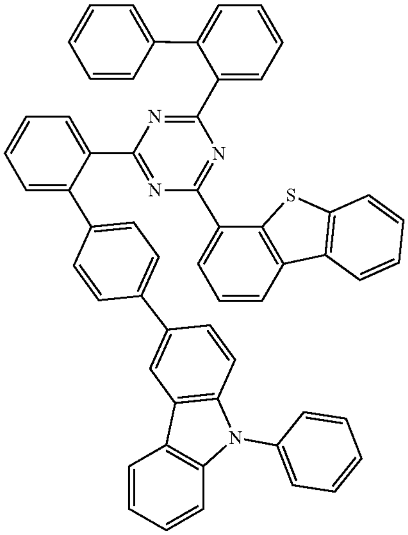

-continued
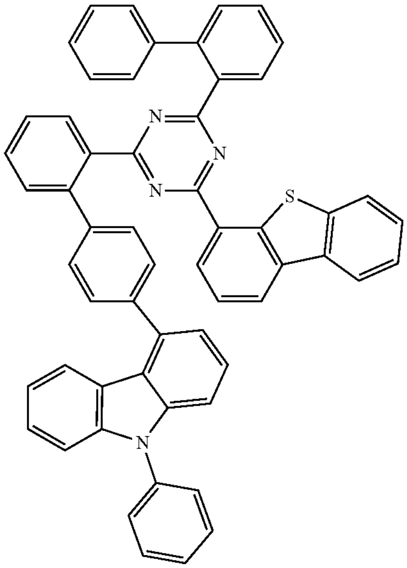
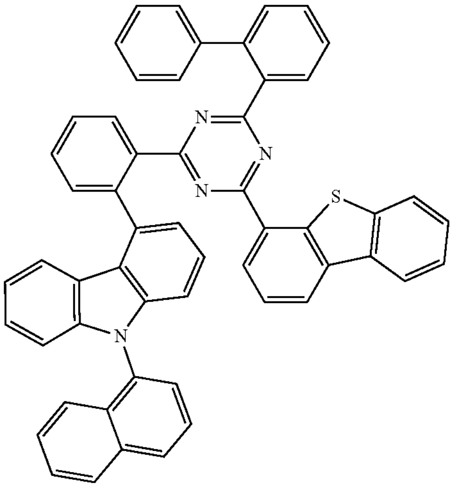
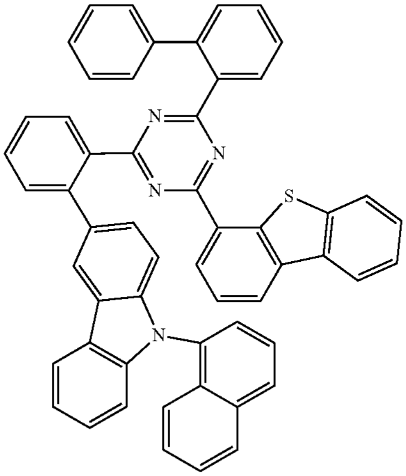
-continued
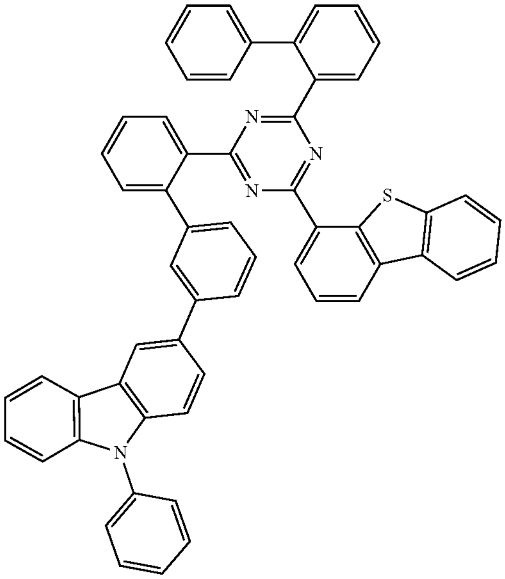
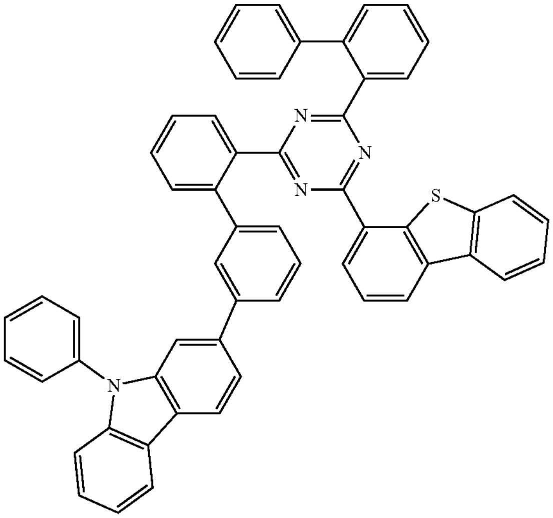
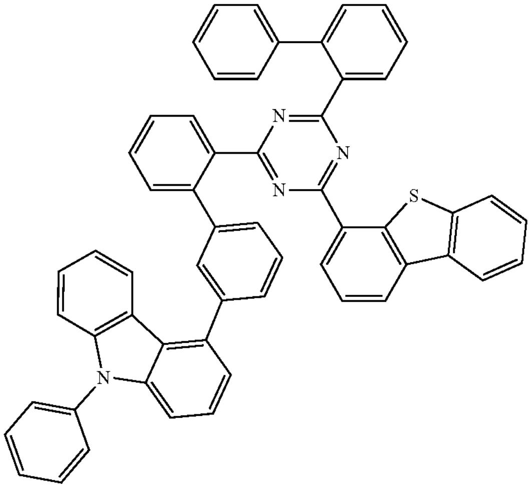

-continued
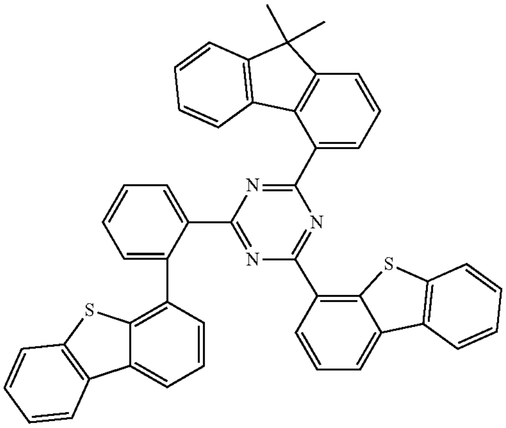
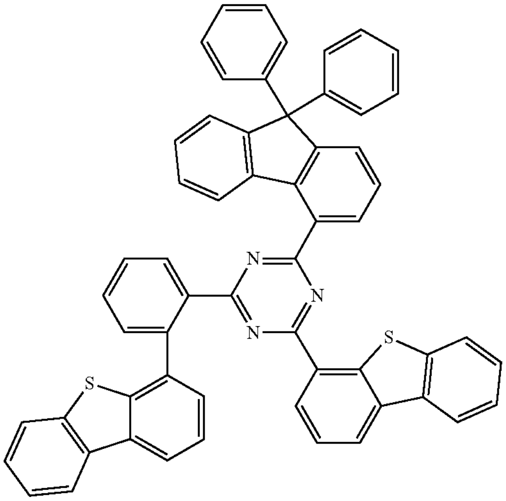
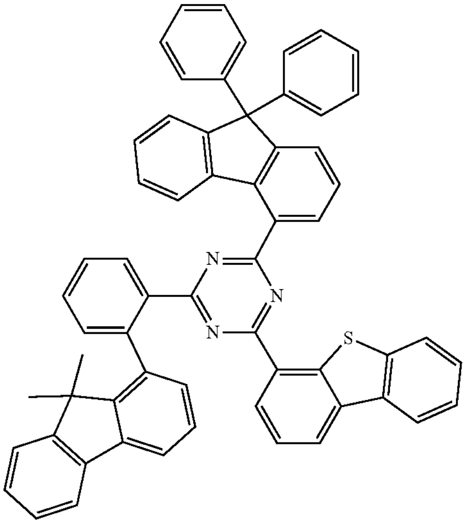
-continued
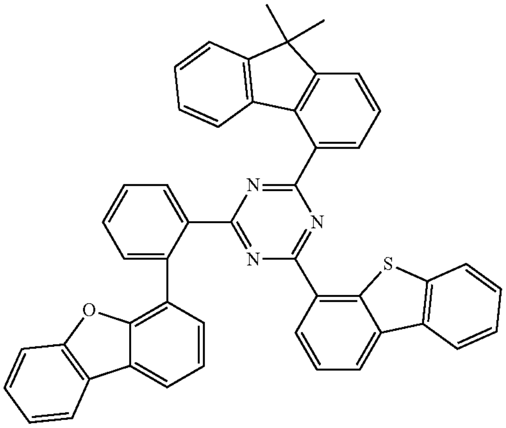
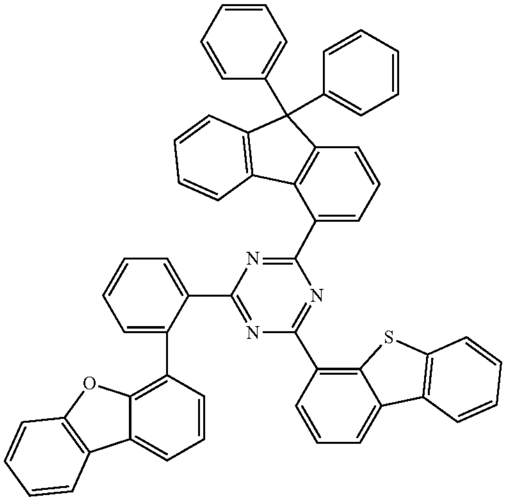
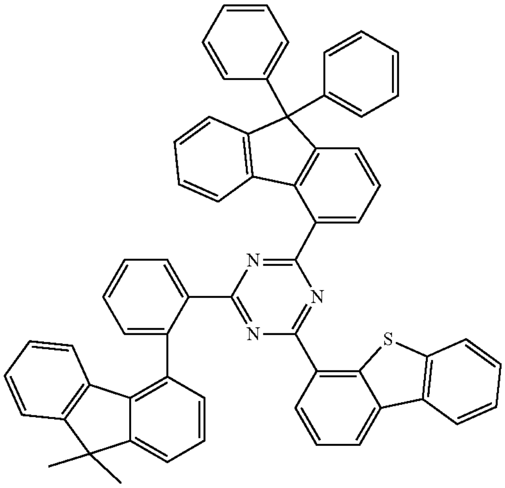

-continued
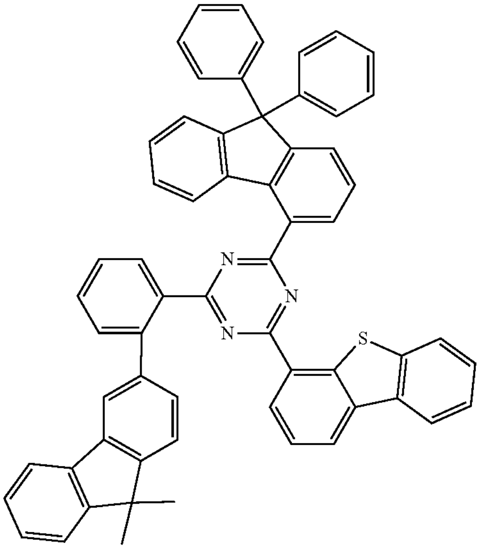
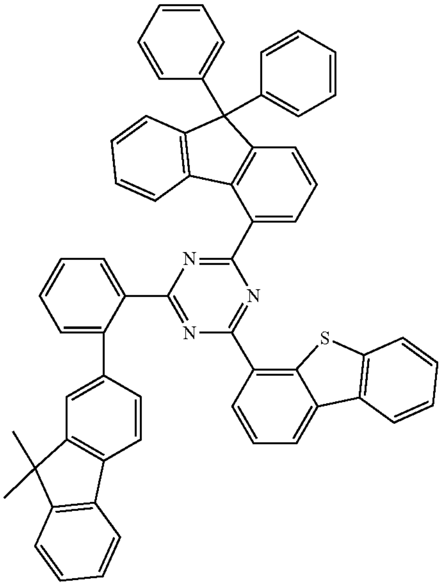
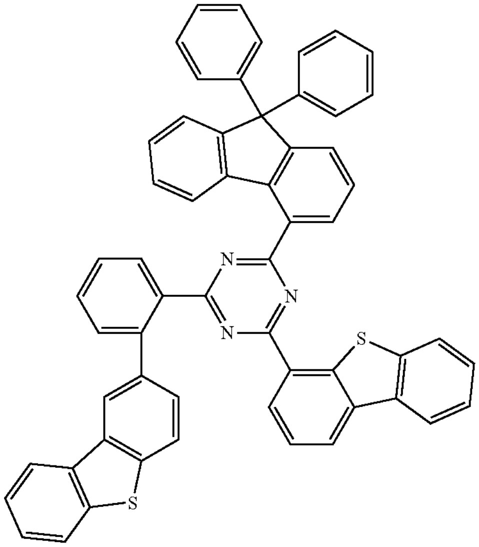
-continued
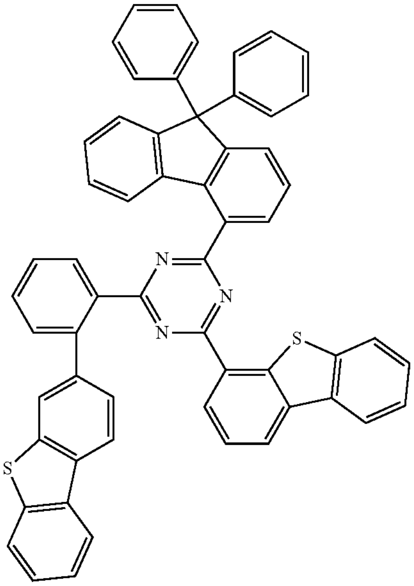
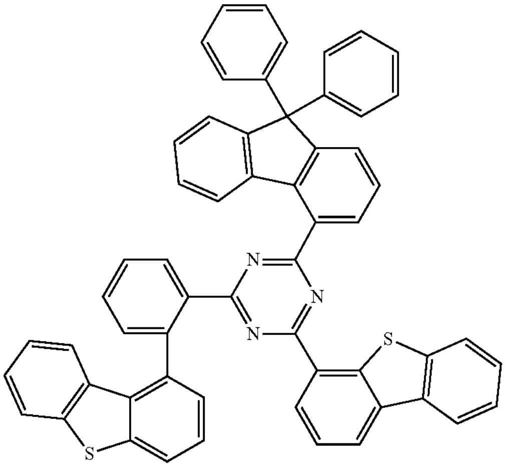
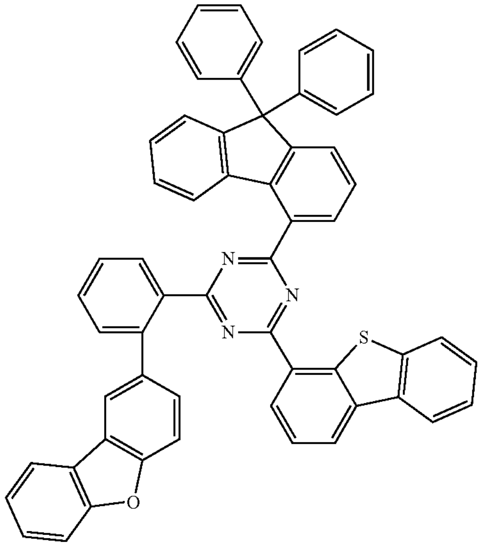

-continued
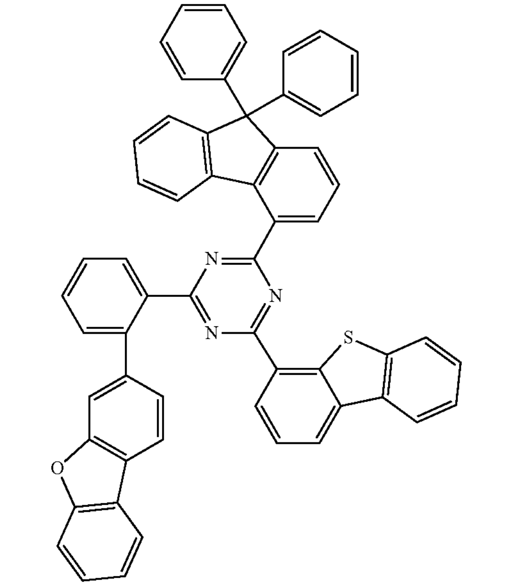
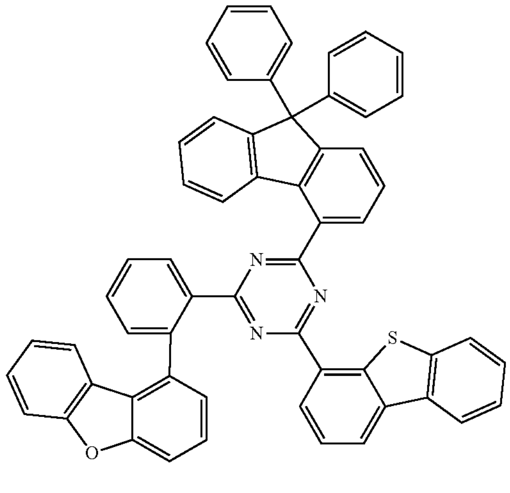
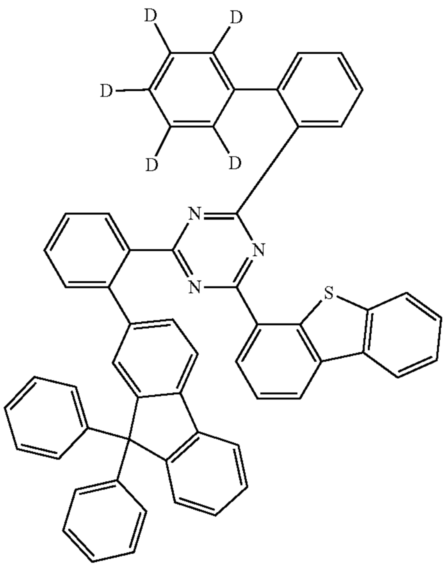
-continued
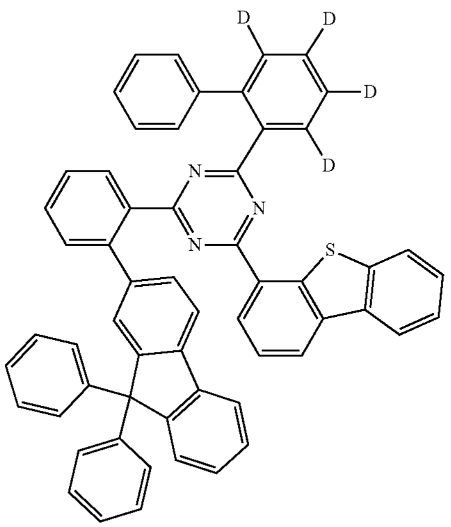
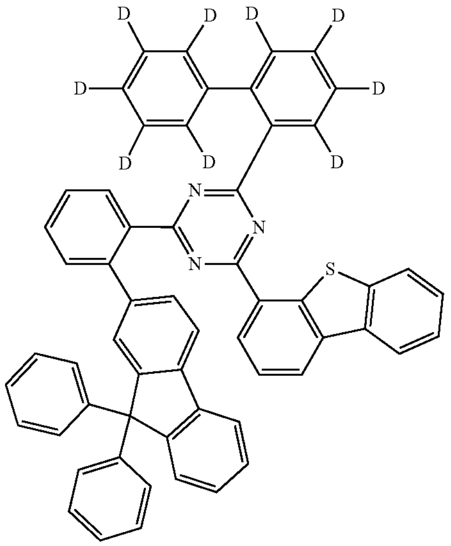
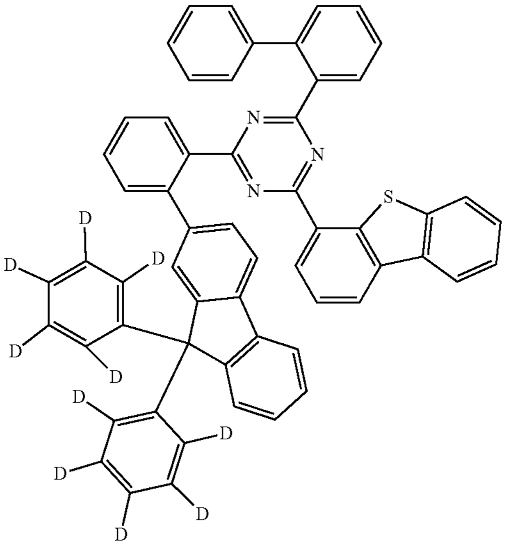

-continued
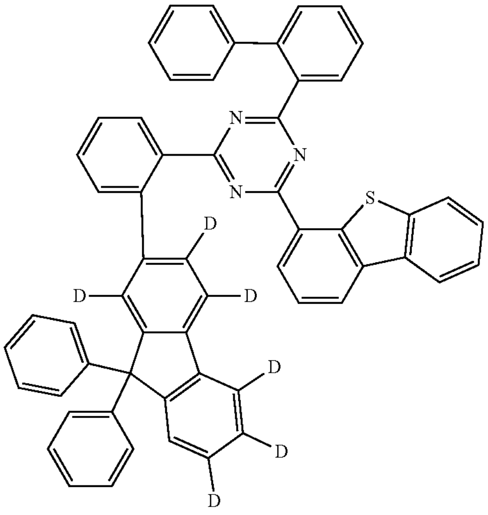
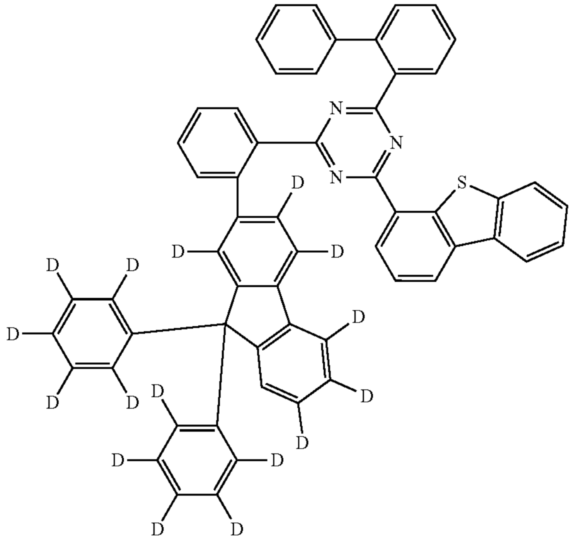
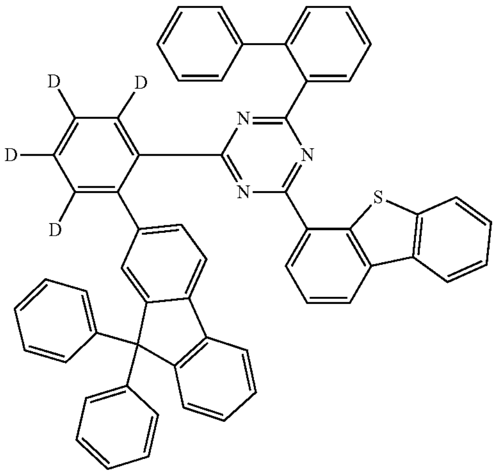
-continued
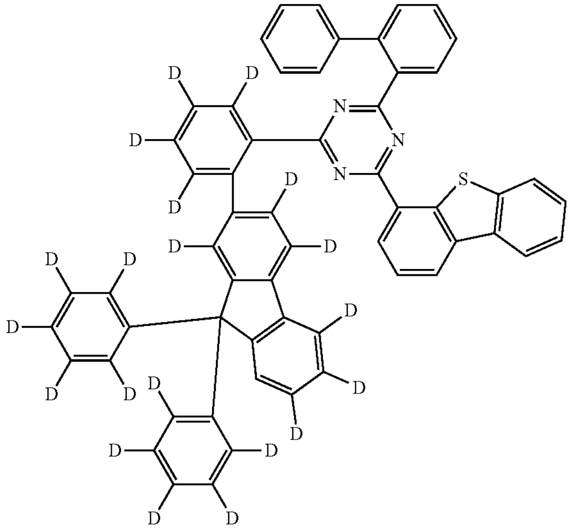
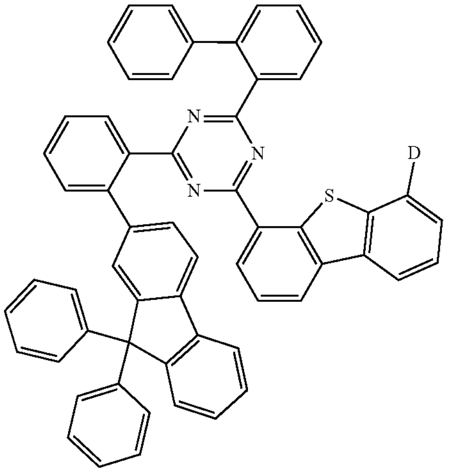
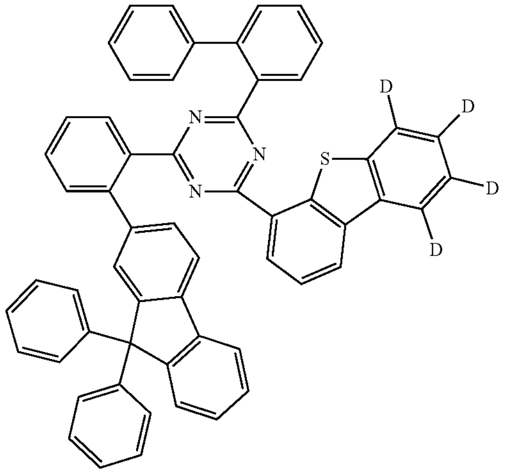

-continued
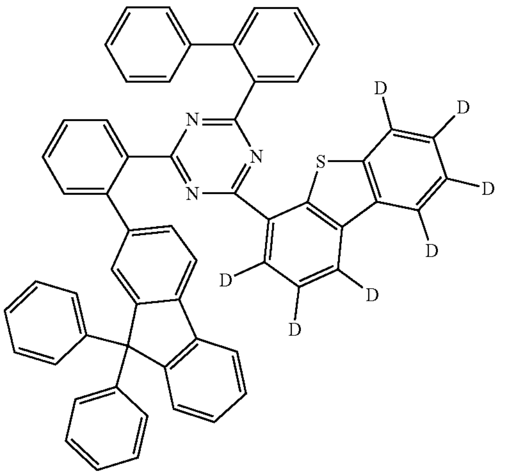
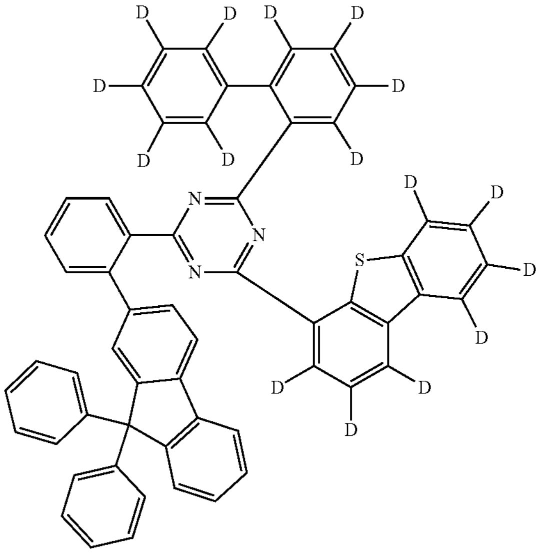
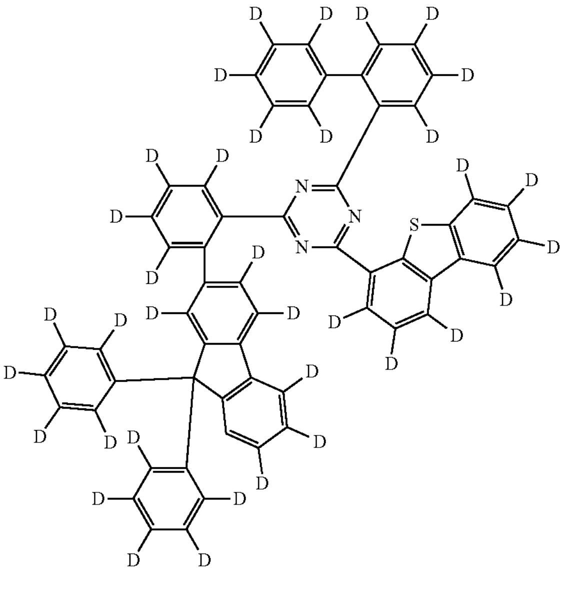
-continued
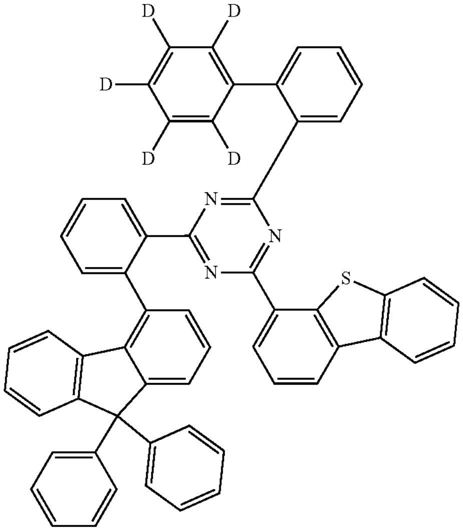
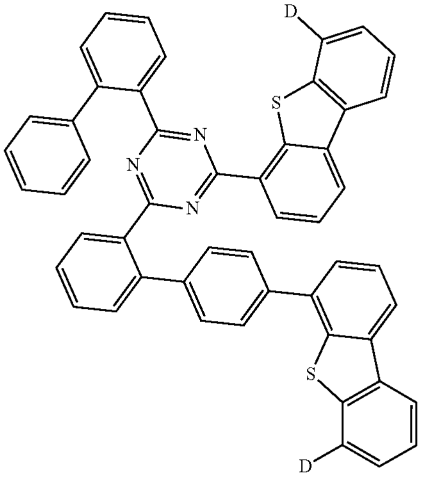
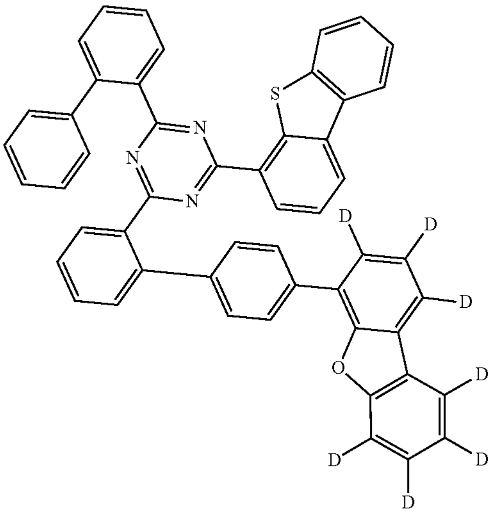

-continued
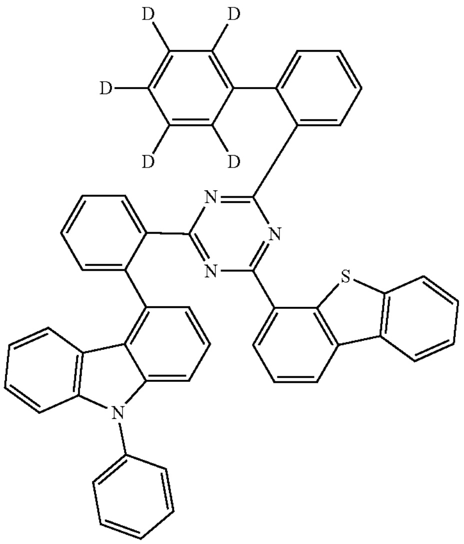
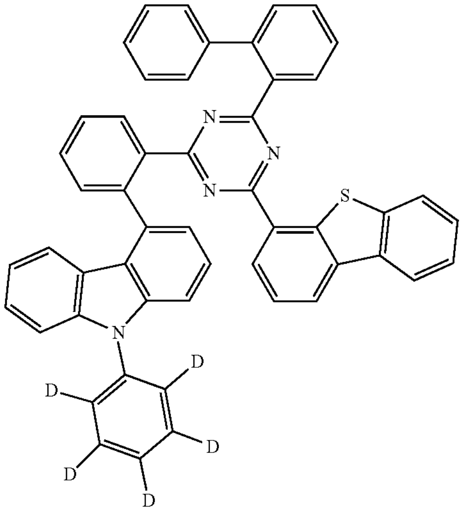
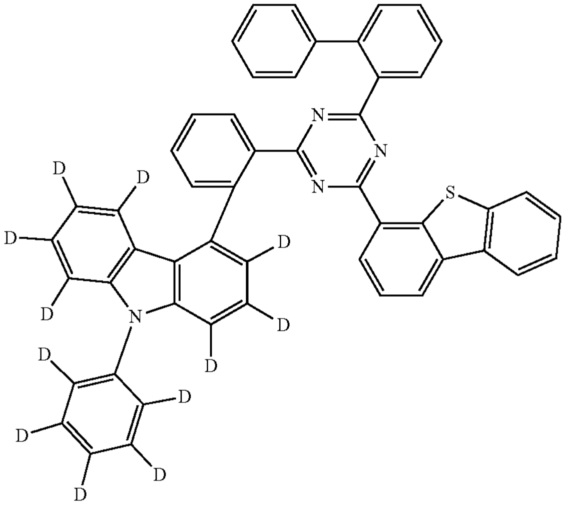
-continued
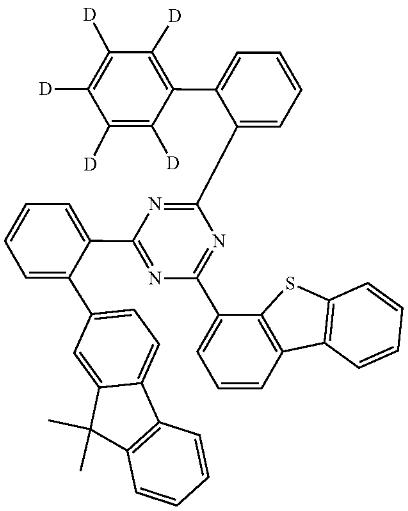
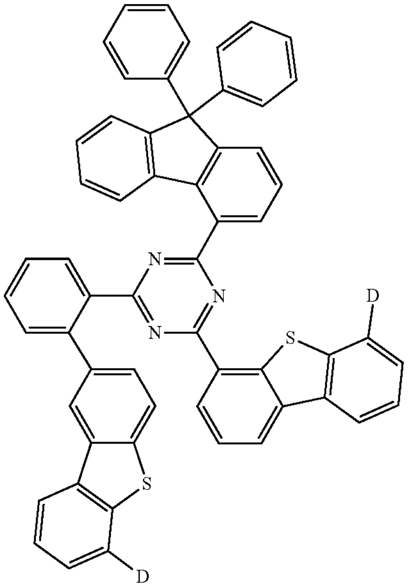

-continued

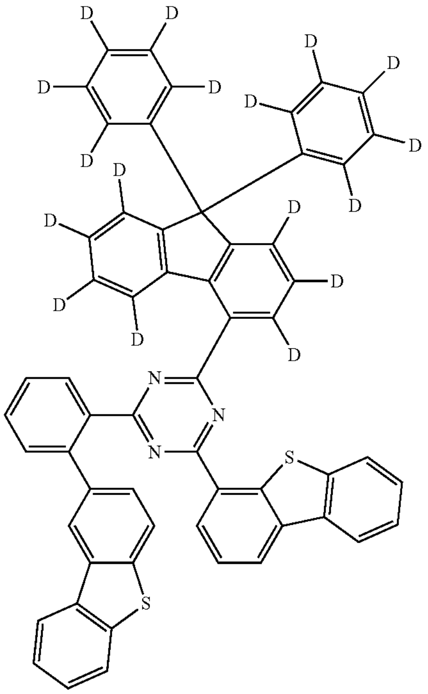

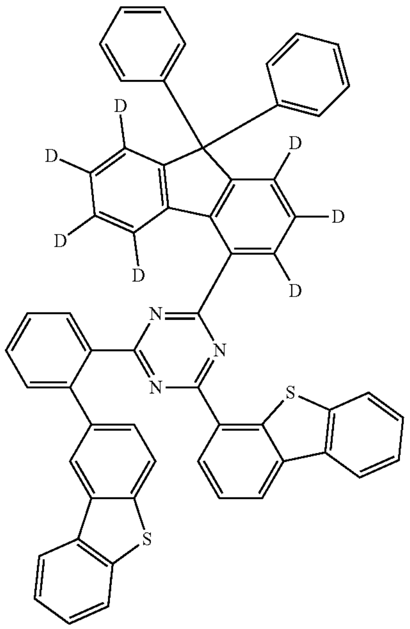

-continued

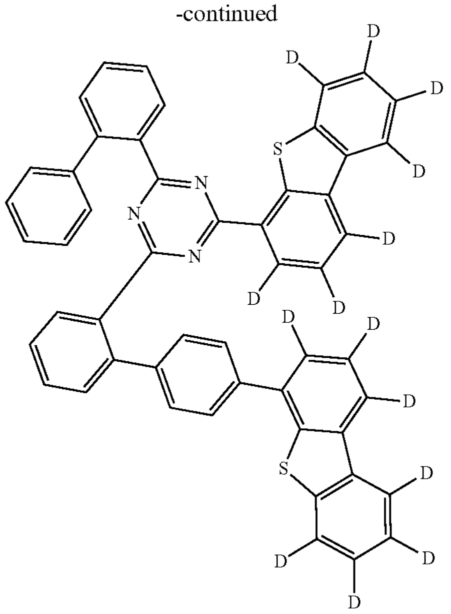

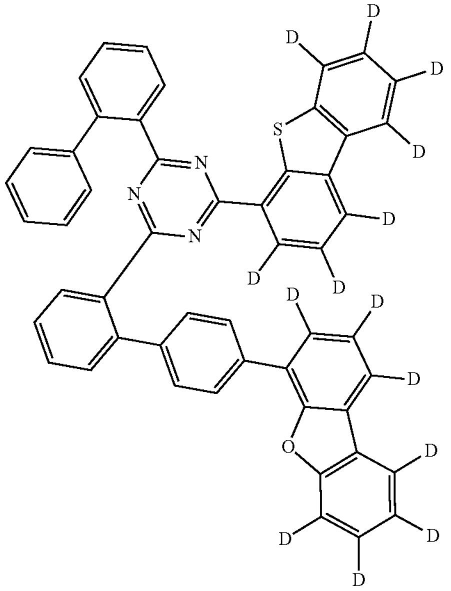

Material for Organic EL Device

The material for organic EL device of the present invention contains the inventive compound. The content of the inventive compound in the material for organic EL device is 1% by mass or more (including 100%), preferably 10% by mass or more (including 100%), more preferably 50% by mass or more (including 100%), further preferably 80% by mass or more (including 100%), and particularly preferably 90% by mass or more (including 100%). The material for an organic EL device of the present invention is useful for production of an organic EL device.

Organic EL Device

The organic EL device of the present invention includes an anode, a cathode, and an organic layer disposed between the anode and the cathode. The organic layer includes a light emitting layer, at least one layer of the organic layer contains the inventive compound.

Examples of the organic layer containing the inventive compound include, but not limited to, a hole transport zone (a hole injection layer, a hole transport layer, an electron blocking layer, an exciton blocking layer, etc.), a light emitting layer, and a space layer which are provided between the anode and the light emitting layer, an electron transport zone (an electron injection layer, an electron transport layer, a hole blocking layer, etc.) which is provided between the cathode and the light emitting layer. The inventive compound is preferably used as a material of an electron transport zone or a light emitting layer, more preferably a material of an electron transport zone, further preferably a material of an electron injection layer, an electron transport layer, a hole blocking layer, or an exciton blocking layer, and more preferably a material of an electron injection layer or an electron transport layer, of a fluorescent or phosphorescent EL device.

The organic EL device of the present invention may be a fluorescent or phosphorescent light emission-type monochrome light emitting device, a fluorescent/phosphorescent hybrid-type white light emitting device, a simple-type device having a single light emitting unit, or a tandem-type device having a plurality of light emitting units. Here, the "light emitting unit" includes an organic layer(s), at least one layer of the organic layer(s) being a light emitting layer, and the light emitting unit is a minimum unit in which injected holes and electrons are recombined to emit light.

As a typical device structure of the simple-type organic EL device, the following device structures can be exemplified.

(1) Anode/Light Emitting Unit/Cathode

The light emitting unit may be a multilayer type having a plurality of phosphorescent light emitting layers or fluorescent light emitting layers. In this case, a space layer may be included between the light emitting layers for the purpose of preventing diffusion of excitons generated in the phosphorescent light emitting layers into the fluorescent light emitting layers. Typical layer structures of the simple-type light emitting unit are shown below. The layers in the parentheses are optional layers.

(a) (Hole injection layer/)hole transport layer/fluorescent light emitting layer/electron transport layer(/electron injection layer)
(b) (Hole injection layer/)hole transport layer/phosphorescent light emitting layer electron transport layer(/electron injection layer)
(c) (Hole injection layer/)hole transport layer/first fluorescent light emitting layer/second fluorescent light emitting layer/electron transport layer(/electron injection layer)
(d) (Hole injection layer/)hole transport layer/first phosphorescent light emitting layer/second phosphorescent light emitting layer/electron transport layer(/electron injection layer)
(e) (Hole injection layer/)hole transport layer/phosphorescent light emitting layer/space layer/fluorescent light emitting layer/electron transport layer(/electron injection layer)
(f) (Hole injection layer/)hole transport layer/first phosphorescent light emitting layer/second phosphorescent light emitting layer/space layer/fluorescent light emitting layer/electron transport layer(/electron injection layer)
(g) (Hole injection layer/)hole transport layer/first phosphorescent light emitting layer/space layer/second phosphorescent light emitting layer/space layer/fluorescent light emitting layer/electron transport layer(/electron injection layer)
(h) (Hole injection layer/)hole transport layer/phosphorescent light emitting layer/space layer/first fluorescent light emitting layer/second fluorescent light emitting layer/electron transport layer(/electron injection layer)
(i) (Hole injection layer/)hole transport layer/electron blocking layer/fluorescent light emitting layer/electron transport layer(/electron injection layer)
(j) (Hole injection layer/)hole transport layer/electron blocking layer/phosphorescent light emitting layer/electron transport layer(/electron injection layer)
(k) (Hole injection layer/)hole transport layer/exciton blocking layer/fluorescent light emitting layer/electron transport layer(/electron injection layer)
(l) (Hole injection layer/)hole transport layer/exciton blocking layer/phosphorescent light emitting layer/electron transport layer(/electron injection layer)
(m) (Hole injection layer/)first hole transport layer/second hole transport layer/fluorescent light emitting layer/electron transport layer(/electron injection layer)
(n) (Hole injection layer/)first hole transport layer/second hole transport layer/phosphorescent light emitting layer/electron transport layer(/electron injection layer)
(o) (Hole injection layer/)first hole transport layer/second hole transport layer/fluorescent light emitting layer/first electron transport layer/second electron transport layer (/electron injection layer)
(p) (Hole injection layer/)first hole transport layer/second hole transport layer/phosphorescent light emitting layer/first electron transport layer/second electron transport layer(/electron injection layer)
(q) (Hole injection layer/)hole transport layer/fluorescent light emitting layer/hole blocking layer/electron transport layer(/electron injection layer)
(r) (Hole injection layer/)hole transport layer/phosphorescent light emitting layer/hole blocking layer/electron transport layer(/electron injection layer)
(s) (Hole injection layer/)hole transport layer/fluorescent light emitting layer/exciton blocking layer/electron transport layer(/electron injection layer)
(t) (Hole injection layer/)hole transport layer/phosphorescent light emitting layer/exciton blocking layer/electron transport layer(/electron injection layer)

The phosphorescent or fluorescent light emitting layers can show light emitting colors different from one another. Specifically a layer structure, in the light emitting unit (f), of (hole injection layer/)hole transport layer/first phosphorescent light emitting layer (red light emitting)/second phosphorescent light emitting layer (green light emitting)/space layer/fluorescent light emitting layer (blue light emitting)/electron transport layer is exemplified.

An electron blocking layer may be appropriately provided between each light emitting layer and a hole transport layer or a space layer. A hole blocking layer may be appropriately provided between each light emitting layer and an electron transport layer. By providing an electron blocking layer or a hole blocking layer, electrons or holes can be confined in a light emitting layer, thereby increasing the probability of recombination of the charges in the light emitting layer to enhance the light emitting efficiency.

A typical example of the device structure of the tandem-type organic EL device is the following device structure.

(2) Anode/First Light Emitting Unit/Intermediate Layer/Second Light Emitting Unit/Cathode Here, the first light emitting unit and the second light emitting unit, for example, can be each independently selected from the light emitting units described above.

For the intermediate layer, which is generally referred to also as intermediate electrode, intermediate conductive layer, charge generating layer, electron withdrawing layer, connecting layer, or intermediate insulating layer, a known material configuration in which electrons are supplied into the first light emitting unit and holes are supplied into the second light emitting unit can be used.

FIG. 1 is a schematic view showing an example of the structure of the organic EL device of the present invention. An organic EL device 1 includes a substrate 2, an anode 3, a cathode 4, and a light emitting unit 10 disposed between the anode 3 and the cathode 4. The light emitting unit 10 includes a light emitting layer 5. A hole transport zone 6 (a hole injection layer, a hole transport layer, etc.) is included between the light emitting layer 5 and the anode 3, and an electron transport zone 7 (an electron injection layer, an electron transport layer, etc.) is included between the light emitting layer 5 and the cathode 4. An electron blocking layer (not shown) may be provided on the anode 3 side of the light emitting layer 5 and a hole blocking layer (not shown) may be provided on the cathode 4 side of the light emitting layer 5. Thus, electrons or holes can be confined in the light emitting layer 5 to further increase the exciton generation efficiency in the light emitting layer 5.

Figure 2:
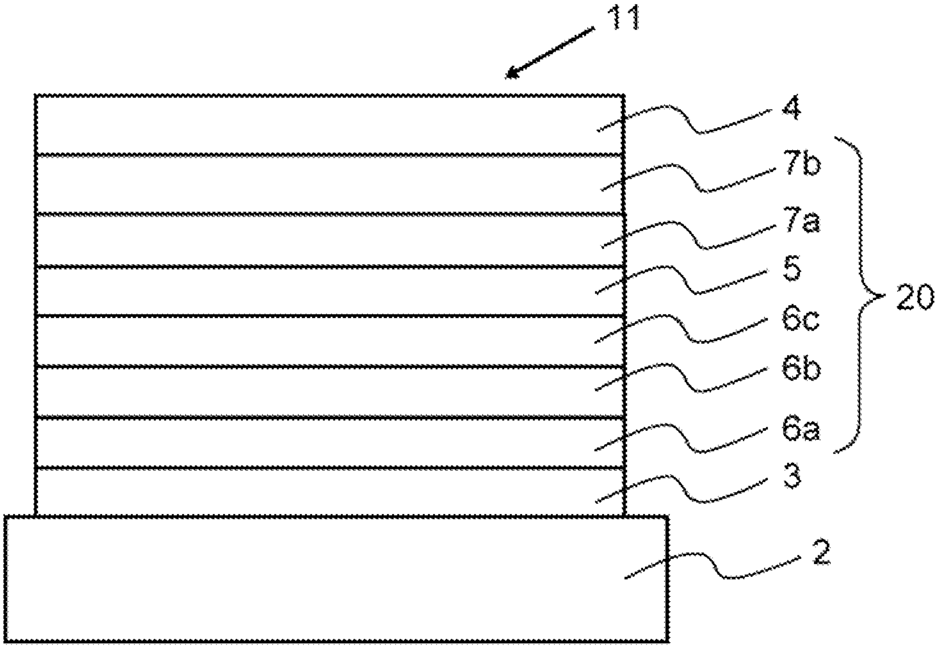
FIG. 2 is a schematic view showing another example of a layer structure of an organic EL device according to an aspect of the present invention.

FIG. 2 is a schematic view showing another structure of the organic EL device of the present invention. An organic EL device 11 include the substrate 2, the anode 3, the cathode 4, and a light emitting unit 20 disposed between the anode 3 and the cathode 4. The light emitting unit 20 includes the light emitting layer 5. A hole transport zone disposed between the anode 3 and the light emitting layer 5 is formed of a hole injection layer 6*a*, a first hole transport layer 6*b*, and a hole transport layer 6*c*. An electron transport zone disposed between the light emitting layer 5 and the cathode 4 is formed of a first electron transport layer 7*a* and a second electron transport layer 7*b*.

In the present invention, a host combined with a fluorescent dopant (fluorescent light emitting material) is referred to as a fluorescent host and a host combined with a phosphorescent dopant is referred to as a phosphorescent host. The fluorescent host and the phosphorescent host are distinguished not only by the molecular structure. That is, the phosphorescent host means a material that forms a phosphorescent light emitting layer containing a phosphorescent dopant and does not mean that the phosphorescent host cannot be used as a material that forms a fluorescent light emitting layer. The same applies to the fluorescent host.

Substrate

A substrate is used as a support of an organic EL device. As a substrate, for example, a plate of glass, quartz, or a plastic can be used. Alternatively a flexible substrate may be used. Examples of the flexible substrate include plastic substrates each formed of polycarbonate, polyarylate, polyether sulfone, polypropylene, polyester, polyvinyl fluoride, or polyvinyl chloride. Alternatively an inorganic vapor deposited film can be used.

Anode

As the anode formed on the substrate, a metal, an alloy or a conductive compound which have a high work function (specifically 4.0 eV or higher), a mixture thereof, and the like are preferably used. Specific examples thereof include indium oxide-tin oxide (ITO: indium tin oxide), indium oxide-tin oxide containing silicon or silicon oxide, indium oxide-zinc oxide, indium oxide containing tungsten oxide and zinc oxide, and graphene. Besides, gold (Au), platinum (Pt), nickel (Ni), tungsten (W), chromium (Cr), molybdenum (Mo), iron (Fe), cobalt (Co), cupper (Cu), palladium (Pd), titanium (Ti), or a nitride of the metals (for example, titanium nitride).

The materials are generally formed into a film generally by a sputtering method. For example, indium oxide-zinc oxide can be formed by using a target of indium oxide with 1 to 10 wt % of zinc oxide added relative to the indium oxide, and indium oxide containing tungsten oxide and zinc oxide can be formed by using a target of indium oxide containing 0.5 to 5 wt % of tungsten oxide and 0.1 to 1 wt % of zinc oxide relative to the indium oxide, by a sputtering method. Alternatively the materials may be produced by a vacuum vapor deposition method, a coating method, an inkjet method, a spin coating method, or the like.

Since the hole injection layer that is to be formed in contact with the anode is formed by using a material into which holes are easily injected regardless of the work function of the anode, a material that is generally used as an electrode material (for example, a metal, an alloy a conductive compound, a mixture thereof, or an element belonging to Group I or Group II of the periodic table) can be used.

Elements belonging to Group I or Group II of the periodic table which are materials having a low work function, i.e., alkali metals, such as lithium (Li) and cesium (Cs), alkaline earth metals, such as magnesium (Mg), calcium (Ca), and strontium (Sr), alloys containing the metals (for example, MgAg, AlLi), rare earth metals, such as europium (Eu) and ytterbium (Yb), and alloys containing the metals can be used. When an anode is formed with an alkali metal, an alkaline earth metal, and an alloy containing the metals, a vacuum vapor deposition method or a sputtering method can be used. When silver paste or the like is used, a coating method, an inkjet method, or the like can be used.

Hole Injection Layer

The hole injection layer is a layer containing a material having a high hole injection property (hole injecting material), and is formed between the anode and the light emitting layer, or between a hole transport layer, if present, and the anode.

As a hole injecting material, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, and the like can be used.

Aromatic amine compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1) which are low molecular organic compounds, are also exemplified as the hole injection layer material.

A high molecular compound (oligomer, dendrimer, polymer, etc.) can also be used. Examples thereof include high molecular compounds, such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). A high molecular compound with an acid added therein, such as poly(3,4-ethylenedioxythiophene)/poly(styrene-sulfonic acid) (PEDOT/PSS) or polyaniline/poly(styrene sulfonic acid) (PAni/PSS), can also be used.

An acceptor material, such as a hexaazatriphenylene (HAT) compound, represented by the following formula (K), is also preferably used.

(K)

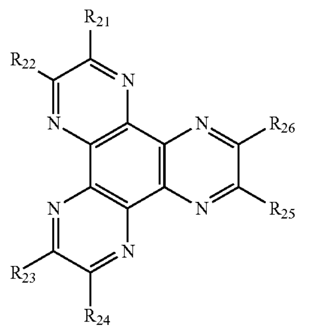

(In the formula, $R_{21}$ to $R_{26}$ each independently represent a cyano group, —$CONH_2$, a carboxyl group, or —$COOR_{27}$ ($R_{27}$ represents an alkyl group having 1 to 20 carbon atoms or a cycloalkyl group having 3 to 20 carbon atoms). The adjacent two selected from $R_{21}$ and $R_{22}$, $R_{23}$ and $R_{24}$, and $R_{25}$ and $R_{26}$ may bind to each other to form a group represented by —CO—O—CO—.)

Examples of $R_{27}$ include a methyl group, an ethyl group, an n-propyl group, an isopropyl group, an n-butyl group, an isobutyl group, a t-butyl group, a cyclopentyl group, and a cyclohexyl group.

Hole Transport Layer

The hole transport layer is a layer containing a material having a high hole transport property (hole transporting material), and is formed between the anode and the light emitting layer, or between a hole injection layer, if present, and the light emitting layer.

The hole transport layer may have a monolayer structure or a multilayer structure. For example, the hole transport layer may have a two-layer structure including a first hole transport layer (on the anode side) and a second hole transport layer (on the cathode side). In an aspect of the present invention, the hole transport layer of the monolayer structure is preferably adjacent to the light emitting layer, or the hole transport layer nearest to the cathode in the multi-layer structure, for example, the second hole transport layer in the two-layer structure is preferably adjacent to the light emitting layer. In another aspect of the present invention, an electron blocking layer as described later or the like may be interposed between the hole transport layer of the monolayer structure and the light emitting layer, or between the hole transport layer nearest to the light emitting layer in the multilayer structure and the light emitting layer.

As a material for the hole transport layer, for example, an aromatic amine compound, a carbazole derivative, an anthracene derivative, or the like can be used.

Examples of the aromatic amine compound include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluoren-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB). The compound has a hole mobility of $10^{-6}$ $cm^2/Vs$ or more.

Examples of the carbazole derivative include 4,4'-di(9-carbazolyl)biphenyl (abbreviation: CBP), 9-[4-(9-carbazolyl)phenyl]-10-phenylanthracene (abbreviation: CzPA), and 9-phenyl-3-[4-(10-phenyl-9-anthryl)phenyl]-9H-carbazole (abbreviation: PCzPA).

Examples of the anthracene derivative include 2-t-butyl-9,10-di(2-naphthyl)anthracene (abbreviation: t-BuDNA), 9,10-di(2-naphthyl)anthracene (abbreviation: DNA), and 9,10-diphenylanthracene (abbreviation: DPAnth).

High molecular compounds, such as poly(N-vinylcarbazole) (abbreviation: PVK) and poly(4-vinyltriphenylamine) (abbreviation: PVTPA), can also be used.

However, any compound other than the above may be used as long as it has a higher hole transport property rather than the electron transport property.

Dopant Material of Light Emitting Layer

The light emitting layer is a layer containing a material having a high light emitting property (dopant material), and various materials can be used. For example, a fluorescent light emitting material or a phosphorescent light emitting material can be used as a dopant material. The fluorescent light emitting material is a compound that emits light from a singlet excited state, and a phosphorescent light emitting material is a compound that emits light from a triplet excited state.

As a blue fluorescent light emitting material usable for a light emitting layer, a pyrene derivative, a styrylamine derivative, a chrysene derivative, a fluoranthene derivative, a fluorene derivative, a diamine derivative, a triaryl amine derivative, and the like can be used. Specific examples thereof include N,N'-bis[4-(9H-carbazol-9-yl)phenyl]-N,N'-diphenylstyrbene-4,4'-diamine (abbreviation: YGA2S), 4-(9H-carbazol-9-yl)-4'-(10-phenyl-9-anthryl)triphenylamine (abbreviation: YGAPA), and 4-(10-phenyl-9-anthryl)-4'-(9-phenyl-9H-carbazol-3-yl)triphenylamine (abbreviation: PCBAPA).

As a green fluorescent light emitting material usable for a light emitting layer, an aromatic amine derivative and the like can be used. Specific examples thereof include N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracene-2-amine (abbreviation: 2YGABPhA), and N,N,9-triphenylanthracene-9-amine (abbreviation: DPhAPhA).

As a red fluorescent light emitting material usable for a light emitting layer, a tetracene derivative, a diamine derivative, and the like can be used. Specific examples thereof include N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphth[1,2-a]fluoranthne-3,10-diamine (abbreviation: p-mPhAFD).

As a blue phosphorescent light emitting material usable for a light emitting layer, a metal complex, such as an iridium complex, an osmium complex, or a platinum complex, is used. Specific examples thereof include bis[2-(4',6'-difluorophenyl)pyridinato-N,C2']iridium(III) tetrakis(1-pyrazolyl)borate (abbreviation: FIr6), bis[2-(4',6'-difluorophenyl)pyridinato-N,C2']iridium(III) picolinate (abbreviation: FIrpic), bis[2-(3',5'-bistrifluoromethylphenyl) pyridinato-N,C2']iridium(III) picolinate (abbreviation: Ir(CF3ppy)2(pic)), and bis[2-(4',6'-difluorophenyl)pyridinato-N,C2']iridium(III) acetylacetonate (abbreviation: FIracac).

As a green phosphorescent light emitting material usable for a light emitting layer, an iridium complex or the like is used. Examples thereof include tris(2-phenylpyridinato-N,C2')iridium(III) (abbreviation: Ir(ppy)3), bis(2-phenylpyridinato-N,C2')iridium(III) acetylacetonate (abbreviation: Ir(ppy)2(acac)), bis(1,2-diphenyl-1H-benzimidazolato) iridium(III) acetylacetonate (abbreviation: Ir(pbi)2(acac)), and bis(benzo[h]quinolinato)iridium(III) acetylacetonate (abbreviation: Ir(bzq)2(acac)).

As a red phosphorescent light emitting material usable for a light emitting layer, a metal complexes, such as an iridium complex, a platinum complex, a terbium complex, or a europium complex, is used. Specific examples thereof include organic metal complexes, such as bis[2-(2'-benzo[4,5-a]thienyl)pyridinato-N,C3']iridium(III) acetylacetonate (abbreviation: Ir(btp)2(acac)), bis(1-phenyl isoquinolinato-N,C2')iridium(III) acetylacetonate (abbreviation: Ir(piq)2 (acac)), (acetylacetonate)bis[2,3-bis(4-fluorophenyl)quinolinato]iridium(III) (abbreviation: Ir(Fdpq)2(acac)), 2,3,7,8,12,13,17,18-octaenyl-21H,23H-porphyrin platinum(II) (abbreviation: PtOEP).

Rare earth metal complexes, such as tris(acetylacetonate) (monophenanthroline)terbium(III) (abbreviation: Tb(acac)3 (Phen)), tris(1,3-diphenyl-1,3-propanedionato) (monophenanthroline)europium(III) (abbreviation: Eu(DBM)3 (Phen)), tris[1-(2-thenoyl)-3,3,3-trifluoroacetonato] (monophenanthroline)europium(III) (abbreviation: Eu(TTA)3(Phen)) emit light from rare earth metal ions (electron transfer between different multiplicities) and thus, can be used as a phosphorescent light emitting material.

Host Material of Light Emitting Layer

The light emitting layer may have a structure in which the dopant material as described above is dispersed in another material (host material). A material having a lowest unoccupied molecular orbital level (LUMO level) higher than that of the dopant material and having a highest unoccupied molecular orbital level (HOMO level) lower than that of the dopant material is preferably used.

As the host material, for example, (1) a metal complex, such as an aluminum complex, a beryllium complex, or a zinc complex, (2) a heteroring compound, such as an oxadiazole derivative, a benzimidazole derivative, or a phenanthroline derivative, (3) a condensed aromatic compound, such as a carbazole derivative, an anthracene derivative, a phenanthrene derivative, a pyrene derivative, or a chrysene derivative, or (4) an aromatic amine compound, such as a triaryl amine derivative or a condensed polycyclic aromatic amine derivative is used.

For example, a metal complex, such as tris(8-quinolinolato)aluminum(III) (abbreviation: Alq), tris(4-methyl-8-quinolinolato)aluminum(III) (abbreviation: Almq3), bis(10-hydroxybenzo[h]quinolinato)beryllium(II) (abbreviation: BeBq2), bis(2-methyl-8-quinolinolato)(4-phenylphenolato) aluminum(III) (abbreviation: BAlq), bis(8-quinolinolato) zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ);

a heteroring compound, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), or bathocuproine (abbreviation: BCP);

a condensed aromatic compound, such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis (3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stylbene-3,3'-diyl)diphenanthrene (abbreviation: DPNS), 9,9'-(stylbene-4,4'-diyl)diphenanthrene (abbreviation: DPNS2), 3,3',3"-(benzene-1,3,5-triyl)tripyrene (abbreviation: TPB3), 9,10-diphenylanthracene (abbreviation: DPAnth), or 6,12-dimethoxy-5,11-diphenylchrysene; and an aromatic amine compound, such as N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation:2PCAPA), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(9,9-dimethylfluoren-2-yl)-N-phenylamino]biphenyl (abbreviation: DFLDPBi), or 4,4'-bis[N-(spiro-9,9'-bifluoren-2-yl)-N-phenylamino]biphenyl (abbreviation: BSPB) can be used. Two or more host materials may also be used.

In particular, in the case of a blue fluorescent device, the following anthracene compounds are preferably used as a host material.

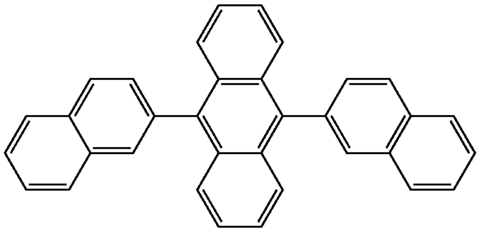
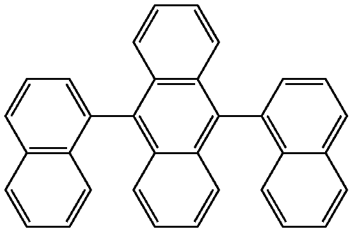
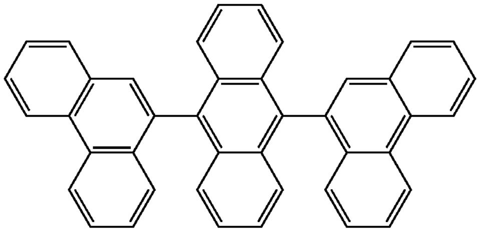
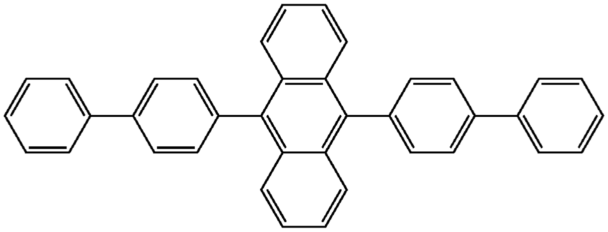
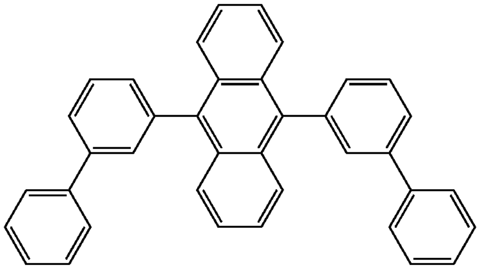
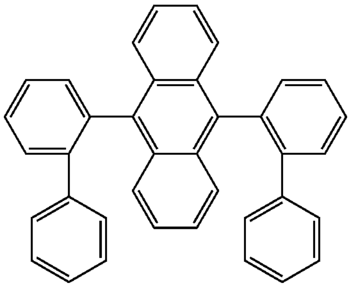
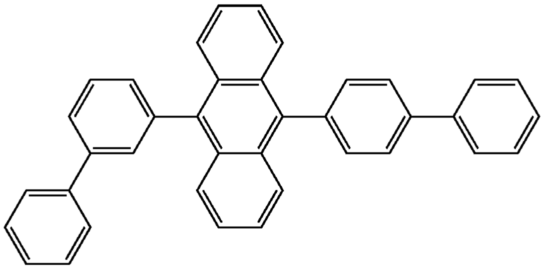
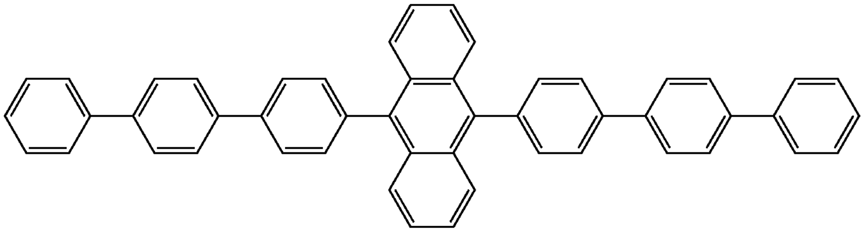
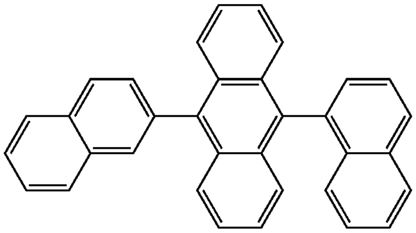
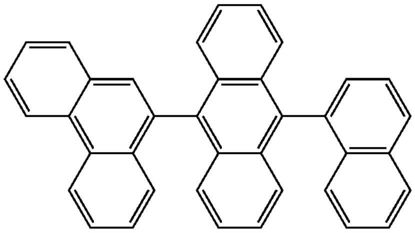
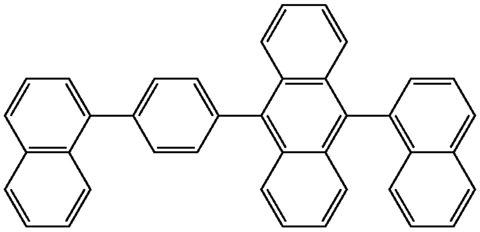
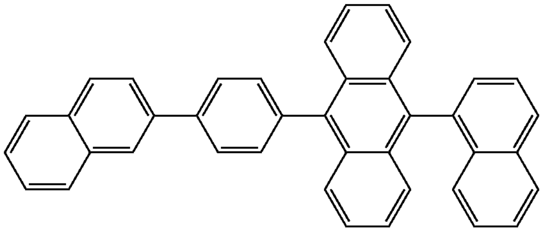

-continued
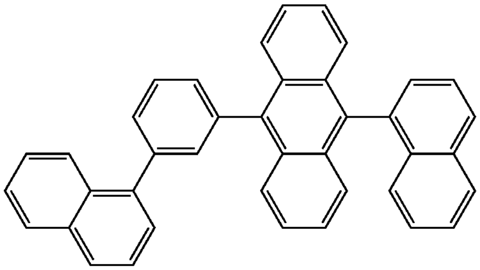
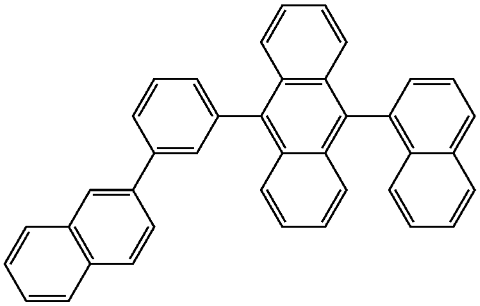
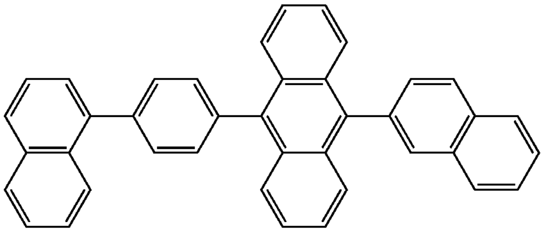
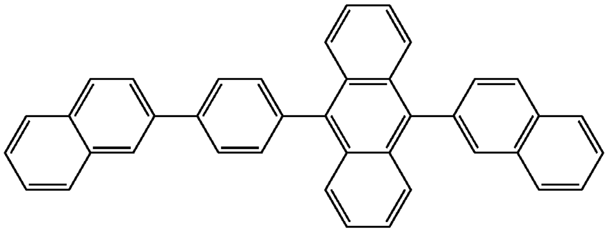
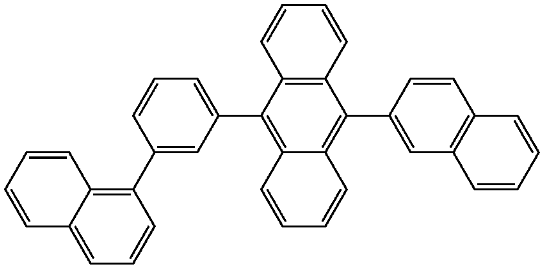
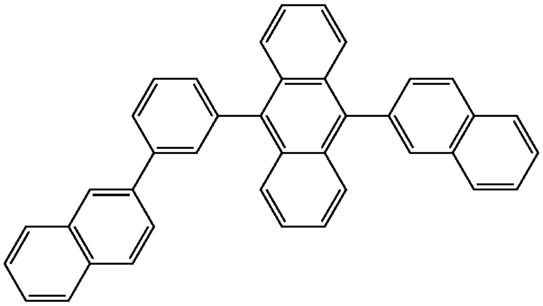
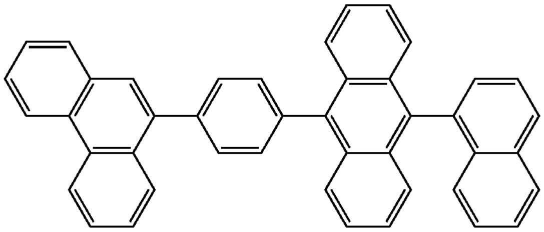
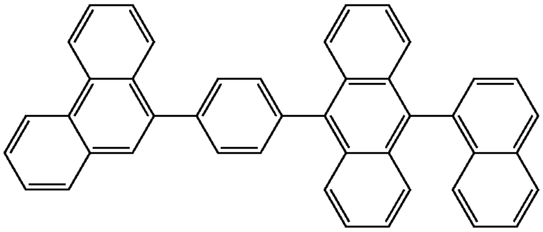
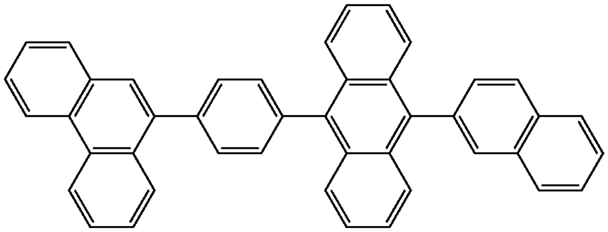
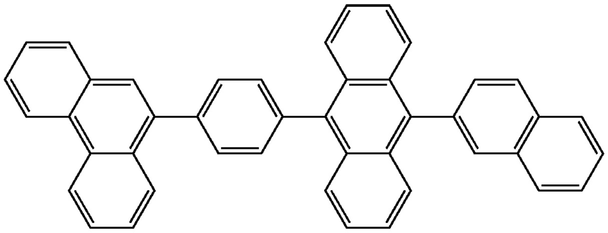
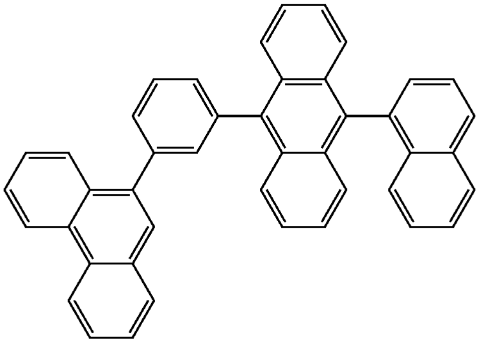

-continued
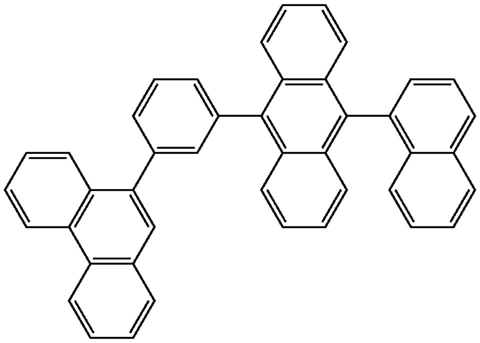
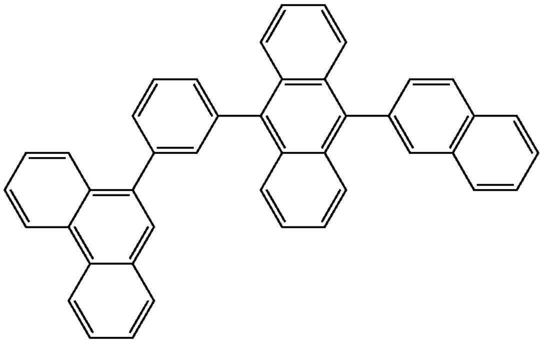
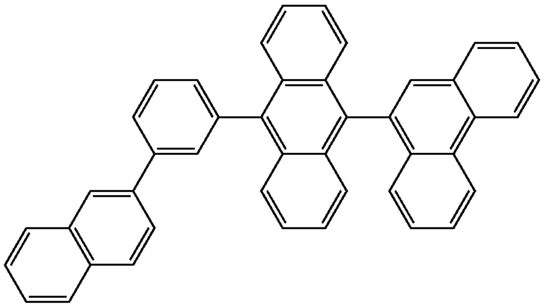
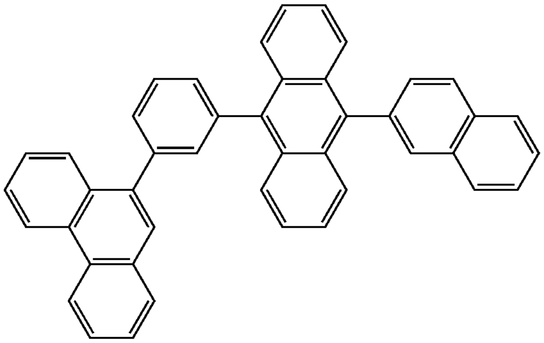
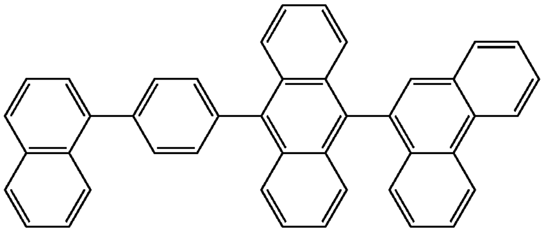
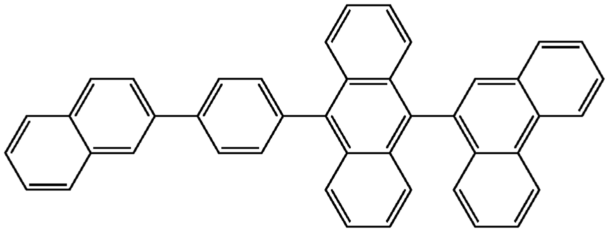
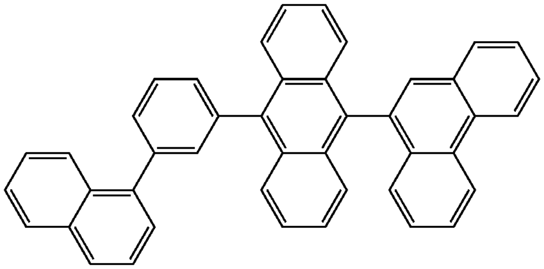
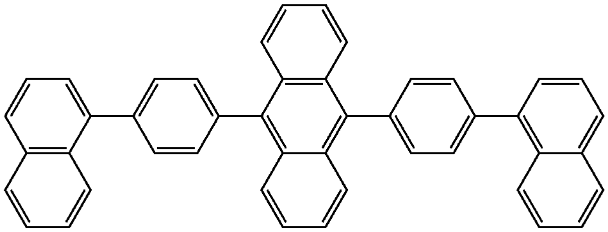
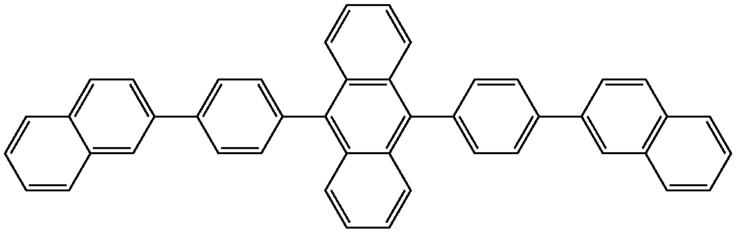
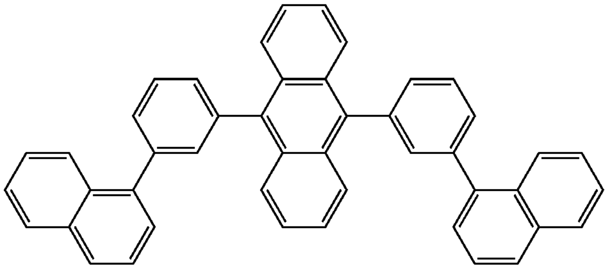

-continued
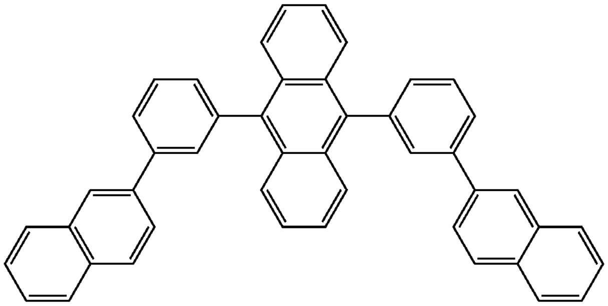
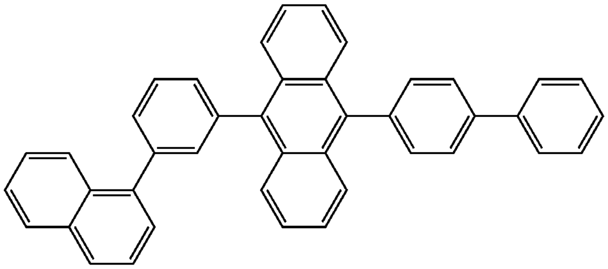
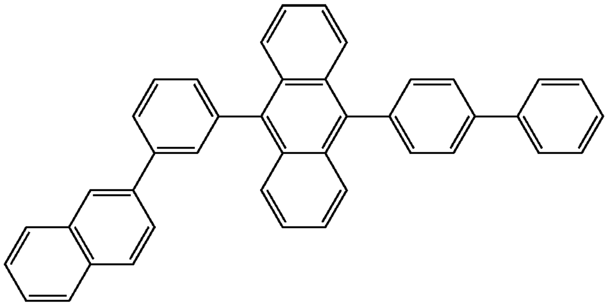
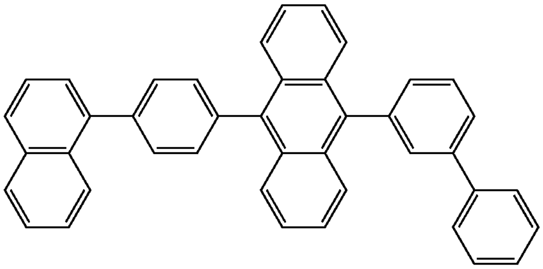
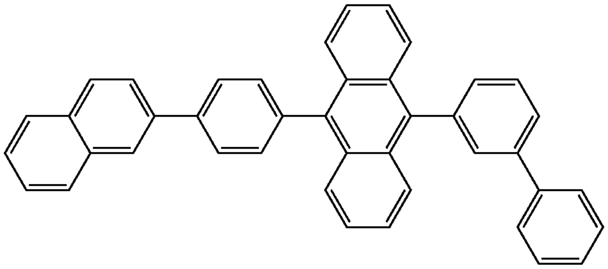
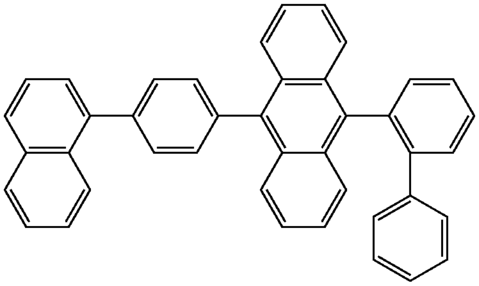
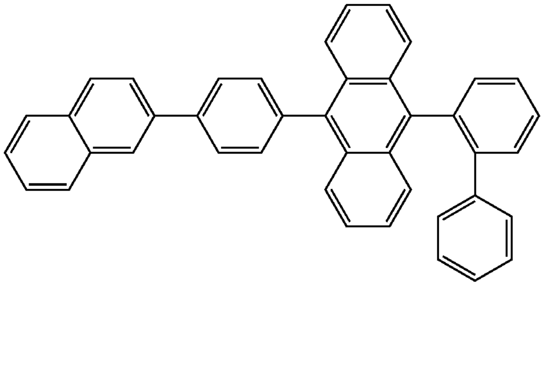
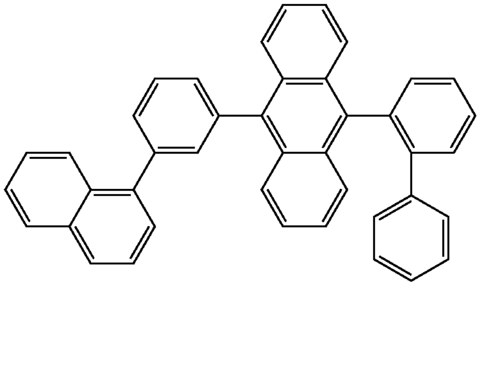

-continued
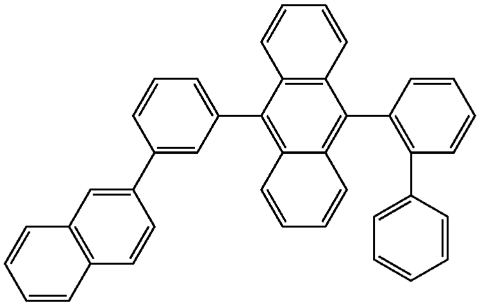
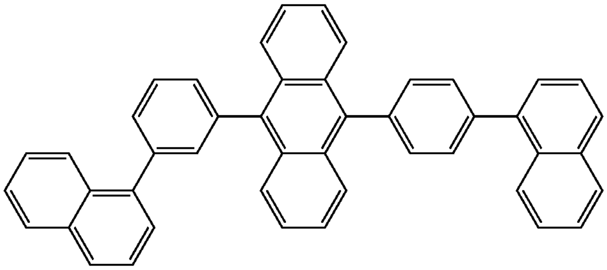
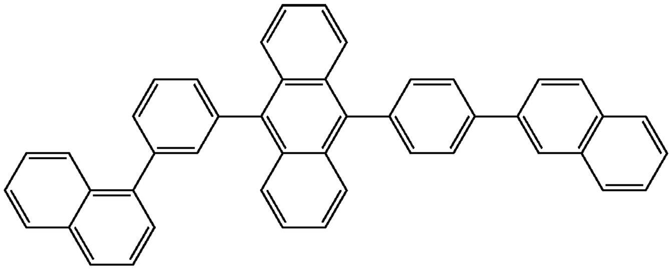
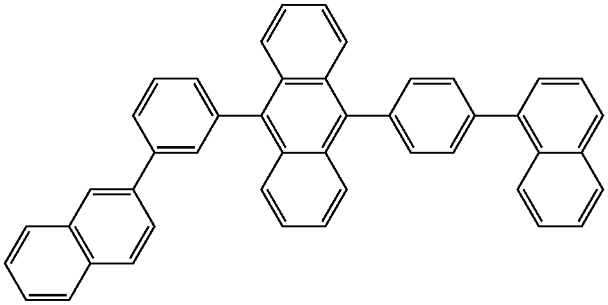
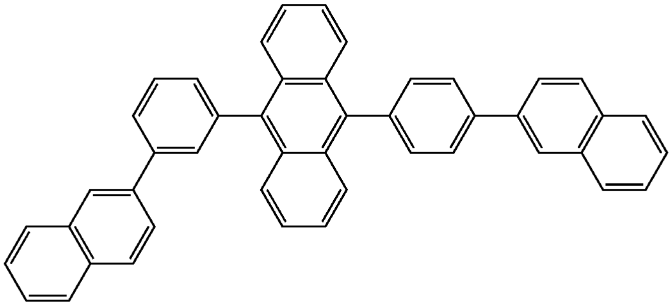
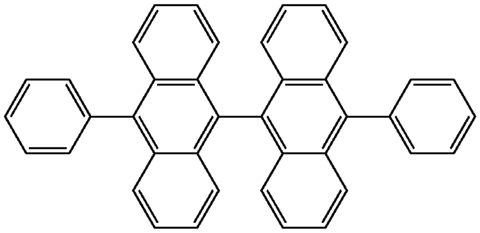
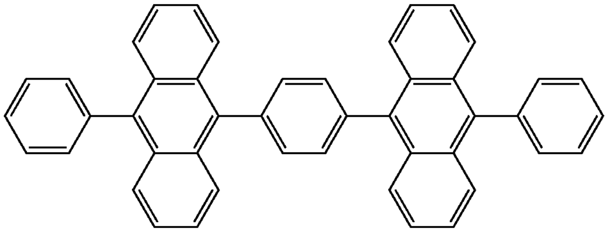
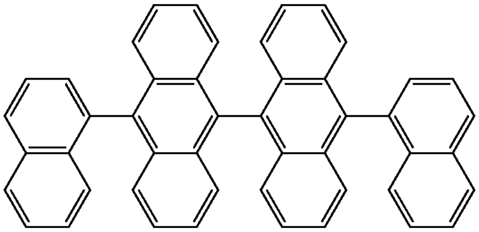
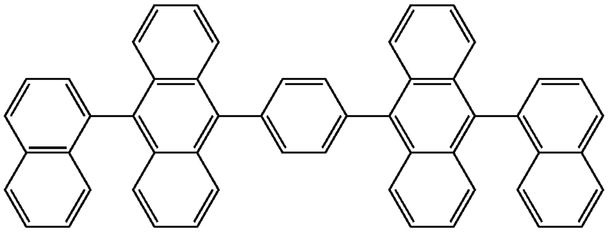

-continued
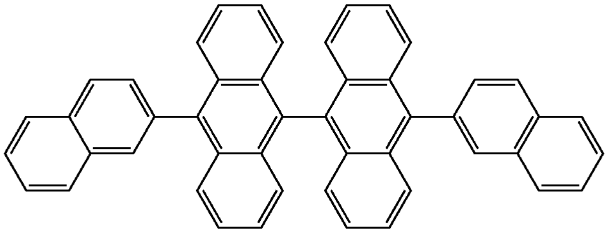
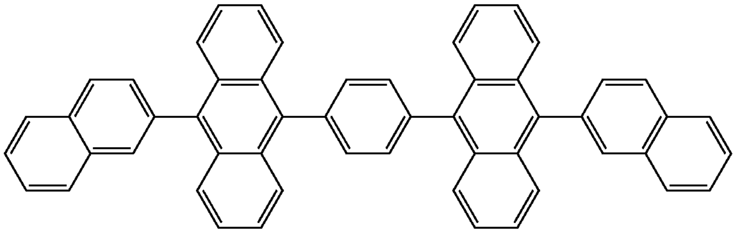
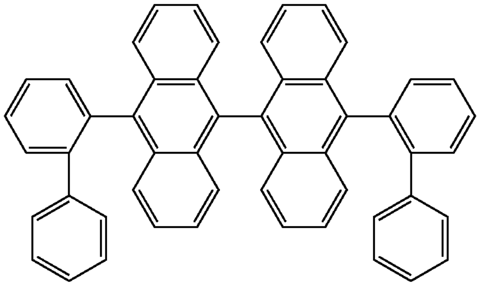
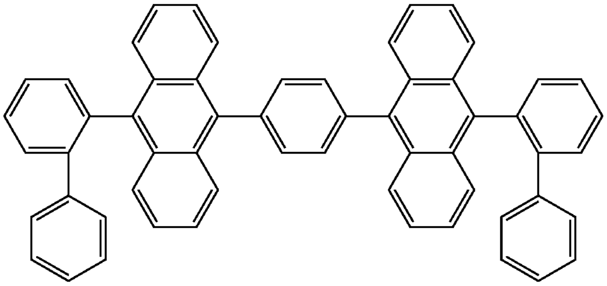
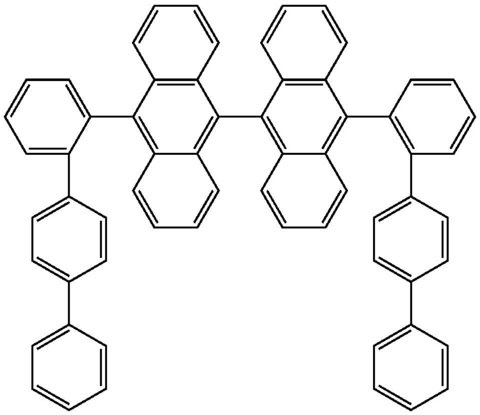
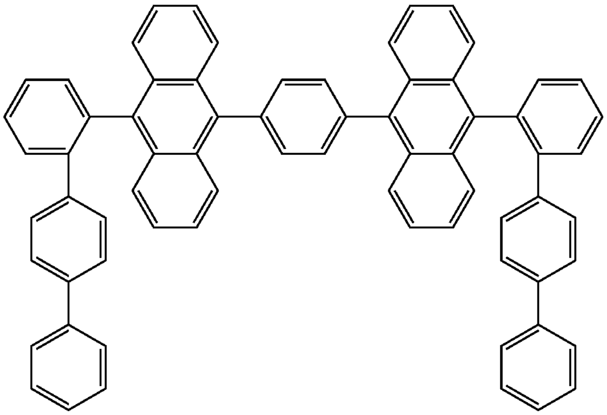
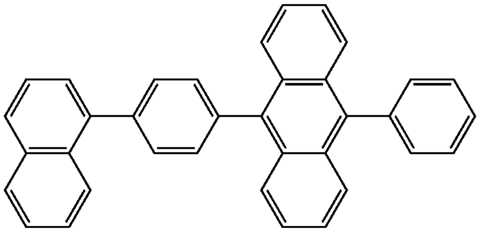
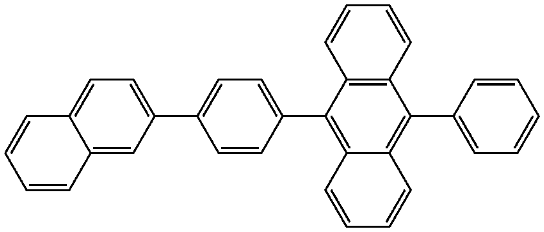
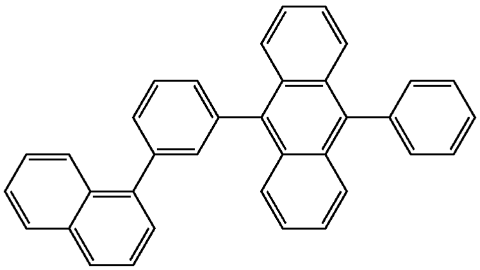
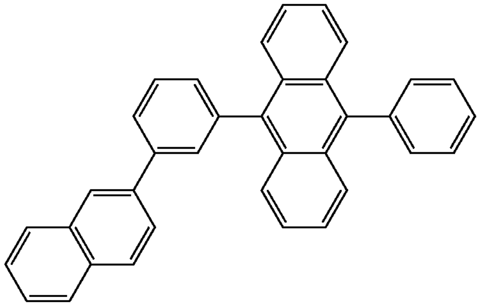

-continued
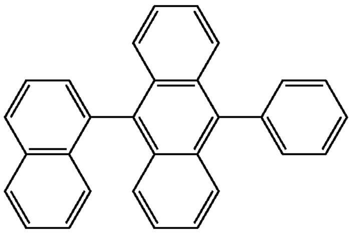
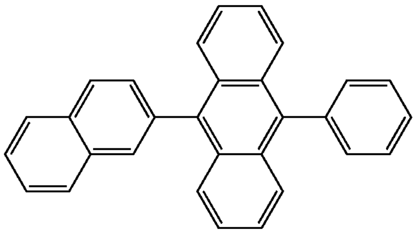
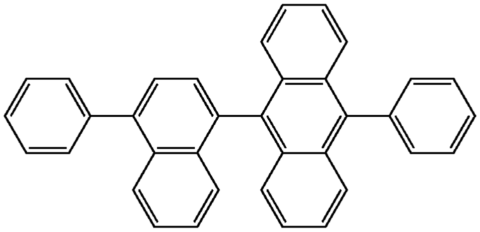
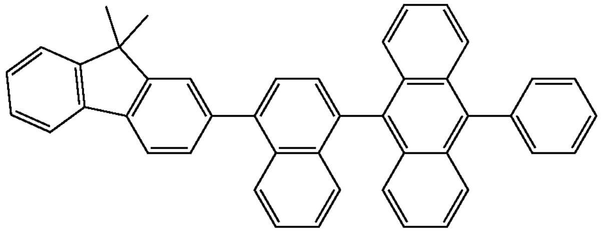
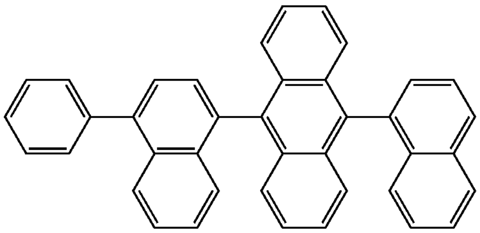
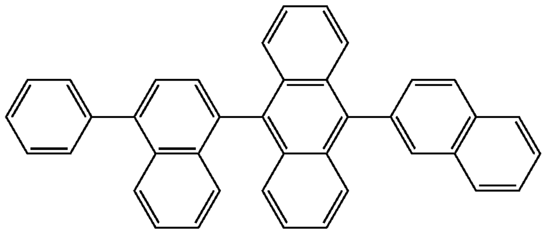
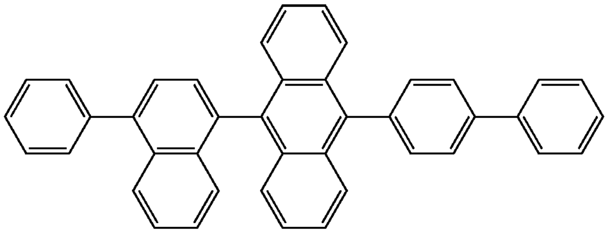
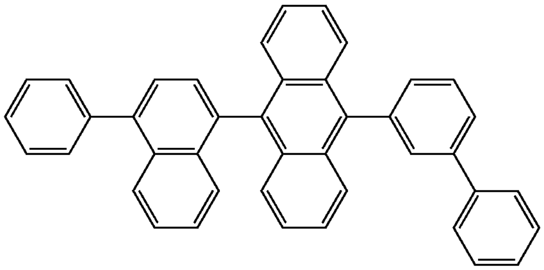
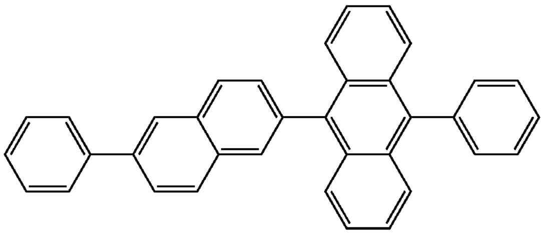
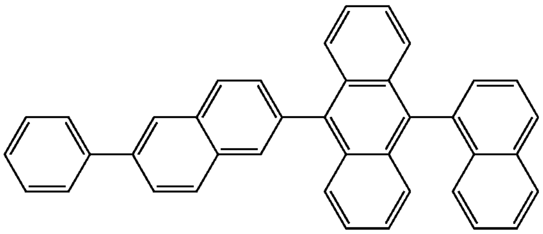
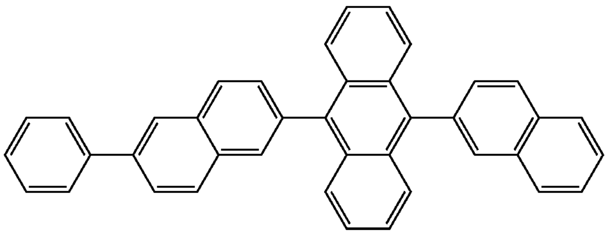
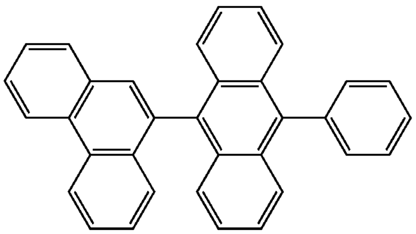
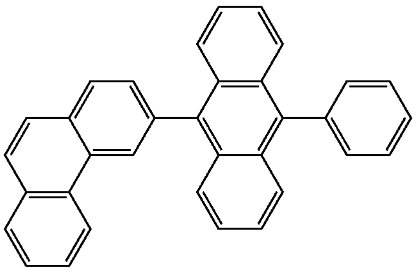
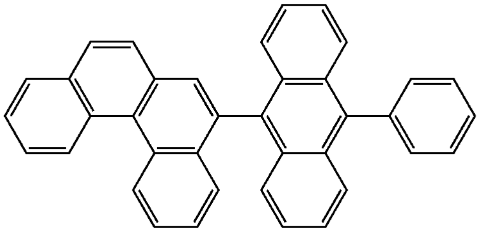

-continued
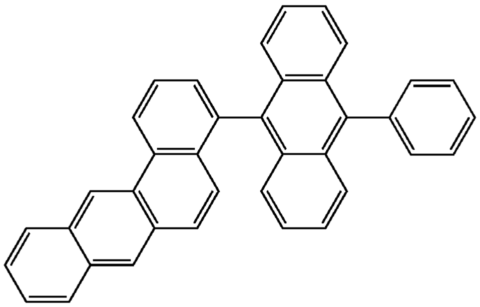
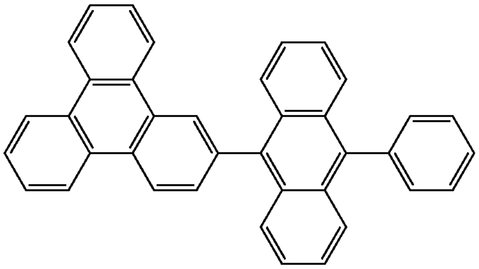
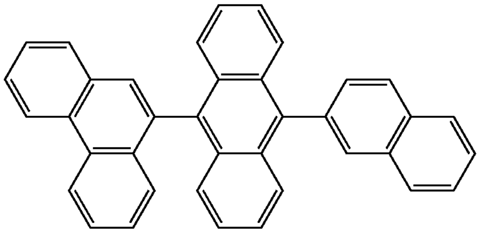
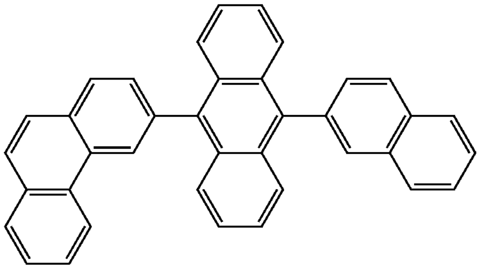
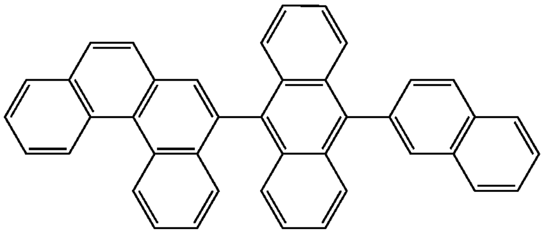
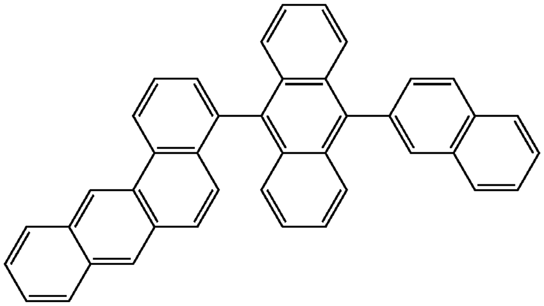
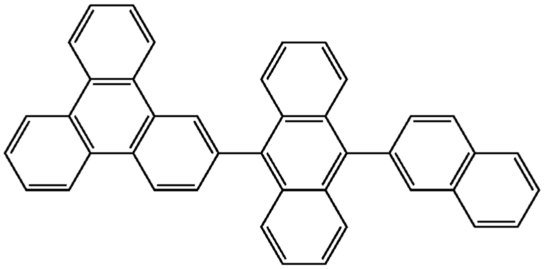
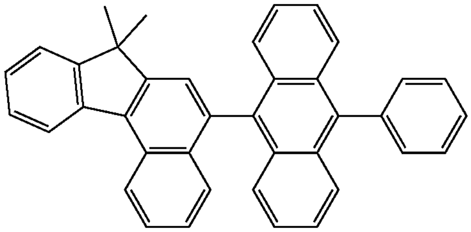
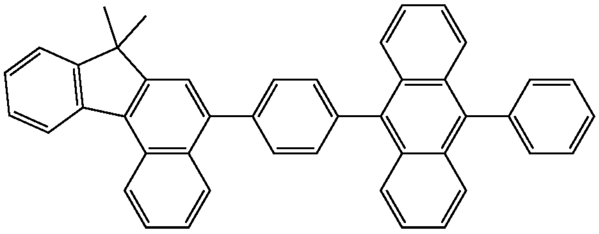
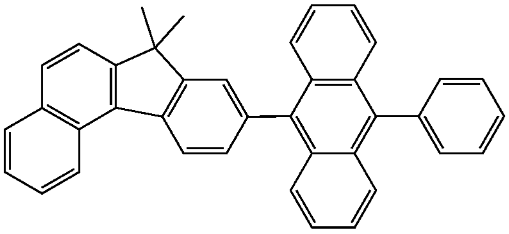
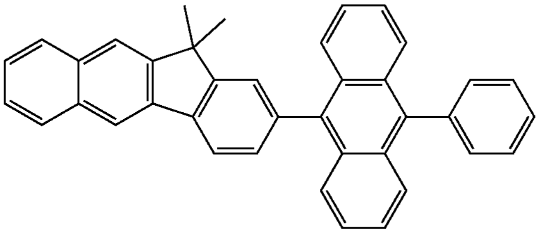
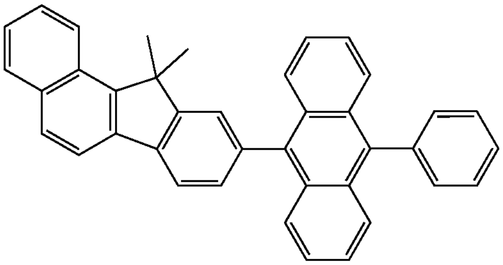

-continued
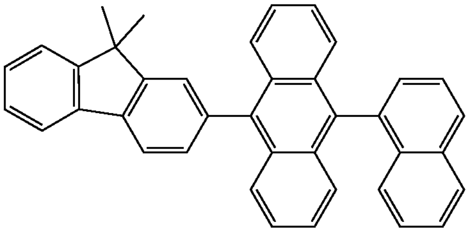
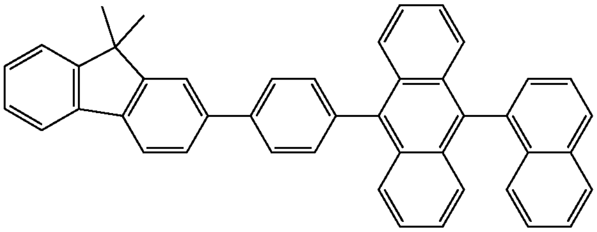
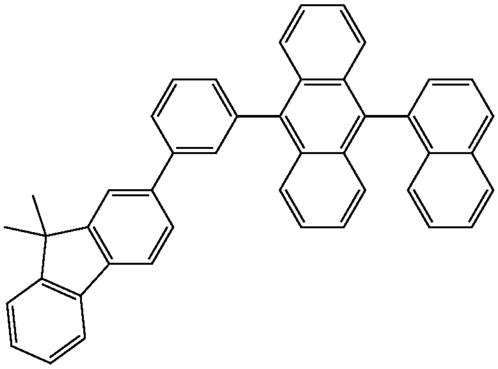
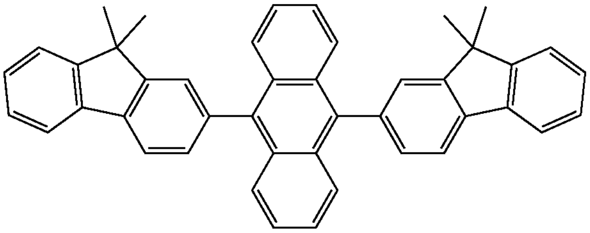
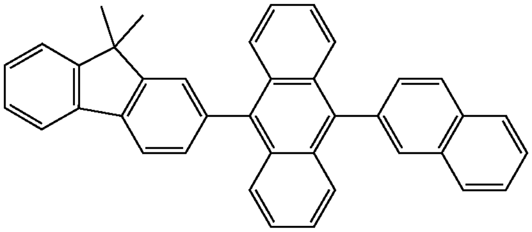
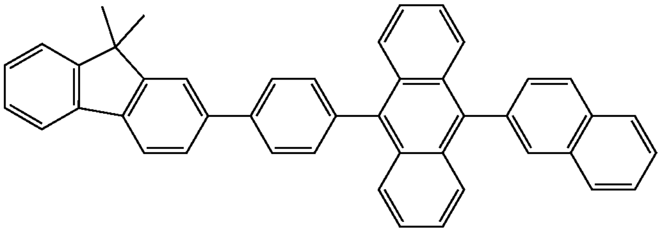
[Chem. 71]
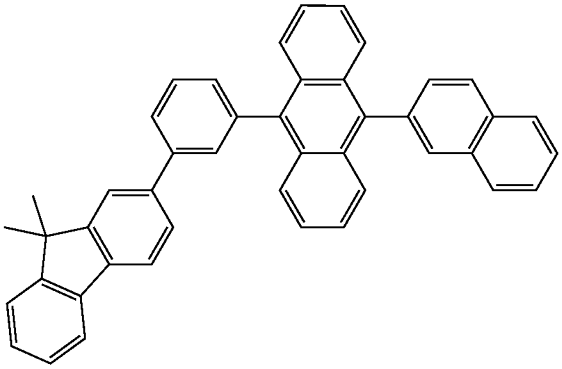
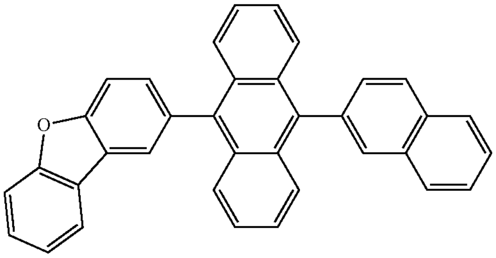

-continued
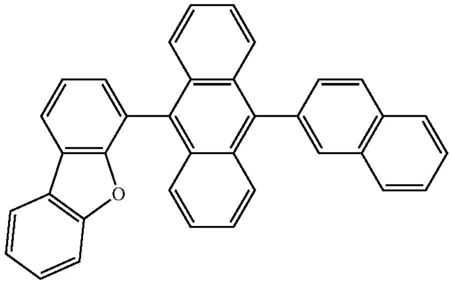
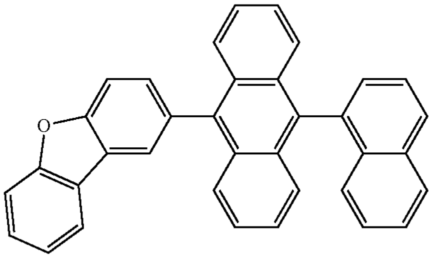
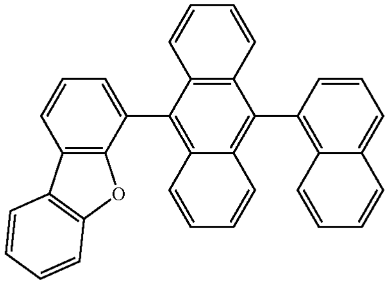
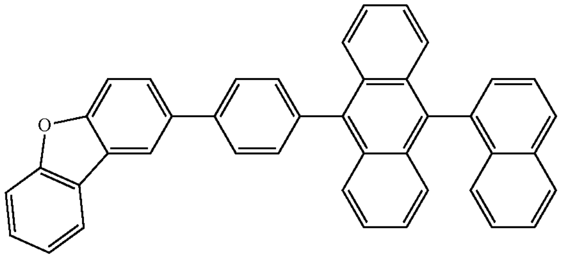
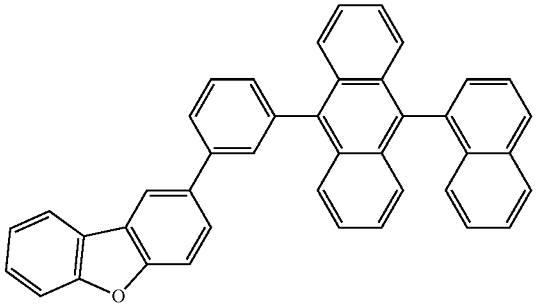
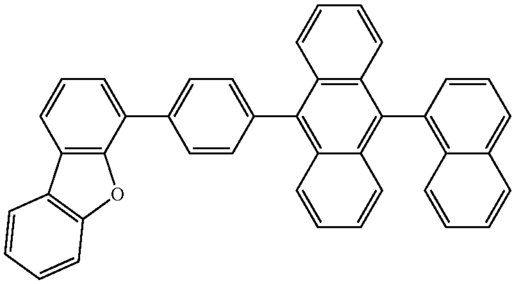
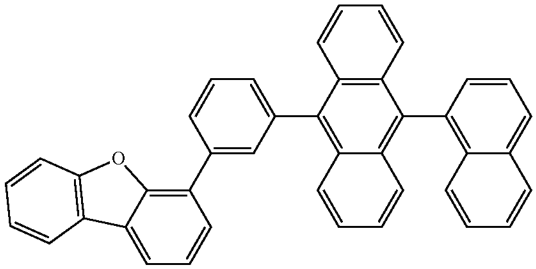
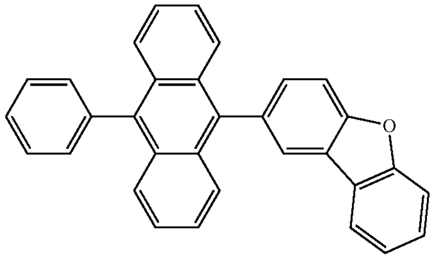
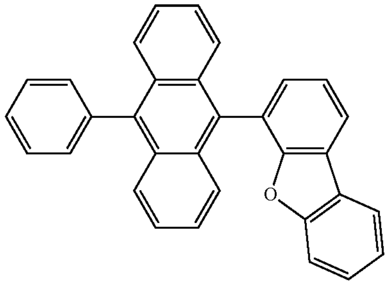
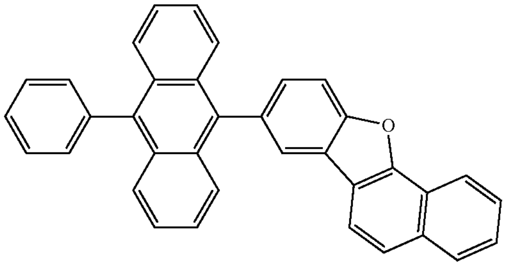

-continued
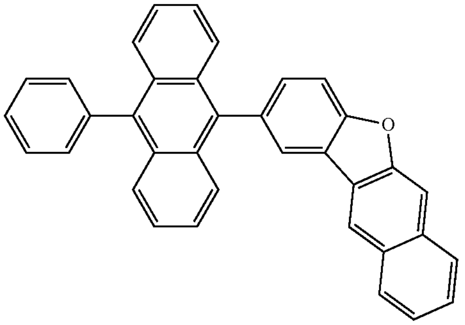
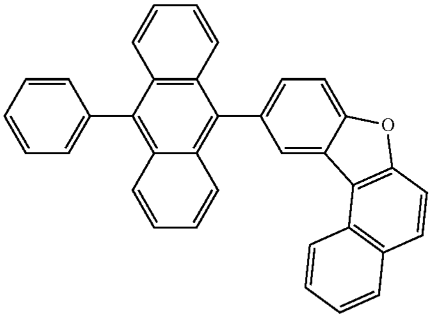
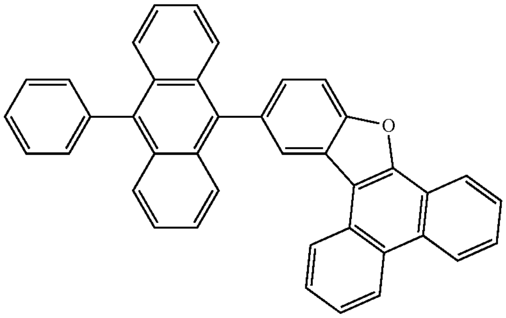
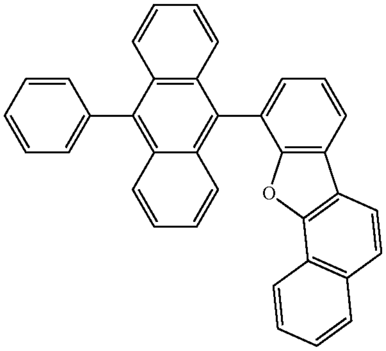
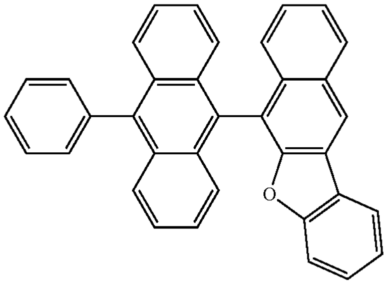
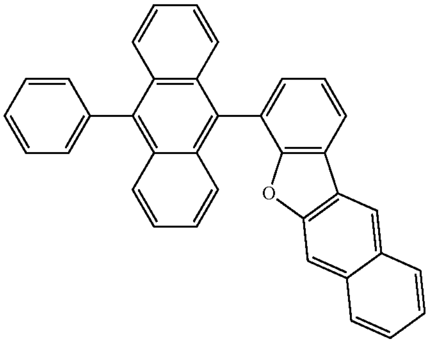
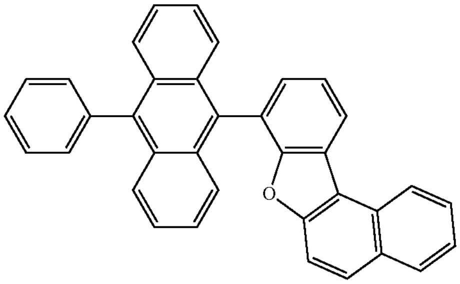
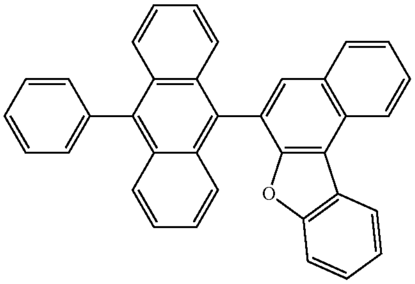
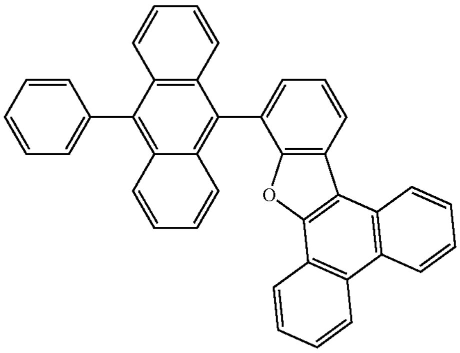
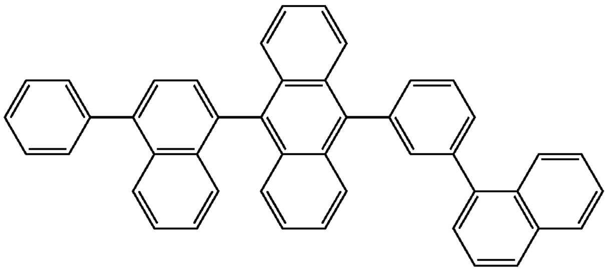

-continued
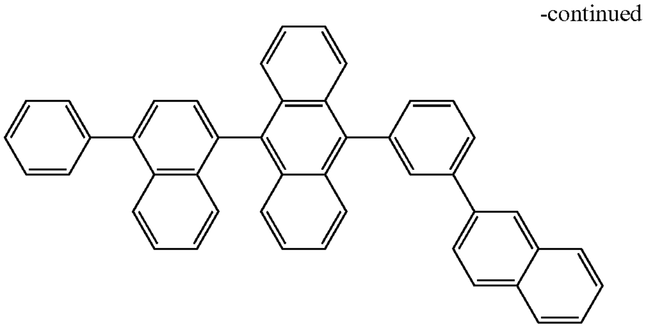
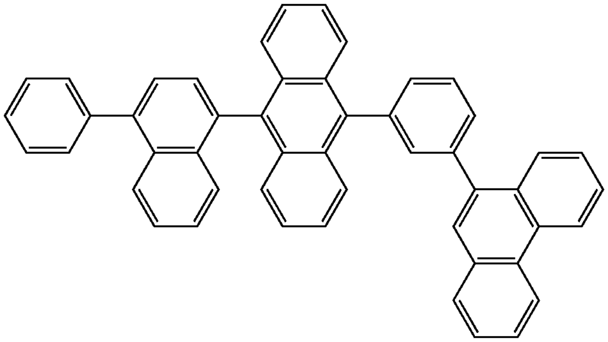
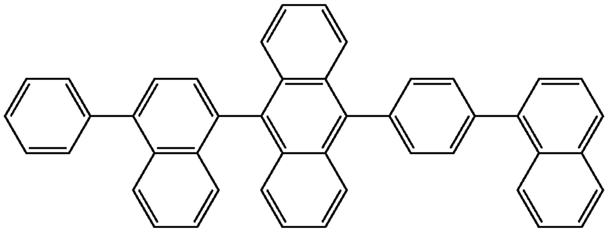
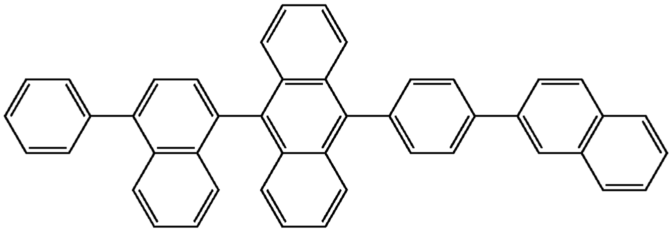
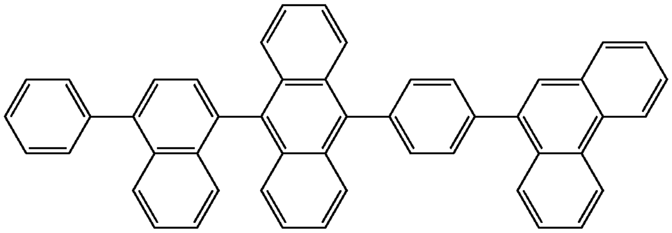
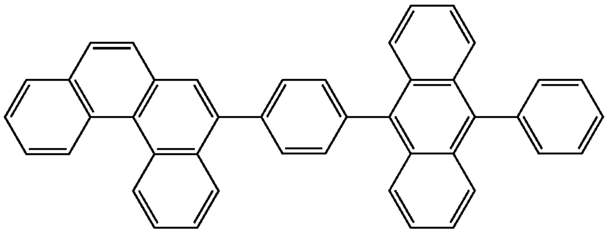
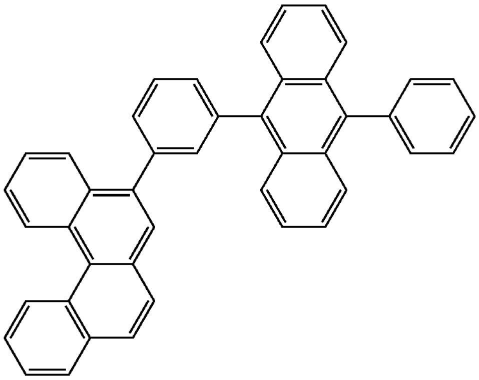

-continued

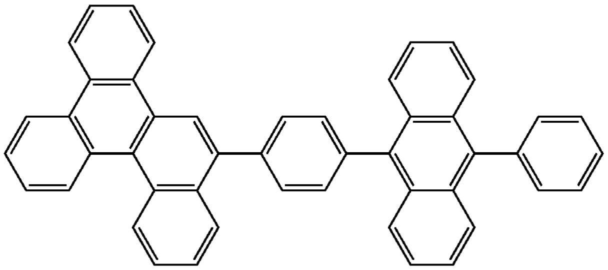

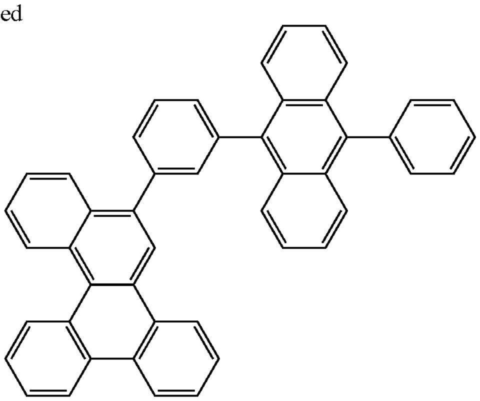

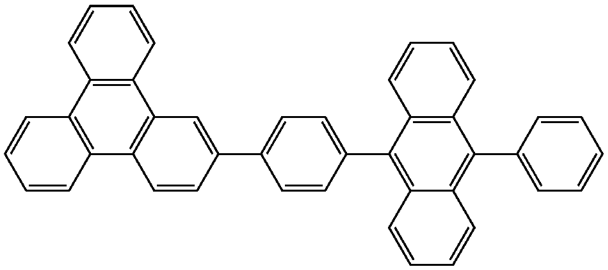

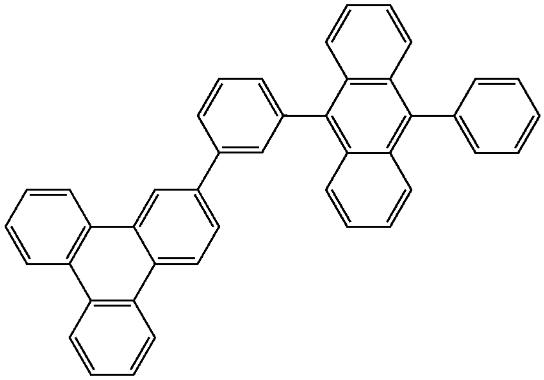

Electron Transport Layer

The electron transport layer is a layer containing a material having a high electron transport property (electron transporting material), and is formed between the light emitting layer and the cathode, or between an electron injection layer, if present, and the light emitting layer.

The electron transport layer may have a monolayer structure or a multilayer structure. For example, the electron transport layer may have a two-layer structure including a first electron transport layer (on the anode side) and a second electron transport layer (on the cathode side). In an aspect of the present invention, the electron transport layer of the monolayer structure is preferably adjacent to the light emitting layer, or the electron transport layer nearest to the anode in the multilayer structure, for example, the first electron transport layer in the two-layer structure is preferably adjacent to the light emitting layer. In another aspect of the present invention, a hole blocking layer as described later or the like may be interposed between the electron transport layer of the monolayer structure and the light emitting layer, or between the electron transport layer nearest to the light emitting layer in the multilayer structure and the light emitting layer.

The inventive compound is used as a material of an electron transport zone, preferably a material of an electron injection layer, an electron transport layer, a hole blocking layer, or an exciton blocking layer, more preferably a material of an electron injection layer or an electron transport layer, and further preferably a material of an electron transport layer.

In the electron transport layer in the two-layer structure, the inventive compound may be contained in one of the first electron transport layer and the second electron transport layer, or may be contained in both. In an aspect of the present invention, the inventive compound is preferably contained only in the first electron transport layer, in another aspect, the inventive compound is preferably contained only in the second electron transport layer, and in another aspect, the inventive compound is preferably contained in the first electron transport layer and in the second electron transport layer.

Examples of the material of the electron transport layer other than the inventive compound include, (1) metal complexes, such as an aluminum complex, a beryllium complex, and a zinc complex, (2) heteroaromatic compounds, such as an imidazole derivative, a benzimidazole derivative, an azine derivative, a carbazole derivative, and a phenanthroline derivative, and (3) high molecular compounds.

Examples of the metal complex include tris(8-quinolinolato)aluminum(III) (abbreviation: Alq), tris(4-methyl-8-quinolinolato)aluminum (abbreviation: Almq3), bis(10-hydroxybenzo[h]quinolinato)beryllium (abbreviation: $BeBq_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc (II) (abbreviation: ZnPBO), and bis[2-(2-benzothiazolyl) phenolato]zinc(II) (abbreviation: ZnBTZ).

Examples of the heteroaromatic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazol-2-yl)stilbene (abbreviation: BzOs).

Examples of the high molecular compound include poly[(9,9-dihexylfluorene-2,7-diyl)-co-(pyridine-3,5-diyl)] (abbreviation: PF-Py), and poly[(9,9-diioctylfluorene-2,7-diyl)-co-(2,2'-bipyridine-6,6'-diyl)] (abbreviation: PF-BPy).

The materials are materials having an electron mobility of $10^{-6}$ $cm^2/Vs$ or more. Any material other than the above materials may be used in an electron transport layer as long as it has a higher electron transport property rather than the hole transport property.

Electron Injection Layer

The electron injection layer is a layer containing a material having a high electron injection property. As the electron injection layer, an alkali metal, such as lithium (Li) or cesium (Cs), an alkaline earth metal, such as magnesium (Mg), calcium (Ca), or strontium (Sr), or a rare earth metal, such as europium (Eu) or ytterbium (Yb), or a compound containing such a metal can be used. Examples of the compound include an alkali metal oxide, an alkali metal halide, an alkali metal-containing organic complex, an alkaline earth metal oxide, an alkaline earth metal halide, an alkaline earth metal-containing organic complex, a rare earth metal oxide, a rare earth metal halide, and a rare earth metal-containing organic complex. Two or more of the compounds can be used in mixture.

Besides, a material having an electron transport property in which an alkali metal, an alkaline earth metal, or a compound thereof is incorporated, specifically Alq in which magnesium (Mg) is incorporated, and the like may be used. In this case, injection of electrons from the cathode can be achieved in more efficient manner.

Alternatively a composite material obtained by mixing an organic compound and an electron donor into an electron injection layer may be used. Such a composite material is superior in electron injection property and electron transport property since the organic compound receives electrons from the electron donor. In this case, the organic compound is preferably a material superior in transport of the received electrons, and specifically for example, a material constituting the electron transport layer described above (metal complex, heteroaromatic compound, etc.) can be used. The electron donor may be any material that has an electron donicity to an organic compound. Specifically an alkali metal, an alkaline earth metal, and a rare earth metal are preferred, and examples thereof include lithium, cesium, magnesium, calcium, erbium, and ytterbium. In addition, an alkali metal oxide and an alkaline earth metal oxide are preferred, and examples thereof include lithium oxide, calcium oxide, and barium oxide. A Lewis base, such as magnesium oxide, can also be used. An organic compound, such as tetrathiafulvalene (abbreviation: TTF), can also be used.

Cathode

For the cathode, a metal, an alloy or a conductive compound which have a low work function (specifically 3.8 eV or lower), a mixture thereof, or the like is preferably used. Specific examples of such cathode materials include an element belonging to Group I or Group II of the periodic table, specifically an alkali metal, such as lithium (Li) or cesium (Cs), and an alkaline earth metal, such as magnesium (Mg), calcium (Ca), or strontium (Sr), and an alloy containing the metals (for example, MgAg, AlLi), a rare earth metal, such as europium (Eu) or ytterbium (Yb), and an alloy containing the metals.

When an alkali metal, an alkaline earth metal, or an alloy containing the metals is used to form a cathode, a vacuum vapor deposition method or a sputtering method can be used. When silver paste or the like is used, a coating method, an inkjet method, or the like can be used.

By providing the electron injection layer, regardless of the level of the work function, various conductive materials, such as Al, Ag, ITO, graphene, silicon, and indium oxide-tin oxide containing silicon oxide, can be used to form a cathode. The conductive material can be formed into a film using a sputtering method, an inkjet method, a spin coating method, or the like.

Insulating Layer

The organic EL device is likely to undergo pixel defect due to a leakage or a short circuit since electric field is applied on an ultra-thin layer. In order to prevent the pixel defect, an insulating layer of an insulating thin film layer may be inserted between a pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or multilayered product of the materials may also be used.

Space Layer

The space layer is a layer that is provided, for example, when a fluorescent light emitting layer and a phosphorescent light emitting layer are laminated, between the fluorescent light emitting layer and the phosphorescent light emitting layer for the purpose not to allow excitons generated in the phosphorescent light emitting layer to diffuse into the fluorescent light emitting layer, or for the purpose of controlling the carrier balance. The space layer can also be provided between a plurality of phosphorescent light emitting layers.

Since the space layer is provided between the light emitting layers, the space layer is preferably of a material having both of an electron transport property and a hole transport property. For preventing diffusion of the triplet energy in phosphorescent light emitting layers adjacent to each other, the triplet energy is preferably 2.6 eV or higher. Examples of the material used for the space layer include the same materials as those used for the hole transport layer described above.

Blocking Layer

A blocking layer, such as an electron blocking layer, a hole blocking layer, or an exciton blocking layer, may be provided adjacent to the light emitting layer. The electron blocking layer is a layer that prevents leakage of electrons from a light emitting layer to a hole transport layer, and the hole blocking layer is a layer that prevents leakage of holes from a light emitting layer to an electron transport layer. The exciton blocking layer has a function to prevent diffusion of excitons generated in a light emitting layer into layers around the light emitting layer to confine the excitons in the light emitting layer.

Each layer in the organic EL device can be formed by a conventionally known vapor deposition method, coating method, or the like. For example, each layer can be formed by a known method, for example, a vapor deposition method, such as a vacuum vapor deposition method or a molecular beam epitaxy method (MBE method), or a coating method, such as a dipping method, a spin coating method, a casting method, a bar-coating method, or a roll-coating method, using a solution of a compound for forming the layer.

The thickness of each layer is not particularly limited. However, in general, a too small thickness is likely to cause pinholes or other defects, and a too large thickness requires a high driving voltage to worsen the efficiency and thus, the thickness is preferably 5 nm to 10 μm, and more preferably 10 nm to 0.2 μm.

The organic EL device can be used for an electronic appliance, such as a display member of an organic EL panel module or the like, a display unit of a television, a cellular phone, or a personal computer, and a luminescence unit of an illumination or a vehicle luminaire.

EXAMPLES

The present invention will be described in more detail below with reference to examples, but the present invention is not to be limited to the following examples.

Inventive Compounds Used in Production of Organic EL Devices of Examples 1 to 5

Inv-1

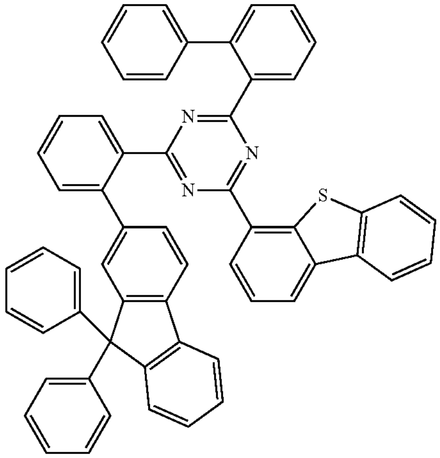

Inv-2

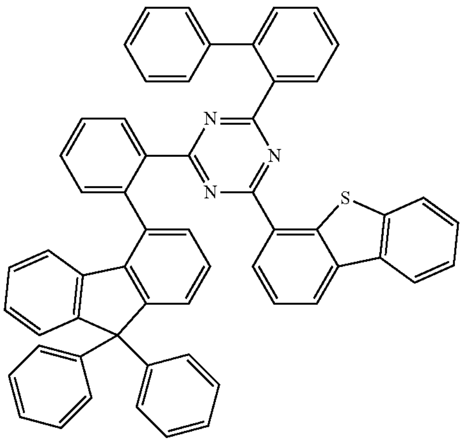

-continued

Inv-3

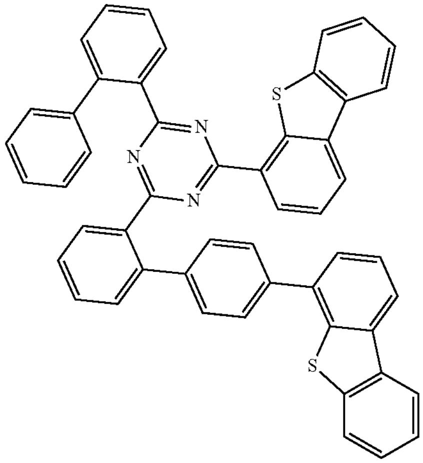

Inv-4

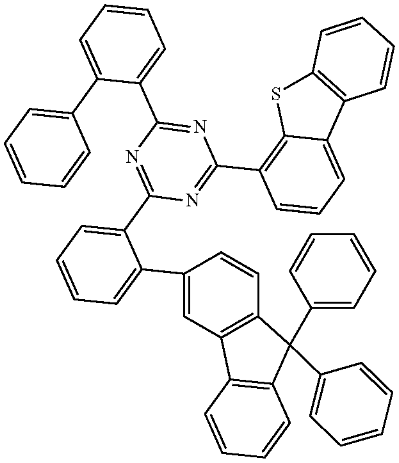

Inv-5

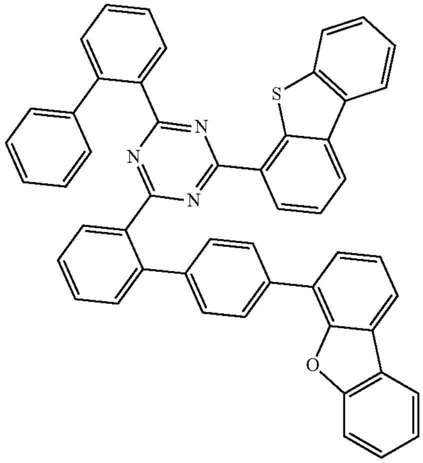

Comparative compounds used in production of organic EL devices of Comparative Examples 1 to 2
Ref-1
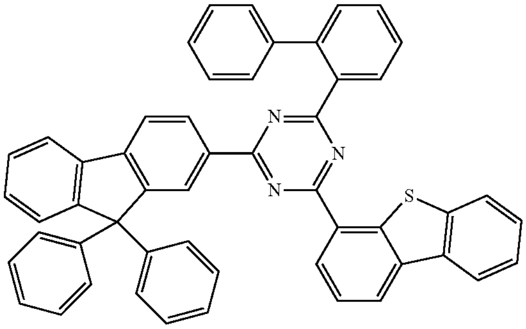
Ref-2
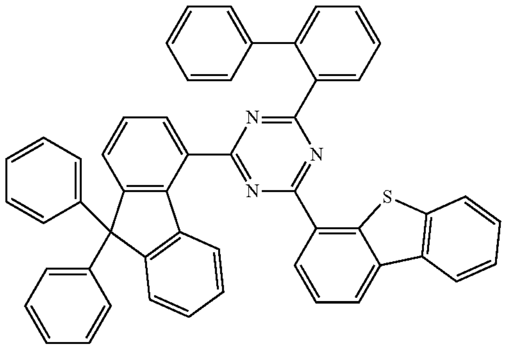
The comparative compounds Ref-1 and Ref-2 are compounds described in PTL 8.
Other compounds used in production of organic EL devices of Examples 1 to 5 and Comparative Examples 1 to 2
HI-1
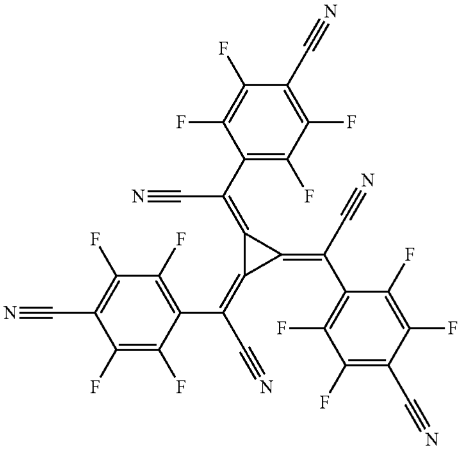
-continued
HT-1
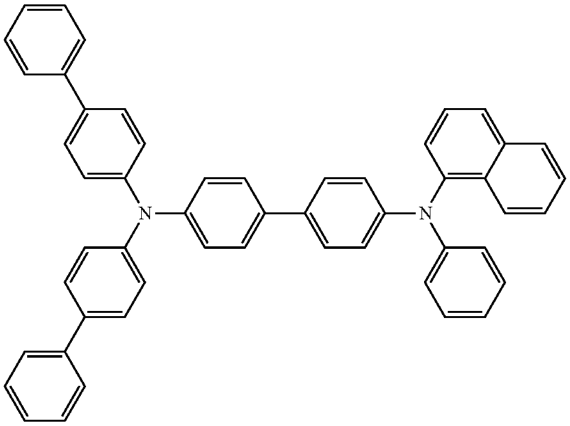
EBL-1
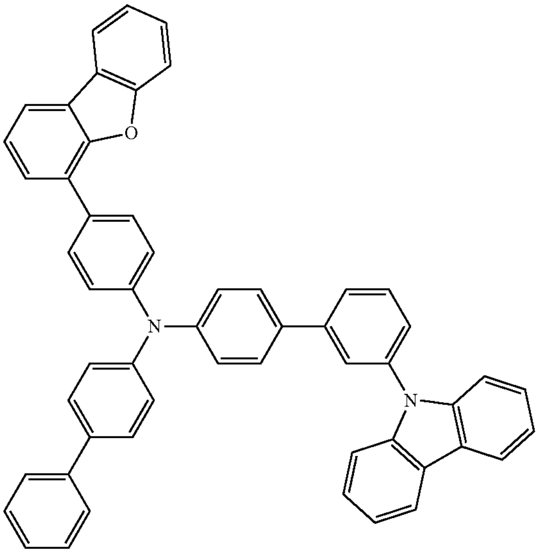
BH-1
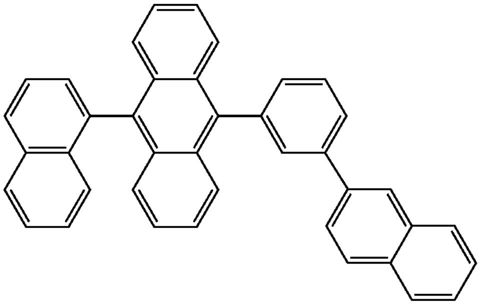
BD-1
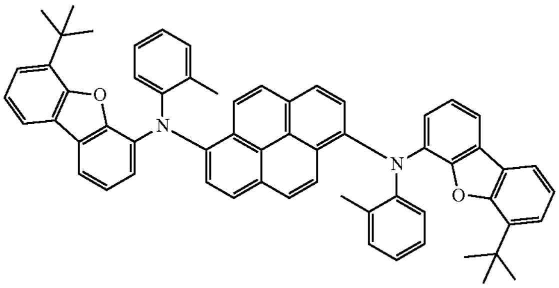

-continued

HBL-1

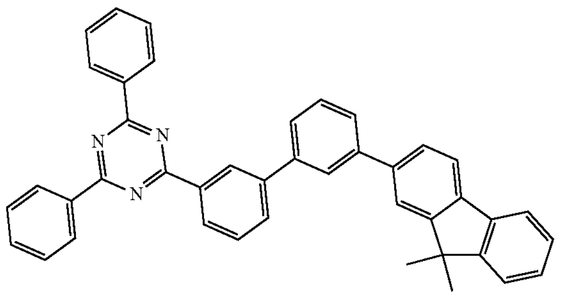

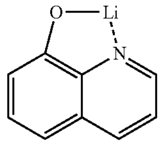

Liq

Each organic EL device was produced as follows and the EL device performance of each device was evaluated.

Production of Organic EL Device

Example 1

A glass substrate with an ITO transparent electrode (anode) of 25 mm×75 mm×1.1 mm (manufactured by GEOMATEC Co., Ltd.) was subjected to ultrasonic cleaning in isopropyl alcohol for 5 minutes, followed by UV ozone cleaning for 30 minutes. The thickness of the ITO film was 130 nm.

The washed glass substrate with a transparent electrode was mounted on a substrate holder of a vacuum vaper deposition apparatus, and first, a compound HT-1 and a compound HI-1 were co-deposited on a surface on which the transparent electrode was formed so as to cover the transparent electrode to thus form a hole injection layer having a thickness of 10 nm. The mass ratio of the compound HT-1 and the compound HI-1 was 97:3.

Next, the compound HT-1 was deposited on the hole injection layer to form a first hole transport laver having a thickness of 80 nm.

A compound EBL-1 was deposited on the first hole transport layer to form a second hole transport layer having a thickness of 5 nm.

Next, a compound BH-1 (host material) and a compound BD-1 (dopant material) were co-deposited on the second hole transport layer to form a light emitting layer having a thickness of 25 nm. The mass ratio of the compound BH-1 and the compound BD-1 was 96:4.

Next, a compound HBL-1 was deposited on the light emitting layer to form a first electron transport layer having a thickness of 5 nm.

A compound Inv-1 and Liq were co-deposited on the first electron transport layer to form a second electron transport layer having a thickness of 20 nm. The mass ratio of the compound Inv-1 and Liq was 50:50.

Yb was deposited on the second electron injection layer to form an electron injecting electrode having a thickness of 1 nm.

Finally, a metal Al was deposited on the electrons injecting electrode to form a metal cathode having a thickness of 50 nm.

The layer structure of the organic EL device of Example 1 is shown below. ITO (130)/HT-1:HI-1=97:3 (10)/HT-1 (80)/EBL-1 (5)/BH-1:BD-1=96:4 (25)/HBL-1 (5)/Inv-1:Liq=50:50 (20)/Yb (1)/Al (50)

In this layer structure, the numbers in the parentheses represent the thickness (nm), and the ratio of HT-1 and HI-1, the ratio of BH-1 and BD-1, and the ratio of Inv-1 and Liq are the mass ratio.

Examples 2 to 5 and Comparative Examples 1 to 2

Each organic EL device was produced in the same manner as in Example 1 except for using each compound shown in Table 1 in place of the compound Inv-1.

Evaluation of Organic EL Device: Measurement of External Quantum Efficiency (EQE)

Each organic EL device was driven at a DC constant current at a room temperature and a current density of 10 mA/cm$^2$. The brightness was measured with a brightness photometer (Spectroradiometer CS-1000 manufactured by KONICA MINOLTA, INC.), and based on the result, the external quantum efficiency (%) was determined. The results are shown in Table 1.

TABLE 1

| | Material of second electron transport layer | | EQE (%) |
|---|---|---|---|
| Example 1 | Compound Inv-1 | Liq | 10.0 |
| Example 2 | Compound Inv-2 | Liq | 10.1 |
| Example 3 | Compound Inv-3 | Liq | 9.9 |
| Example 4 | Compound Inv-4 | Liq | 9.8 |
| Example 5 | Compound Inv-5 | Liq | 9.9 |
| Comparative Example 1 | Comparative compound Ref-1 | Liq | 9.3 |
| Comparative Example 2 | Comparative compound Ref-2 | Liq | 9.4 |

It is found from the results shown in Table 1 that the compounds of the present invention provide an organic EL device having higher efficiency as compared with the comparative compounds.

Inventive Compounds Used in Production of Organic EL Devices of Examples 6 to 9

Inv-1

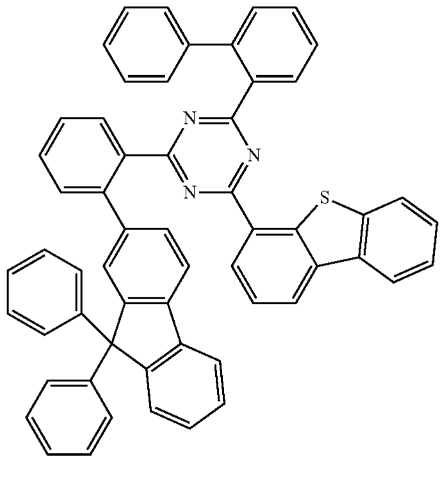

-continued
Inv-6
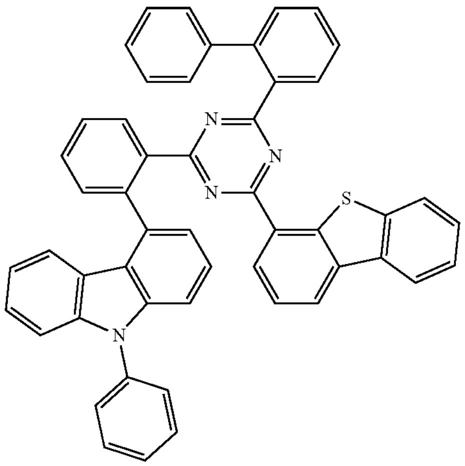
Inv-7
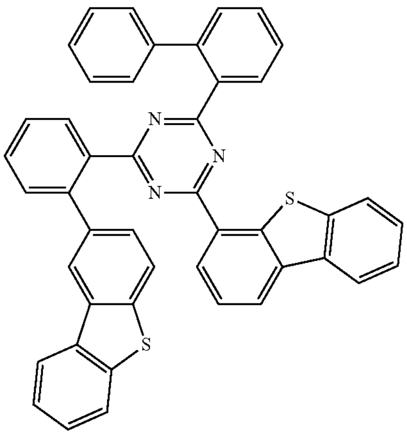
Inv-10
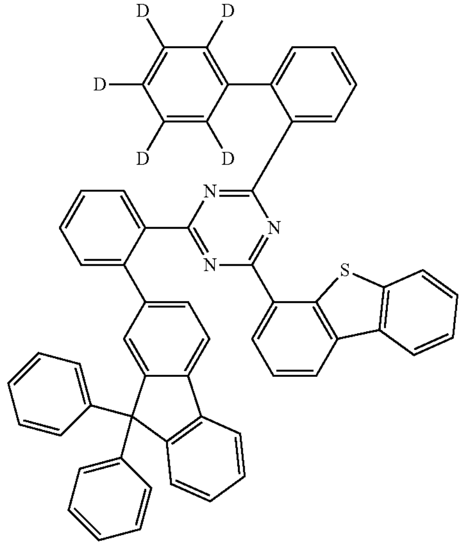
Comparative Compound Used in Production of Organic EL Device of Comparative Example 3
Ref-3
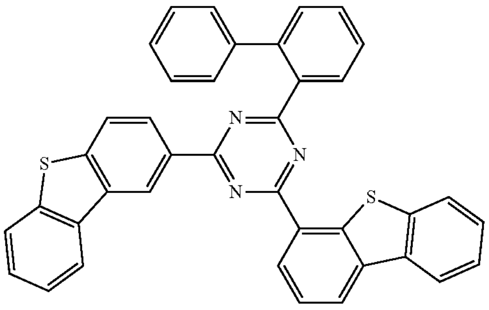
The comparative compound Ref-3 is a compound described in PTL 8.
Other Compounds Used in Production of Organic EL Devices of Examples 6 to 9 and Comparative Example 3
HI-1
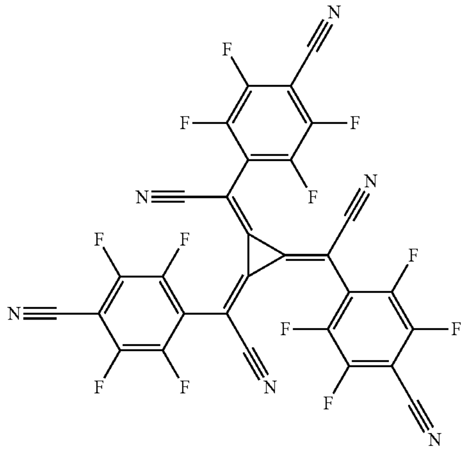
HT-2
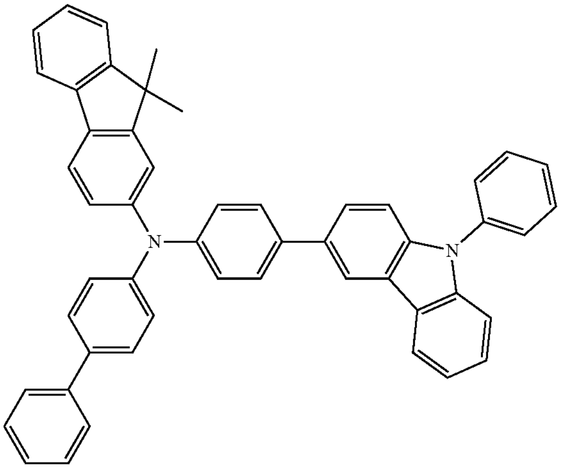

-continued

EBL-1

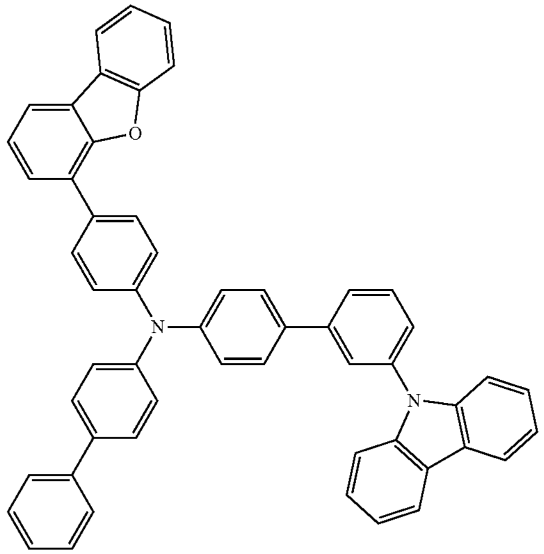

BH-2

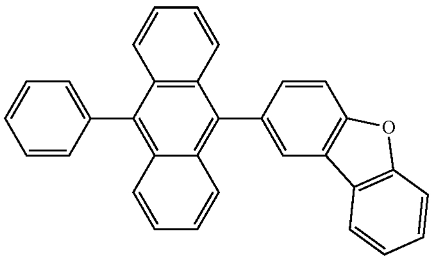

BD-1

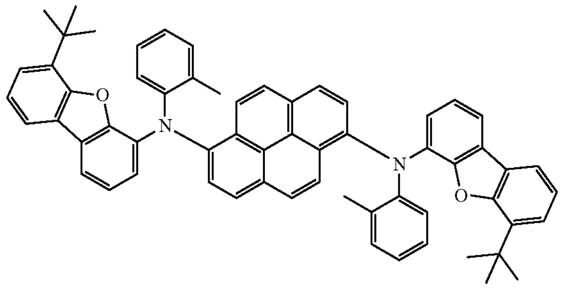

HBL-1

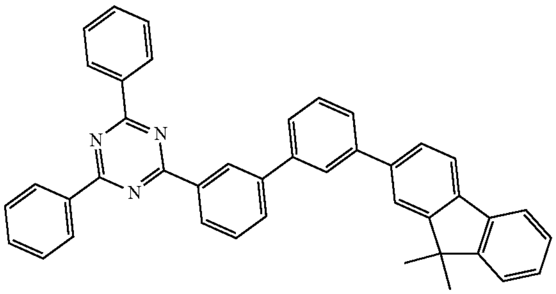

-continued

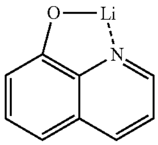

Liq

Each organic EL device was produced as follows and the EL device performance of each device was evaluated.

Production of Organic EL Device

Example 6

An organic EL device was produced in the same manner as in Example 1 except for using a compound HT-2 in place of the compound HT-1 used in the hole injection layer and the first hole transport layer and using a compound BH-2 in place of the compound BH-1.

The layer structure of the obtained organic EL device was shown below. ITO (130)/HT-2:HI-1=97:3 (10)/HT-2 (80)/EBL-1 (5)/BH-2:BD-1=96:4 (25)/HBL-1 (5)/Inv-1:Liq=50:50 (20)/Yb (1)/Al (50)

In the layer structure, the numbers in the parentheses represent the thickness (nm) and the ratio of HT-2 and HI-1, the ratio of BH-2 and BD-1, and the ratio of Inv-1 and Liq are the mass ratio.

Examples 7 to 9 and Comparative Example 3

Each organic EL device was produced in the same manner as in Example 6 except for using each compound shown in Table 2 in place of the compound Inv-1.

Evaluation of Organic EL Device: Measurement of External Quantum Efficiency (EQE)

The external quantum efficiency (%) of each organic EL device was determined in the same manner as above. The results are shown in Table 2.

TABLE 2

| | Material of second electron transport layer | | EQE (%) |
|---|---|---|---|
| Example 6 | Compound Inv-1 | Liq | 9.4 |
| Example 7 | Compound Inv-6 | Liq | 9.5 |
| Example 8 | Compound Inv-7 | Liq | 9.4 |
| Example 9 | Compound Inv-10 | Liq | 9.4 |
| Comparative Example 3 | Comparative compound Ref-3 | Liq | 8.6 |

It is found from the results shown in Table 2 that the compounds of the present invention provide an organic EL device having higher efficiency as compared with the comparative compound.

COMPOUNDS SYNTHESIZED IN SYNTHETIC EXAMPLES
Inv-1
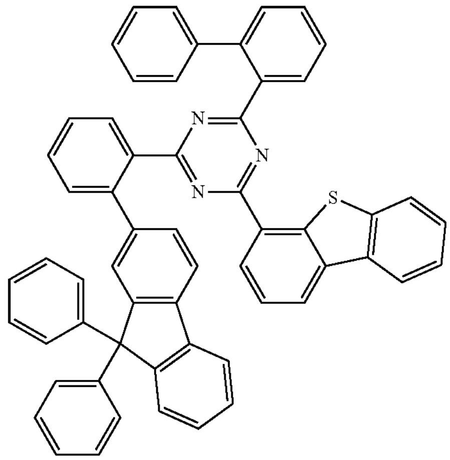
Inv-2
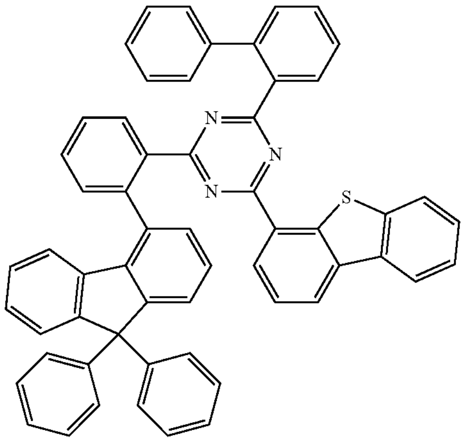
Inv-3
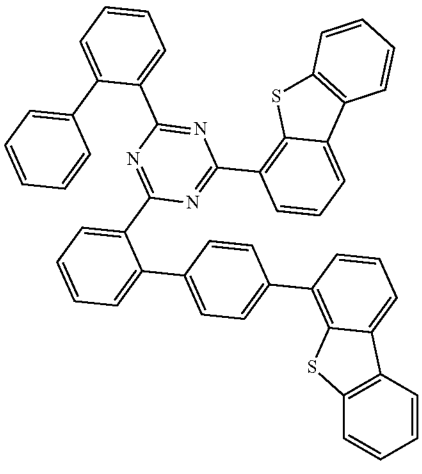
-continued
Inv-4
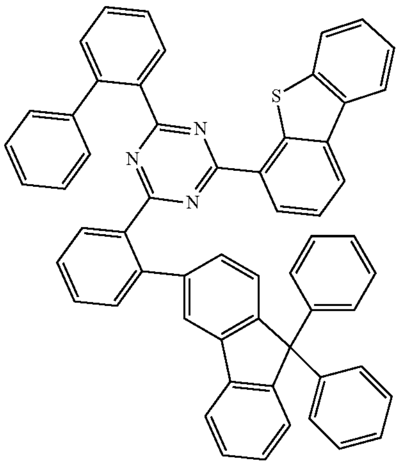
Inv-5
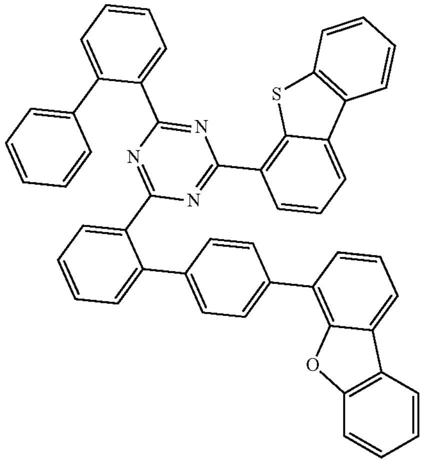
Inv-6
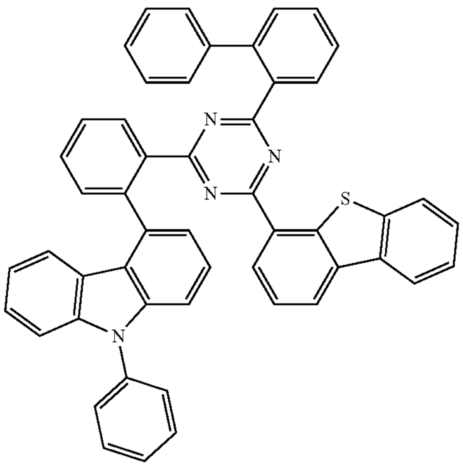

-continued

Inv-7

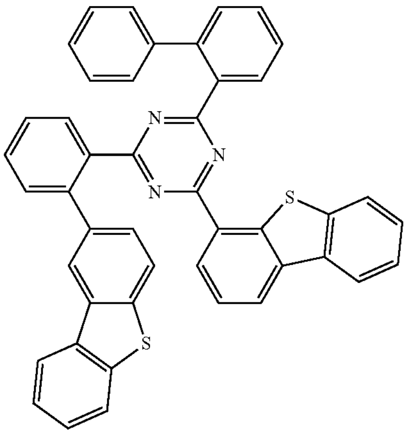

Inv-8

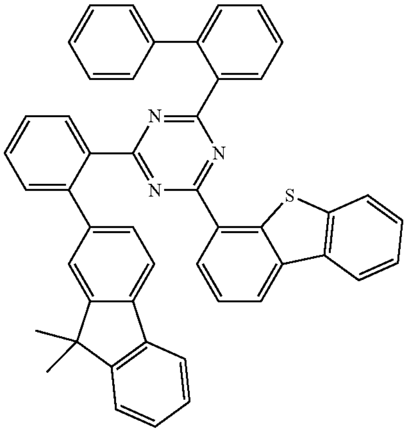

Inv-9

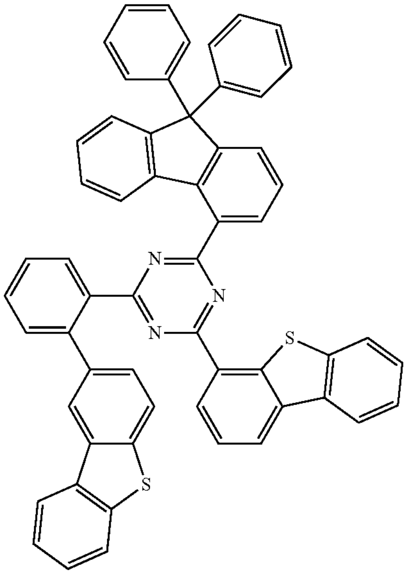

-continued

Inv-10

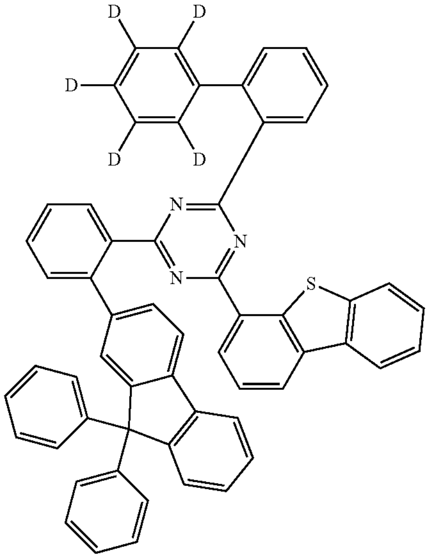

Synthetic Example 1: Synthesis of Compound Inv-1

(1-1) Synthesis of Intermediate A

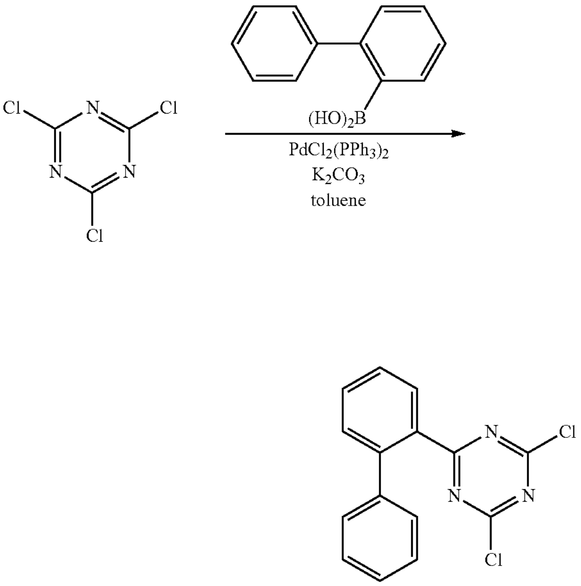

Intermediate A

Cyanuric chloride (10 g) and biphenyl-2-boronic acid (7.2 g) were added to toluene (180 mL), and argon gas was injected into the obtained solution for 5 minutes. Dichloro-bis(triphenylphosphine)palladium (0.13 g) and potassium carbonate (20 g) were added thereto, and the mixture was heated at 60° C. for 20 hours with stirring under an argon atmosphere. The reaction solution was filtered to remove inorganic salts. The filtrate was subjected to silica gel column chromatography to obtain an intermediate A (2.3 g, yield 21%).

(1-2) Synthesis of Intermediate B

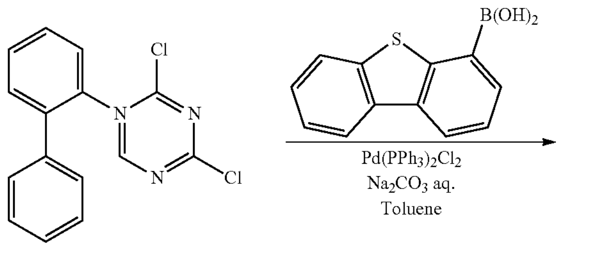

Intermediate A

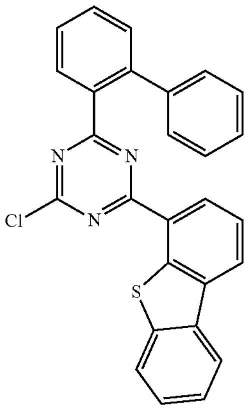

Intermediate B

The intermediate A (2.5 g) and dibenzothiophene-4-boronic acid (1.9 g) were added to toluene (100 mL), and argon gas was injected into the solution for 5 minutes. Dichlorobis (triphenylphosphine)palladium (116 mg) and an aqueous sodium carbonate solution (2 M, 1.2 ml) were added thereto, and the mixture was heated at 55° C. for 10 hours with stirring under an argon atmosphere. The solvent was distilled off from the reaction solution, and the resulting solid was subjected to silica gel column chromatography to obtain an intermediate B (0.7 g, yield 19%).

(1-3) Synthesis of Intermediate C

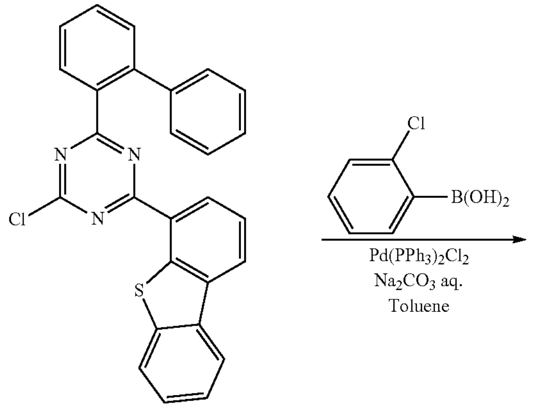

Intermediate B

-continued

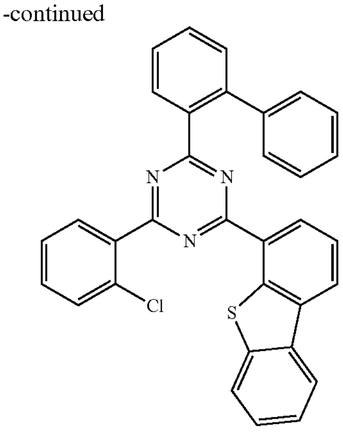

Intermediate C

The intermediate B (25 g) and 2-chlorophenyl boronic acid (8.7 g) were added to toluene (300 mL), and argon gas was injected into the solution for 5 minutes. Dichlorobis (triphenylphosphine)palladium (0.4 g) and an aqueous sodium carbonate solution (2 M, 70 mL) were added thereto, and the mixture was heated at 60° C. for 10 hours with stirring under an argon atmosphere. The solvent was distilled off from the reaction solution, and the resulting solid was subjected to silica gel column chromatography to obtain an intermediate C (23.4 g, yield 80%).

(1-4) Synthesis of Compound Inv-1

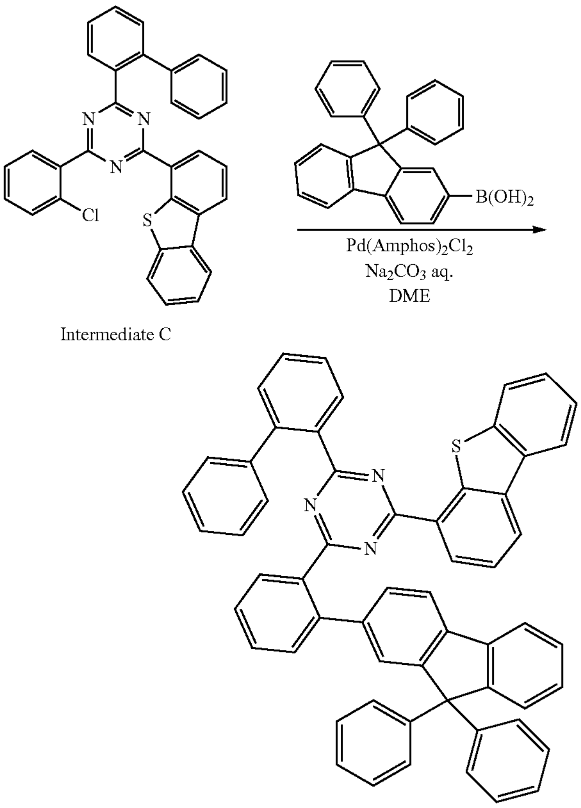

Intermediate C

Inv-1

The intermediate C (4.0 g) and 9,9-diphenylfluorene-2-boronic acid (3.0 g) were added to 1,2-diethoxyethane (DME) (1000 mL), and argon gas was injected into the solution for 5 minutes. $Pd(Amphos)_2Cl_2$ (0.27 g) an aqueous sodium carbonate solution (2 M, 12 mL) were added thereto, and the mixture was heated at 80° C. for 12 hours with stirring under an argon atmosphere. The solvent was distilled off from the reaction solution, and the resulting solid was subjected to column chromatograph to obtain Inv-1 (4.3 g, yield 70%).

Mass spectrometry gave a result of m/e=808, which confirmed that the product was the target compound.

Synthetic Example 2: Synthesis of Compound Inv-2

(2-1) Synthesis of Intermediate D

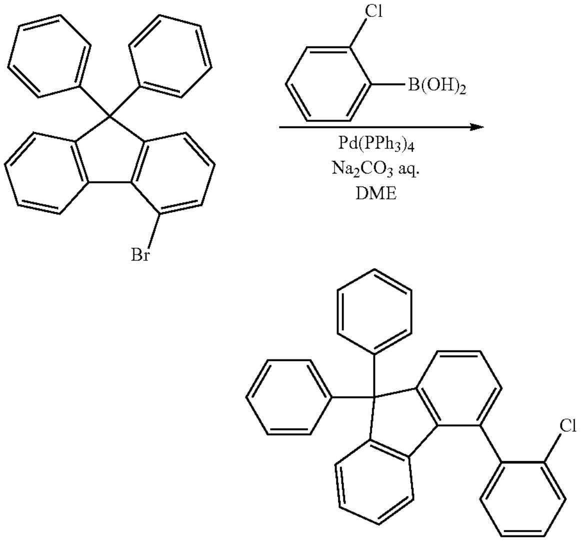

Intermediate D

4-Bromo-9,9-diphenylfluorene (10.0 g) and 2-chlorophenyl boronic acid (4.1 g) were added to 1,2-dimethoxyethane (DME) (200 mL), and argon gas was injected into the solution for 5 minutes. $Pd(PPh_3)_4$ (0.9 g) and an aqueous sodium carbonate solution (2 M, 40 mL) were added thereto, and the mixture was heated at 80° C. for 10 hours with stirring under an argon atmosphere. The solvent was distilled off from the reaction solution, and the resulting solid was subjected to column chromatography to obtain an intermediate D (9.2 g, yield 85%).

(2-2) Synthesis of Intermediate E

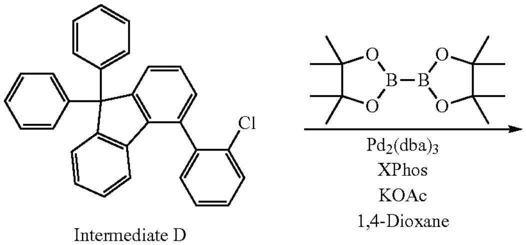

Intermediate D

-continued

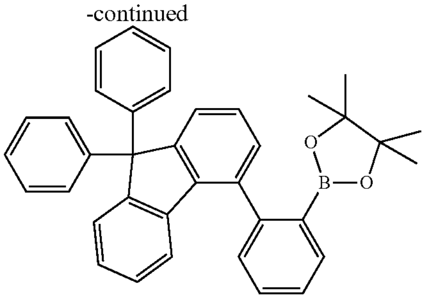

Intermediate E

The intermediate D (6.0 g), bis(pinacolato)diboron (4.5 g), $Pd_2(dba)_3$ (0.21 g), XPhos (0.45 g), and potassium acetate (2.8 g) were added to 1,4-dioxane (5100 mL), and argon gas was injected into the suspension for 5 minutes. The mixture was heated at 90° C. for 18 hours with stirring under an argon atmosphere. The solvent was distilled off from the reaction solution, toluene and water were added thereto, and the organic phase was taken. The organic phase was concentrated and the resulting residue was subjected to column chromatography to obtain an intermediate E (4.3 g. yield 71%).

(2-3) Synthesis of Compound Inv-2

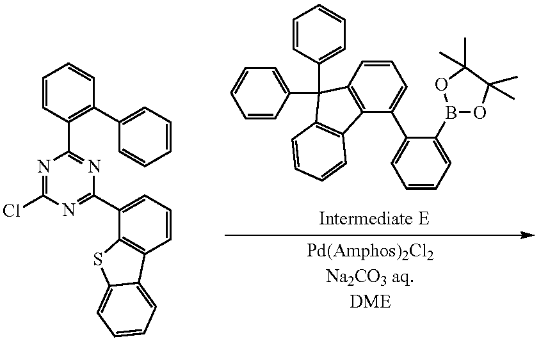

Intermediate B

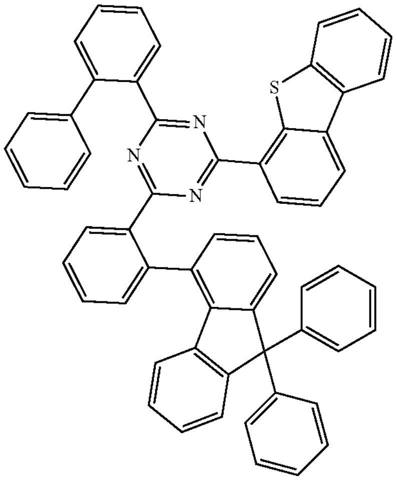

Inv-2

The intermediate B (4.0 g) and the intermediate E (5.1 g) were added to 1,2-dimethoxyethane (DME) (150 mL), and argon gas was injected into the solution for 5 minutes. Pd(Amphos)$_2$Cl$_2$ (0.3 g) and an aqueous sodium carbonate solution (2 M, 15 mL) were added thereto, and the mixture was heated at 90° C. for 8 hours with stirring under an argon atmosphere. The solvent was distilled off from the reaction solution, and the resulting solid was subjected to column chromatography to obtain Inv-2 (4.1 g. yield 57%).

Mass spectrometry gave a result of m/e=808, which confirmed that the product was the target compound.

Synthetic Example 3: Synthesis of Compound Inv-3

(3-1) Synthesis of Intermediate F

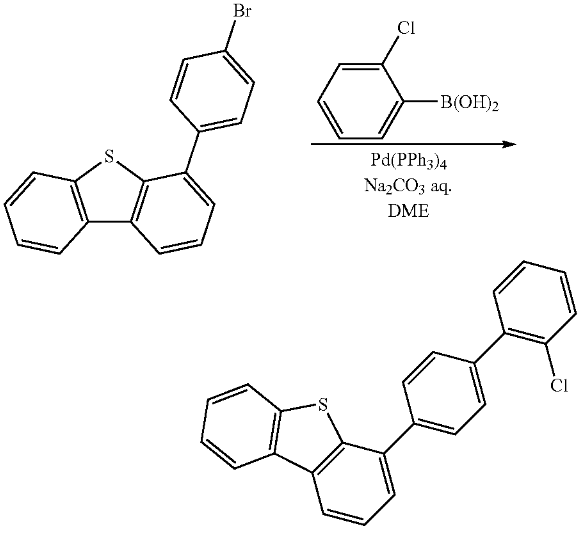

Intermediate F

An intermediate F was obtained as a white solid (16.2 g, yield 98%) by using 4-(p-bromophenyl)dibenzo[b,d]thiophene (15.0 g) under the same conditions as described in Synthetic Example 2 (2-1).

(3-2) Synthesis of Intermediate G

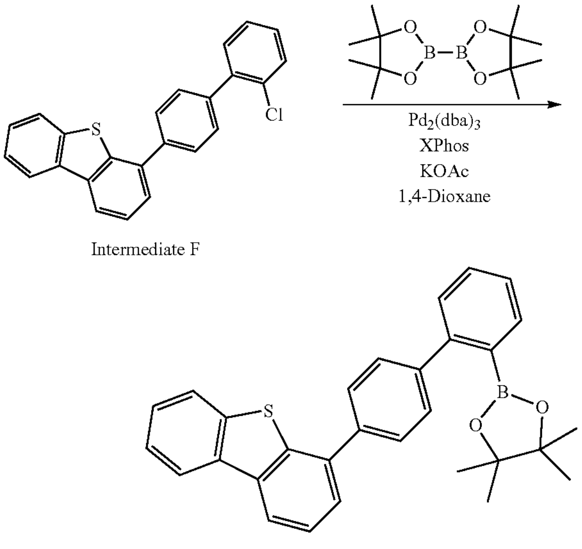

Intermediate F

Intermediate G

An intermediate G was obtained as a white solid (10.0 g; yield 72%) by using the intermediate F (11.1 g) under the same conditions as described in Synthetic Example 2 (2-2).

(3-3) Synthesis of Inv-3

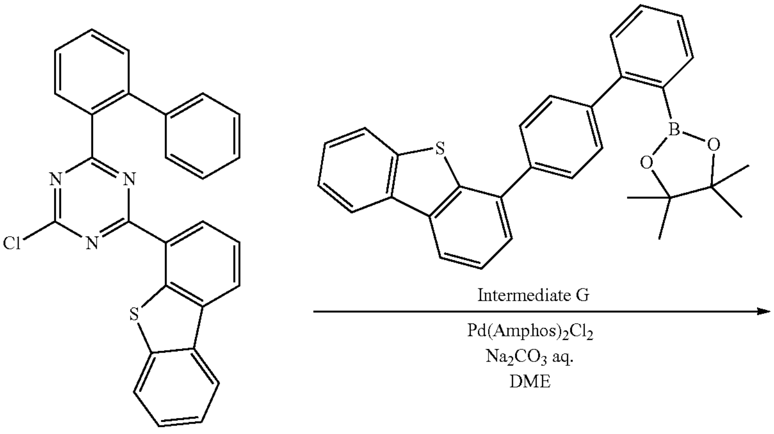

Intermediate B

-continued

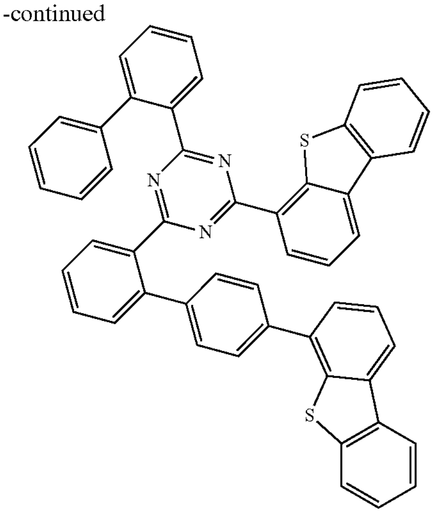

Inv-3

Inv-3 was obtained as a white solid (2.8 g, yield 55%) by using the intermediate B (3.0 g) and the intermediate G (4.0 g) under the same conditions as described in Synthetic Example 2 (2-3).

Mass spectrometry gave a result of m/e=749, which confirmed that the product was the target compound.

Synthetic Example 4: Synthesis of Compound Inv-4

(4-1) Synthesis of Intermediate H

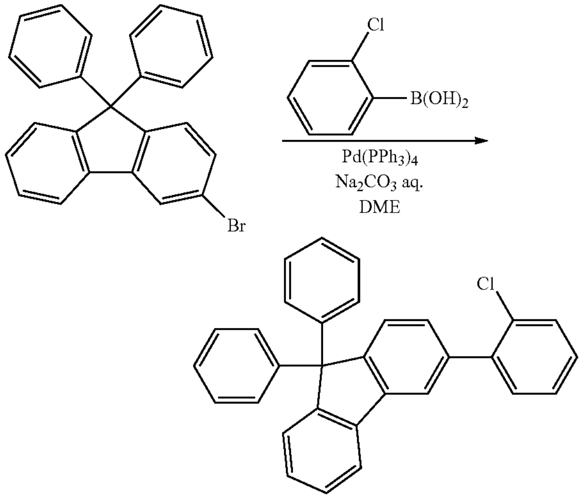

Intermediate H

An intermediate H was obtained as a white solid (3.9 g, yield 98%) by using 3-bromo-9,9-diphenylfluorene (3.7 g) under the same conditions as described in Synthetic Example 2 (2-1).

(4-2) Synthesis of Intermediate I

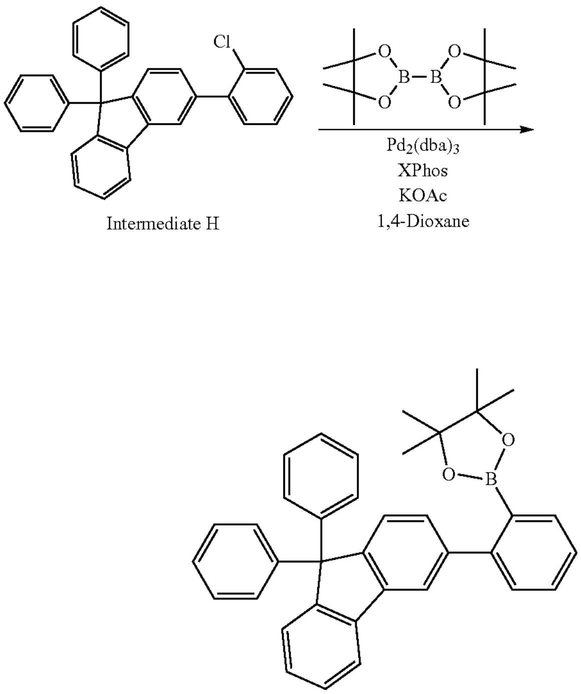

Intermediate I

An intermediate I was obtained as a white solid (3.4 g, yield 63%) by using the intermediate H (3.9 g) under the same conditions as described in Synthetic Example 2 (2-2).

(4-3) Synthesis of Inv-4

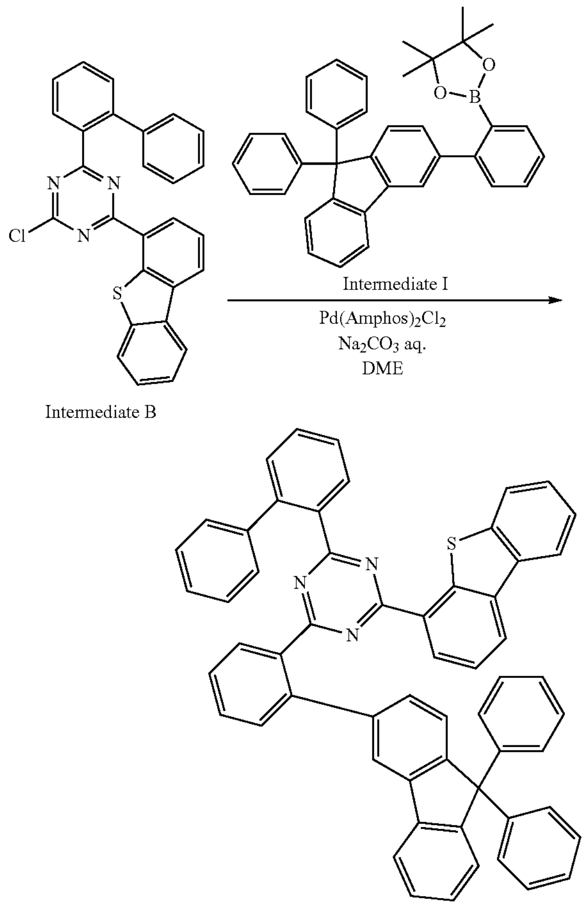

Intermediate B

Inv-4

Inv-4 was obtained as a white solid (1.8 g, yield 33%) by using the intermediate B (3.0 g) and the intermediate I (4.5 g) under the same conditions as described in Synthetic Example 2 (2-3).

Mass spectrometry gave a result of m/e=808, which confirmed that the product was the target compound.

Synthetic Example 5: Synthesis of Compound Inv-5

(5-1) Synthesis of Intermediate J

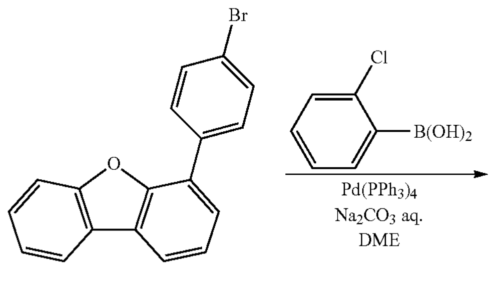

-continued

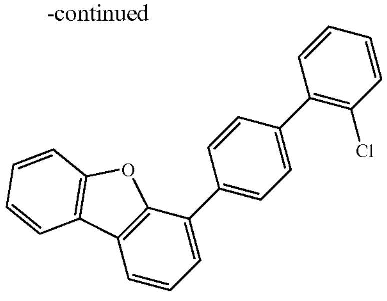

Intermediate J

An intermediate J was obtained as a white solid (9.3 g, yield 85%) using 4-(p-bromophenyl)dibenzo[b,d]furane (10.0 g) under the same conditions as described in Synthetic Example 2 (2-1).

(5-2) Synthesis of Intermediate K

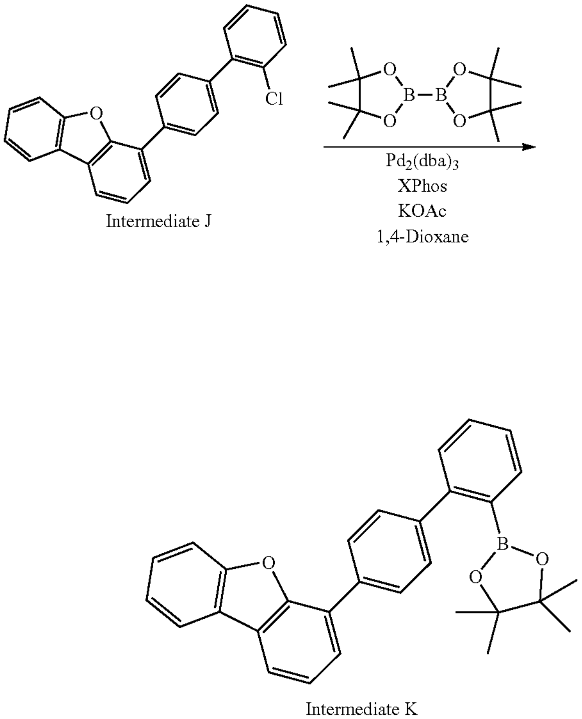

Intermediate J

Intermediate K

An intermediate K was obtained as a white solid (8.8 g, yield 75%) by using the intermediate J (11.1 g) under the same conditions as described in Synthetic Example 2 (2-2).

(5-3) Synthesis of Inv-5

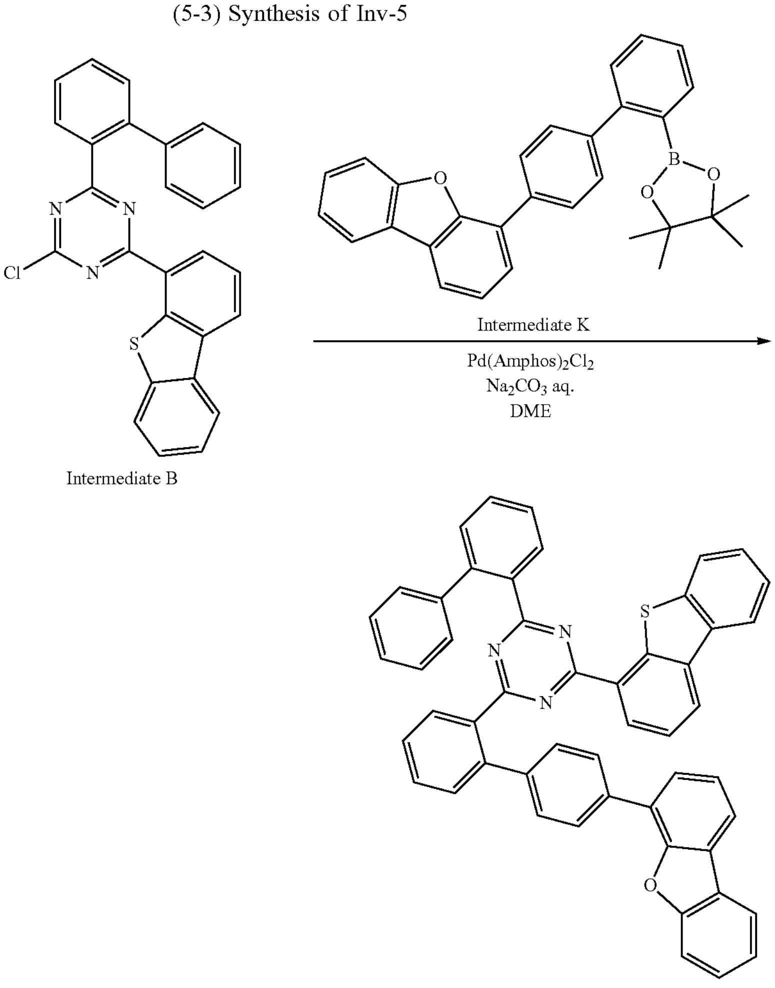

Intermediate B

Inv-5

Inv-5 was obtained as a white solid (3.2 g, yield 66%) by using the intermediate B (3.0 g) and the intermediate K (3.9 g) under the same conditions as described in Synthetic Example 2 (2-3).

Mass spectrometry gave a result of m/e=734, which confirmed that the product was the target compound.

Synthetic Example 6: Synthesis of Compound Inv-6

(6-1) Synthesis of Intermediate L

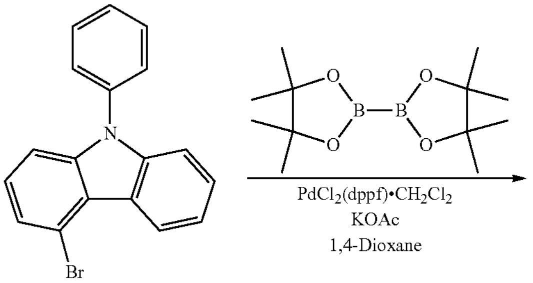

-continued

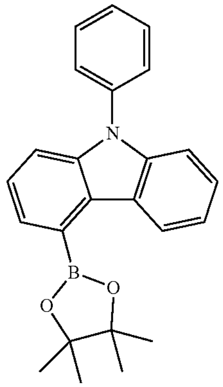

Intermediate L

An intermediate L was obtained as a white solid (9.28 g, yield 81%) under the same conditions as described in Synthetic Example 2 (2-2) except for using 4-bromo-9-phenylcarbazole (10.0 g) and using a $PdCl_2$(dppf) dichloromethane adduct (0.5 g) in place of $Pd_2(dba)_3$ and XPhos.

(6-2) Synthesis of Compound Inv-6

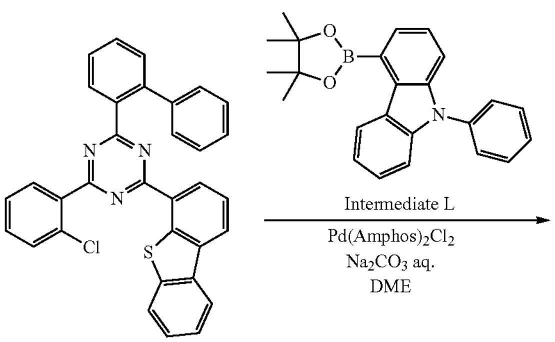

Intermediate C

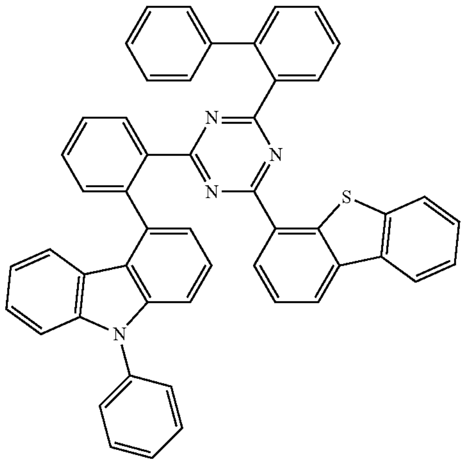

Inv-6

Inv-6 was obtained as a white solid (5.4 g, yield 97%) using the intermediate C (4.0 g) and the intermediate L (3.4 g) under the same conditions as described in Synthetic Example 2 (2-3).

Mass spectrometry gave a result of m/e=733, which confirmed that the product was the target compound.

Synthetic Example 7: Synthesis of Compound Inv-7

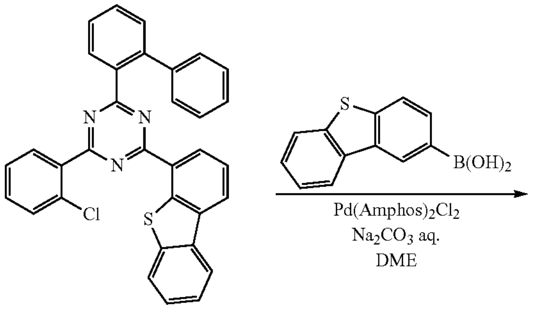

Intermediate C

-continued

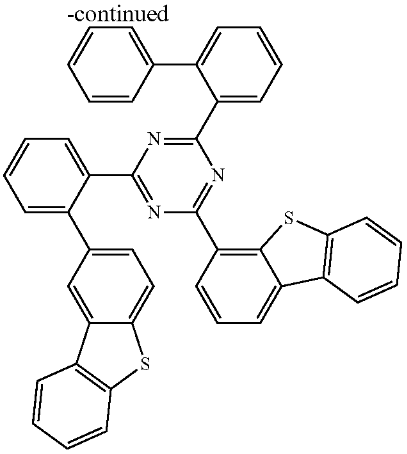

Inv-7

Inv-7 was obtained as a white solid (4.3 g, yield 83%) by using the intermediate C (4.0 g) and dibenzothiophene-2-boronic acid (2.3 g) under the same conditions as described in Synthetic Example 2 (2-3).

Mass spectrometry gave a result of m/e=674, which confirmed that the product was the target compound.

Synthetic Example 8: Synthesis of Compound Inv-8

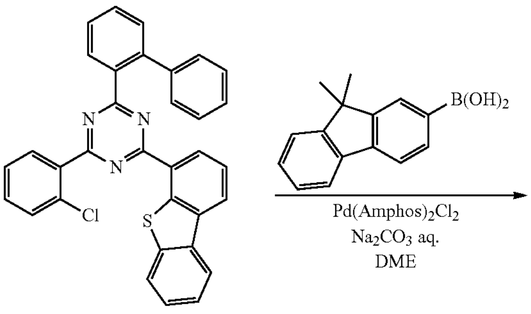

Intermediate C

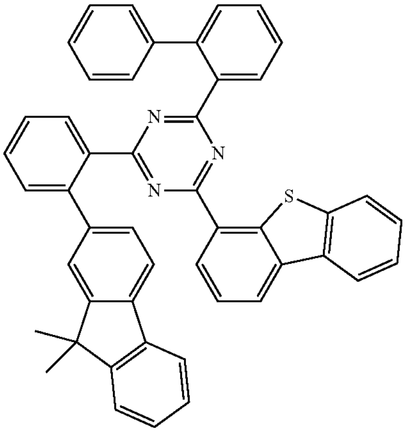

Inv-8

Inv-7 was obtained as a white solid (4.1 g, yield 78%) by using the intermediate C (4.0 g) and 9,9-dimethylfluorene 2-boronic acid (2.4 g) under the same conditions as described in Synthetic Example 2 (2-3).

Mass spectrometry gave a result of m/e=684, which confirmed that the product was the target compound.

Synthetic Example 9: Synthesis of Compound Inv-9

(9-1) Synthesis of Intermediate M

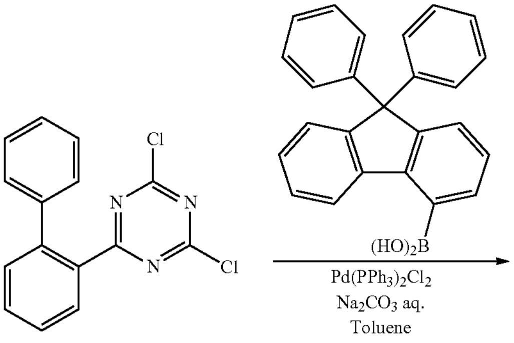

Intermediate A

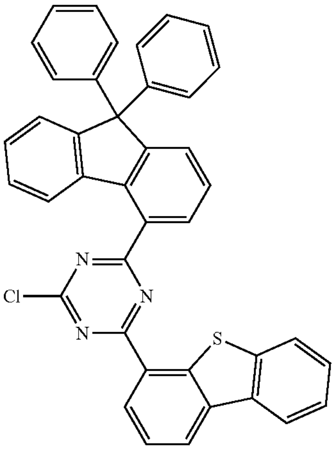

Intermediate M

An intermediate M was obtained as a white solid (3.6 g, yield 32%) by using the intermediate A (6.6 g) and 9,9-diphenylfluorene-4-boronic acid (6.7 g) under the same conditions as described in Synthetic Example 1 (1-2).

(9-2) Synthesis of Intermediate N

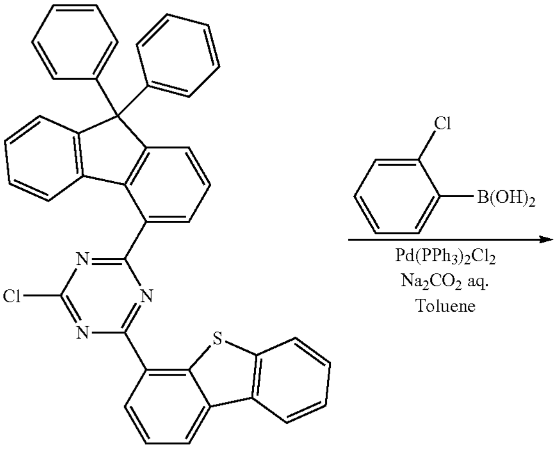

Intermediate M

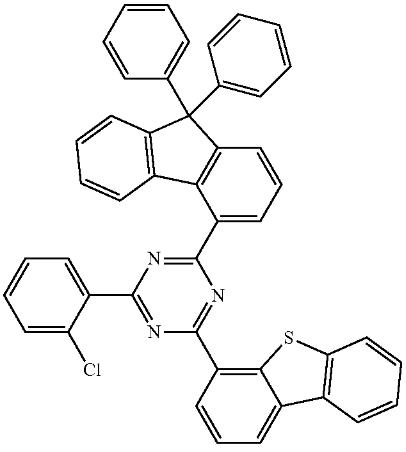

Intermediate N

An intermediate N was obtained as a white solid (3.4 g, yield 84%) by using the intermediate M (3.6 g) and 2-chlorophenyl boronic acid (0.9 g) under the same conditions as described in Synthetic Example 1 (1-3).

(9-3) Synthesis of Compound Inv-9

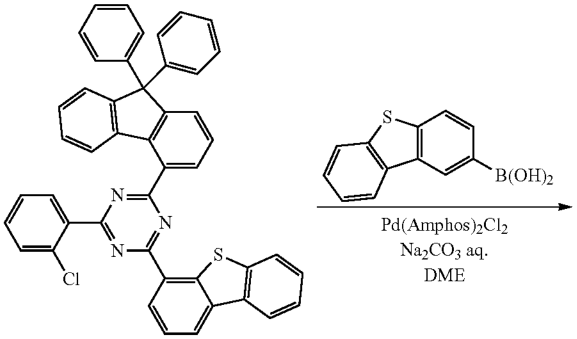

Intermediate N

-continued

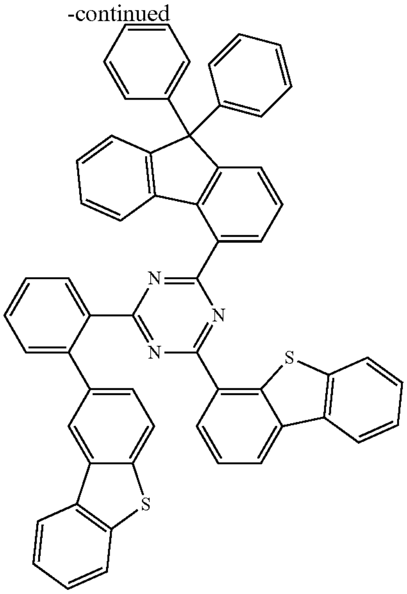

Inv-9

Inv-9 was obtained as a white solid (3.1 g, yield 76%) by using the intermediate N (3.4 g) and the dibenzothiophene-2-boronic acid (1.5 g) under the same conditions as described in Synthetic Example 2 (1-4).

Mass spectrometry gave a result of m/e=838, which confirmed that the product was the target compound.

Synthetic Example 10: Synthesis of Compound Inv-10

Inv-10

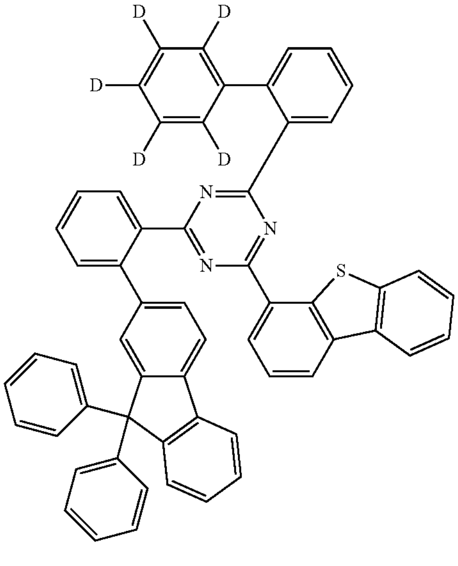

Inv-10 was synthesized by the same synthetic scheme as in Synthetic Example 1 except for using 1,1'-biphenyl-2'-boronic acid (2,3,4,5,6-d) in place of biphenyl-2-boronic acid.

Mass spectrometry gave a result of m/e=812, which confirmed that the product was the target compound.

CITATION LIST

1,11: Organic EL device
2: Substrate
3: Anode
4: Cathode
5: Light emitting layer
6: Hole transport zone (hole transport layer)
6*a*: Hole injection layer
6*b*: First hole transport layer
6*c*: Second hole transport layer
7: Electron transport zone (electron transport layer)
7*a*: First electron transport layer
7*b*: Second electron transport layer
10, 20: Light emitting unit

The invention claimed is:

1. A compound represented by the following formula (1):

(1)

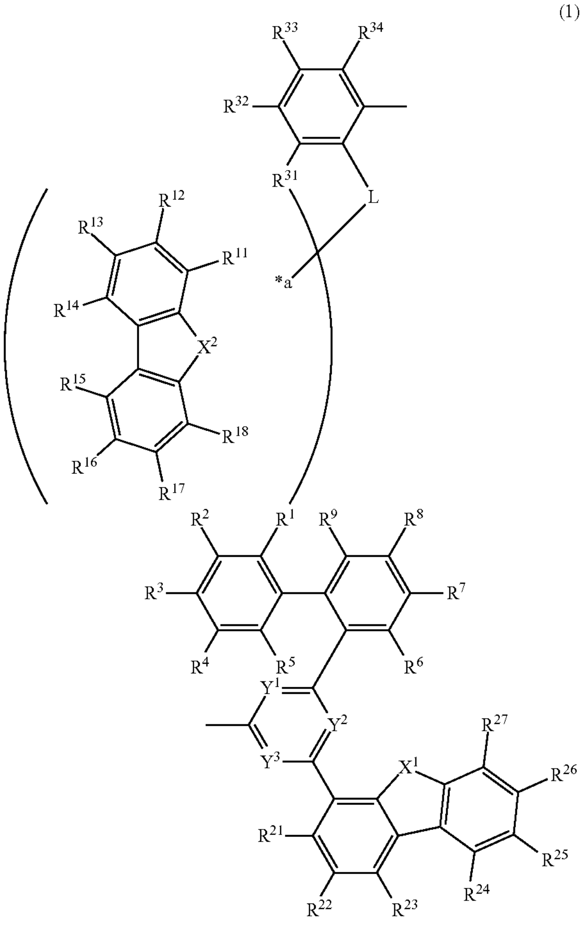

wherein $R^1$ to $R^9$ are each independently selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a cyano group;

provided that, in one or more pairs selected from $R^1$ and $R^2$, $R^2$ and $R^3$, $R^3$ and $R^4$, $R^4$ and $R^5$, $R^6$ and $R^7$, $R^7$ and $R^8$, and $R^8$ and $R^9$, adjacent two may bind to each other to form a substituted or unsubstituted ring structure, or $R^1$ and $R^9$ may bind to each other to form-$CR^aR^b$— that crosslinks two benzene rings;

$R^a$ and $R^b$ are each independently selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a cyano group;

two selected from $Y^1$ to $Y^3$ are a nitrogen atom and the remaining one is CR, or all of $Y^1$ to $Y^3$ are a nitrogen atom;

R is selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a cyano group;

$X^1$ is an oxygen atom or a sulfur atom;

$R^{21}$ to $R^{27}$ are a hydrogen atom;

$R^{31}$ to $R^{34}$ are each independently selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a cyano group;

provided that, in one or more pairs selected from $R^{31}$ and $R^{32}$, $R^{32}$ and $R^{33}$, and $R^{33}$ and $R^{34}$, adjacent two may bind to each other to form a substituted or unsubstituted ring structure;

L is selected from a single bond, a substituted or unsubstituted arylene group having 6 to 50 ring carbon atoms, and a substituted or unsubstituted divalent heterocyclic group having 5 to 30 ring carbon atoms;

one of $R^{11}$ to $R^{14}$ is a single bond binding to *a;

$R^{11}$ to $R^{14}$ that are not a single bond binding to *a and $R^{15}$ to $R^{18}$ are a hydrogen atom;

$X^2$ is selected from an oxygen atom, a sulfur atom, $NR^A$, and $CR^BR^C$;

$R^A$ is selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms;

$R^B$ and $R^C$ are each independently selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, and a cyano group;

provided that, when $R^B$ and $R^C$ are each independently a substituted or unsubstituted aryl group having 6 to 50 ring carbon atoms, the two aryl groups may be crosslinked via —O— or —S—.

2. The compound according to claim 1, wherein the compound is represented by the following formula (1a) or (1b):

(1a)

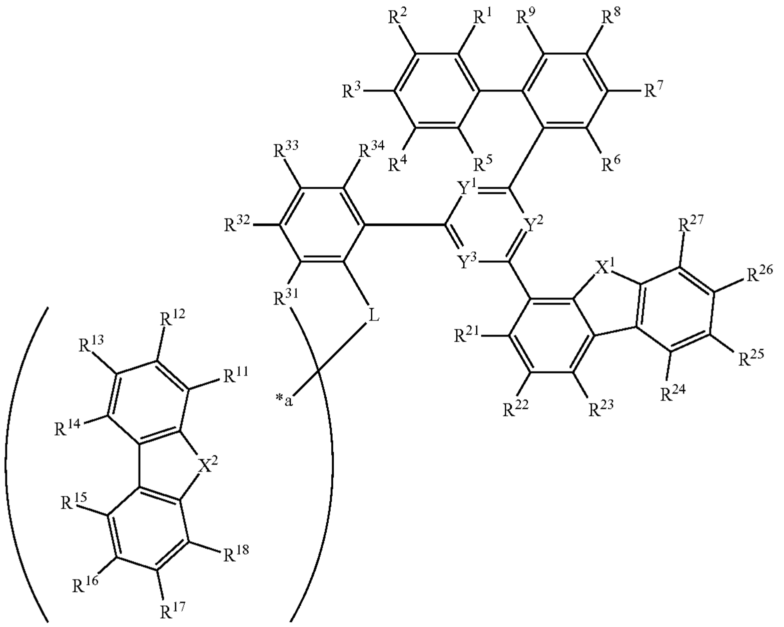

-continued
(1b)
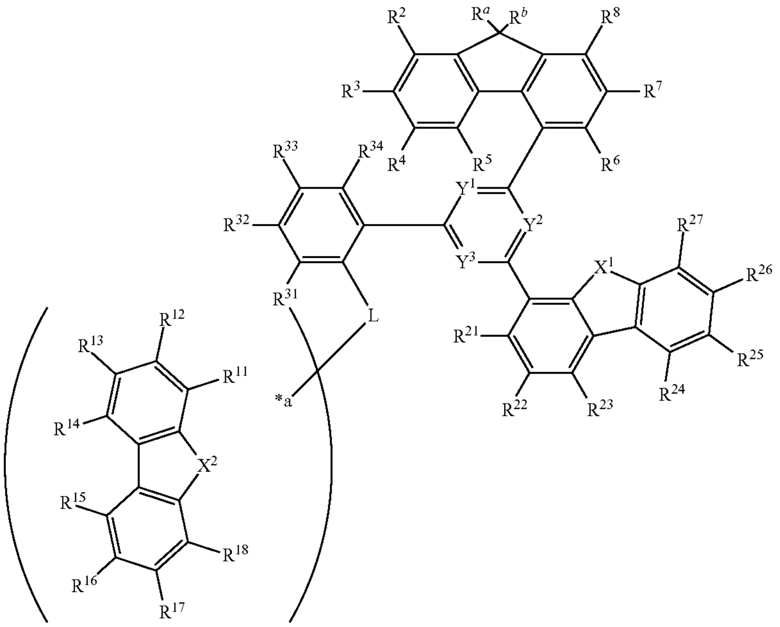
wherein $X^1$, $X^2$, $Y^1$ to $Y^3$, L, *a, $R^a$, $R^b$, $R^1$ to $R^9$, $R^{11}$ to $R^{18}$, $R^{21}$ to $R^{27}$, and $R^{31}$ to $R^{34}$ are as defined for the formula (1), provided that $R^1$ and $R^9$ do not bind to each other.
3. The compound according to claim 1, wherein the compound is represented by any one of the following formulae (2a) to (2d):
(2a)
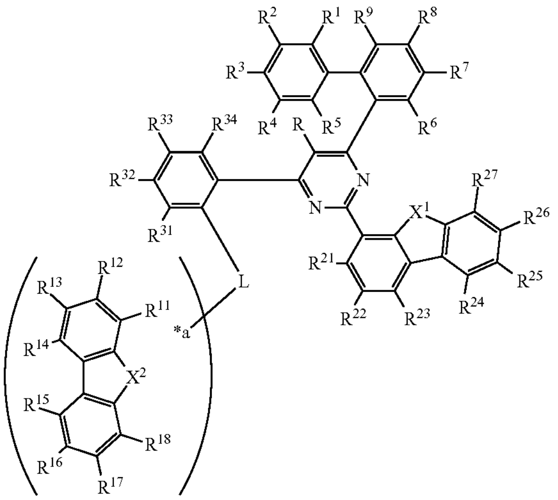
-continued
(2b)
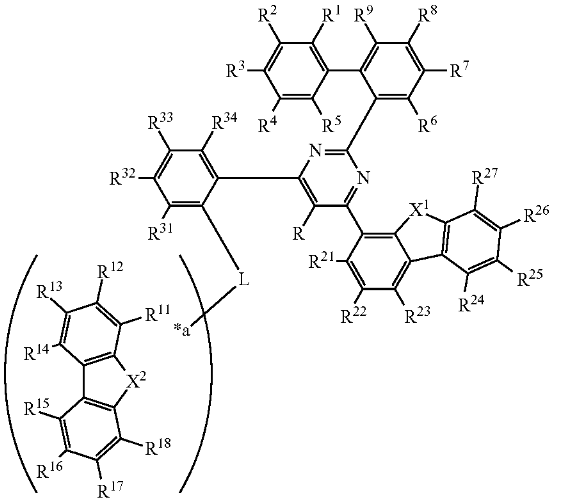

-continued
(2c)
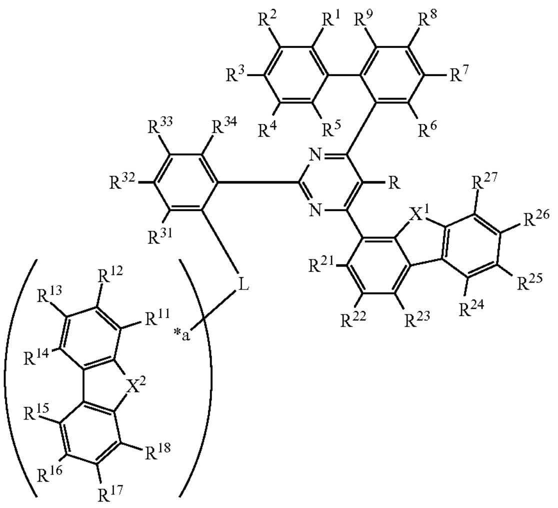
-continued
(2d)
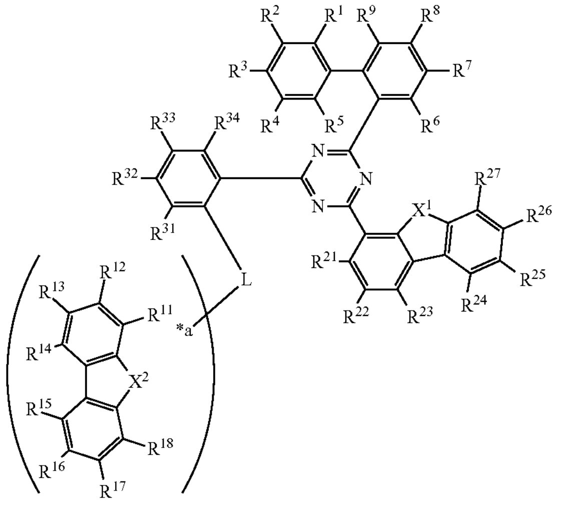
wherein $X^1$, $X^2$, L, *a, R, $R^1$ to $R^9$, $R^{11}$ to $R^{18}$, $R^{21}$ to $R^{27}$, and $R^{31}$ to $R^{34}$ are as defined for the formula (1).
4. The compound according to claim 1, wherein the compound is represented by the following formula (3a) or (3b):
(3a)
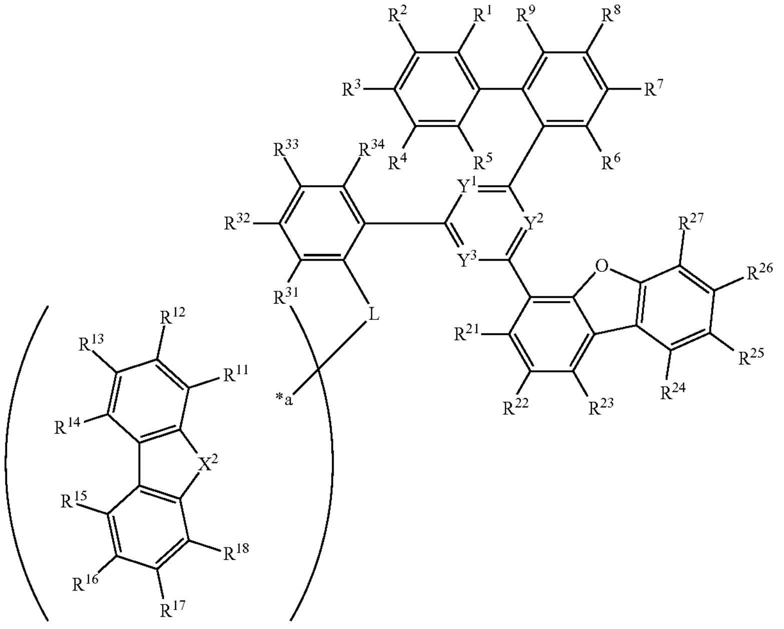

-continued
(3b)
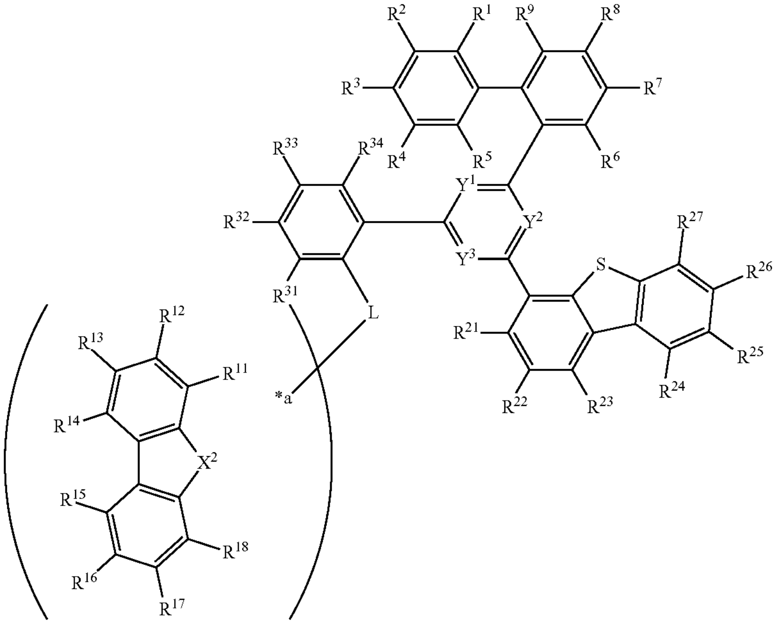
wherein $X^2$, $Y^1$ to $Y^3$, L, *a, $R^1$ to $R^9$, $R^{11}$ to $R^{18}$, $R^{21}$ to $R^{27}$, and $R^{31}$ to $R^{34}$ are as defined for the formula (1).
5. The compound according to claim 1, wherein the compound is represented by the following formula (4a) or (4b):
(4a)
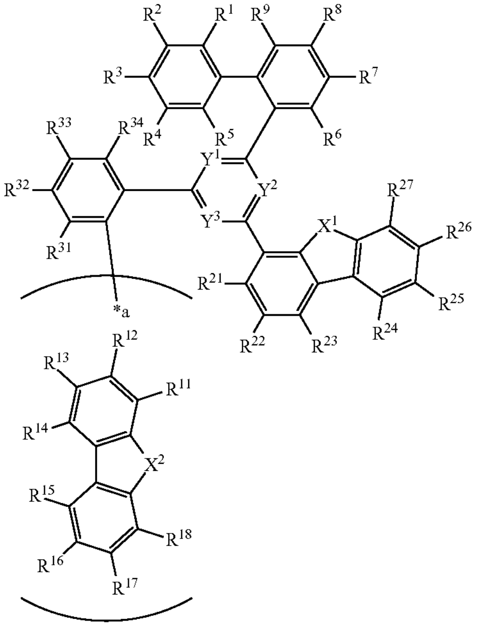

-continued (4b)

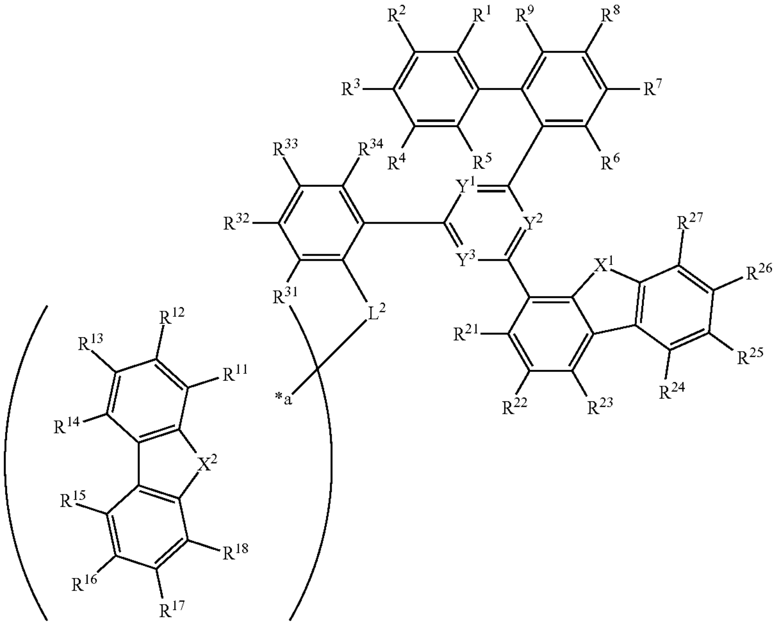

wherein $X^1$, $X^2$, $Y^1$ to $Y^3$, *a, $R^1$ to $R^9$, $R^{11}$ to $R^{18}$, $R^{21}$ to $R^{27}$, and $R^{31}$ to $R^{34}$ are as defined for the formula (1), and $L^2$ is a substituted or unsubstituted arylene group having 6 to 50 ring carbon atoms or a substituted or unsubstituted divalent heterocyclic group having 5 to 30 ring carbon atoms.

6. The compound according to claim 1, wherein the compound is represented by the following formulae (5a) to (5d)

(5a)

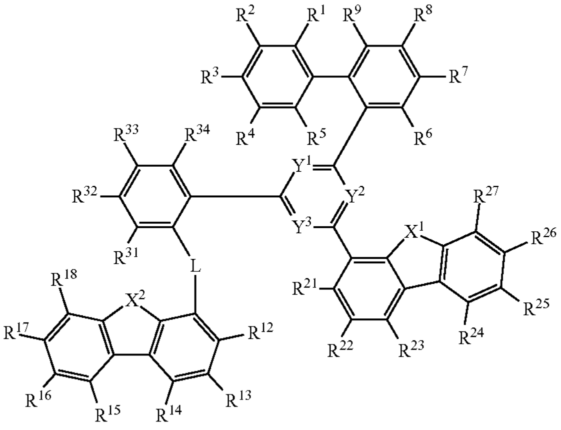

-continued (5b)

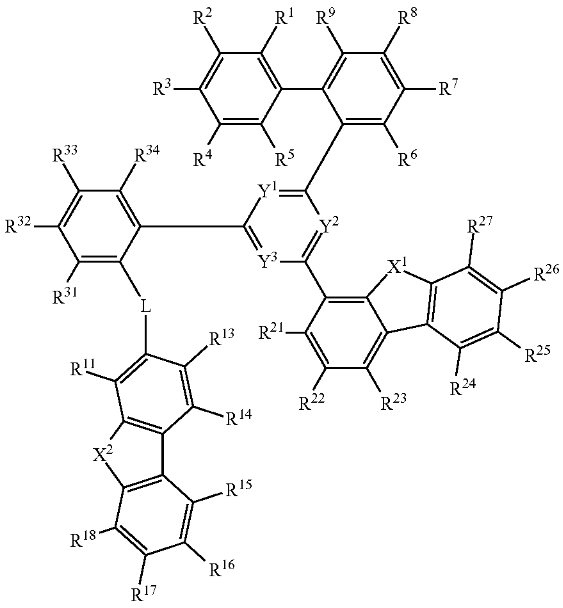

-continued
(5c)
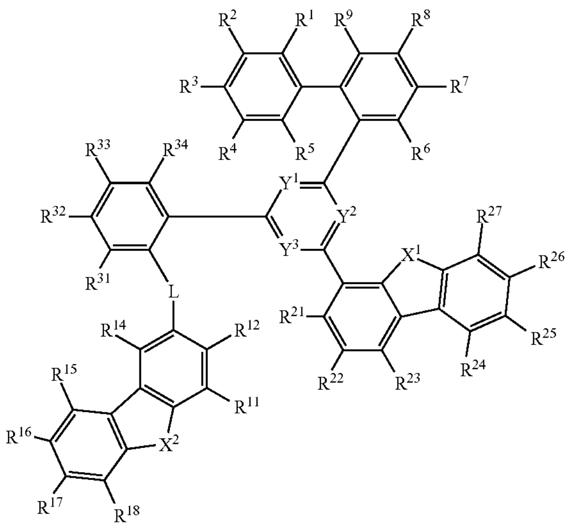
(5d)
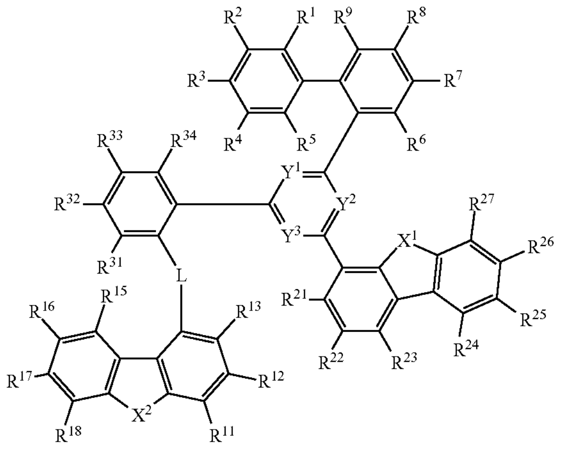
wherein $X^1$, $X^2$, $Y^1$ to $Y^3$, L, $R^1$ to $R^9$, $R^{11}$ to $R^{18}$, $R^{21}$ to $R^{27}$, and $R^{31}$ to $R^{34}$ are as defined for the formula (1).
7. The compound according to claim 1, wherein the compound is represented by any one of the following formulae (6a) to (6d):
(6a)
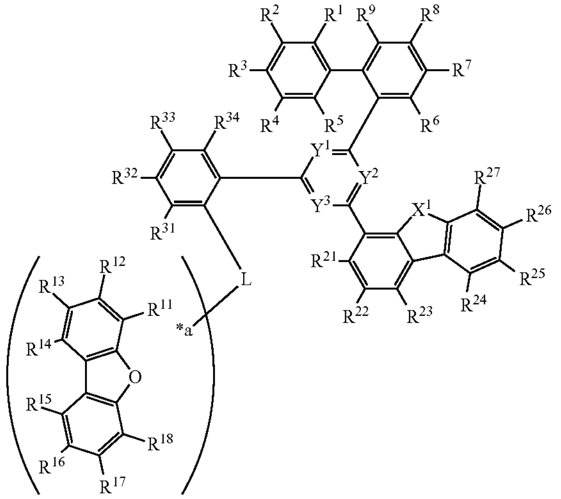
(6b)
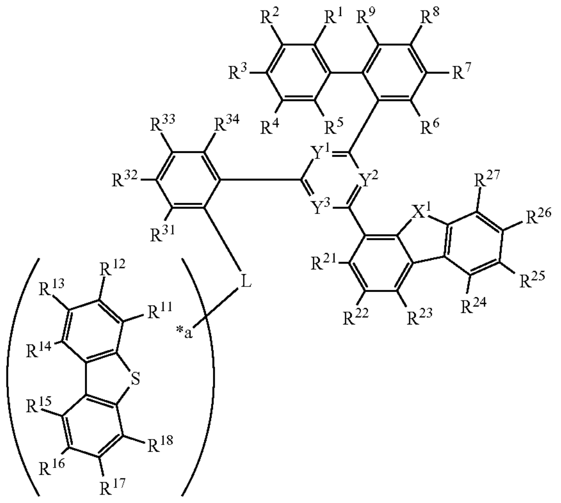
(6c)
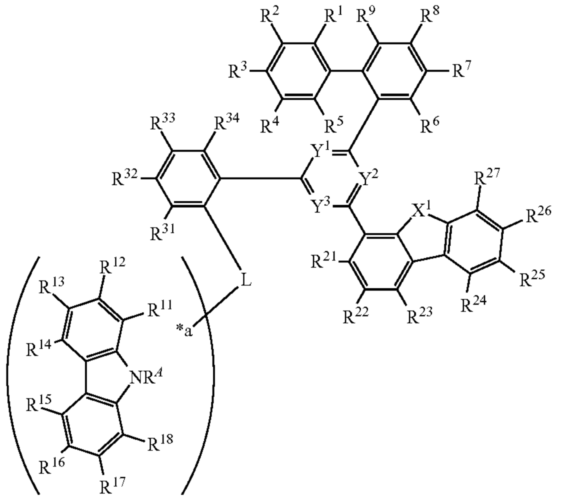

-continued
(6d)
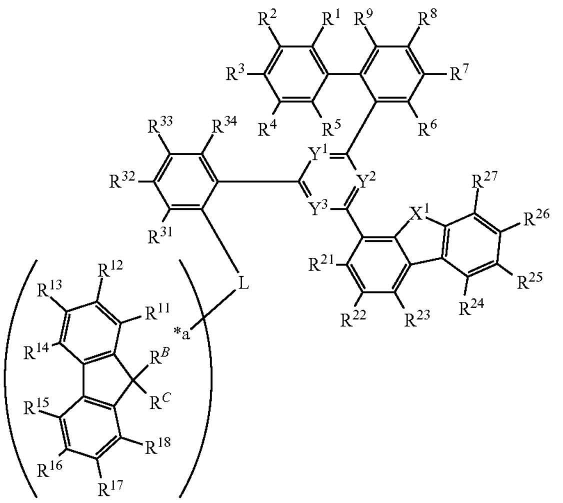
wherein $X^1$, $Y^1$ to $Y^3$, L, *a, $R^1$ to $R^9$, $R^{11}$ to $R^{18}$, $R^{21}$ to $R^{27}$, $R^{31}$ to $R^{34}$, and $R^A$ to $R^C$ are as defined for the formula (1).
8. The compound according to claim 1, wherein the compound is represented by any one of the following formulae (19) to (24):
(19)
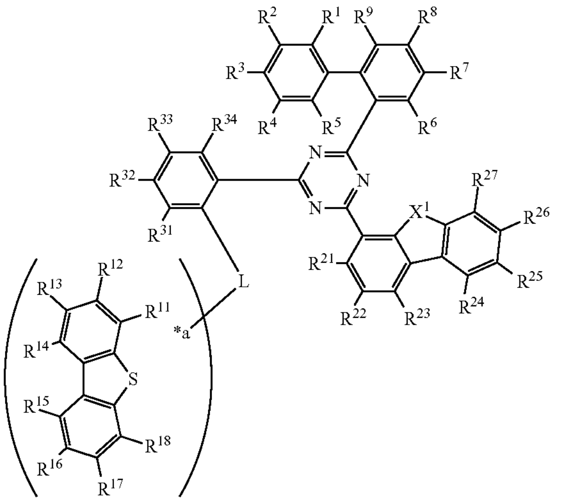
-continued
(20)
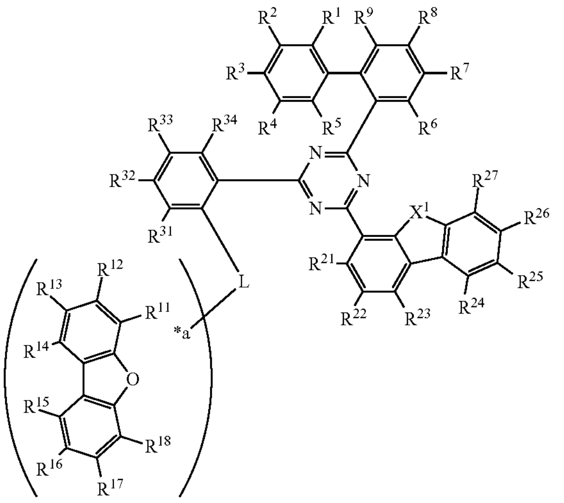
(21)
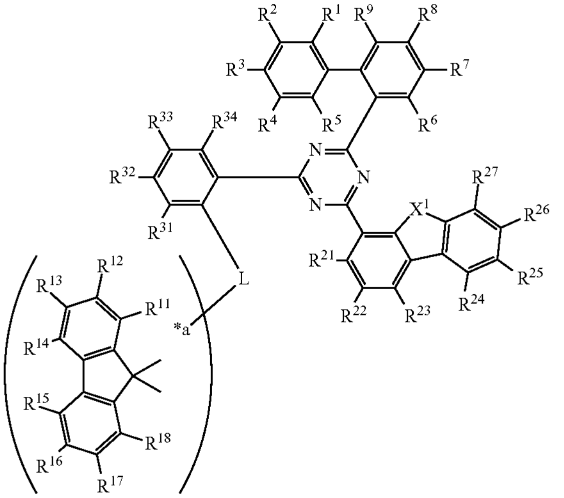
(22)
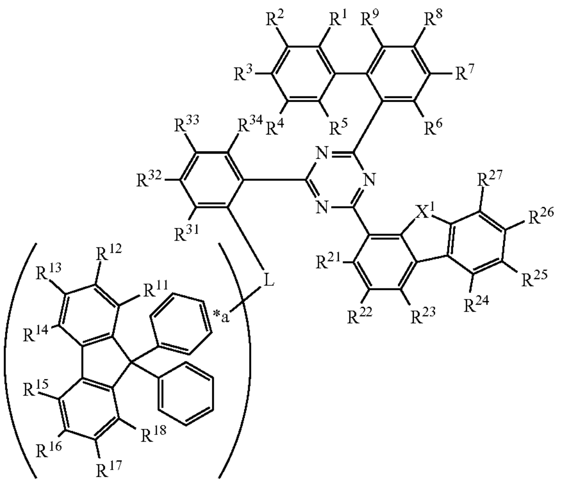

-continued (23)

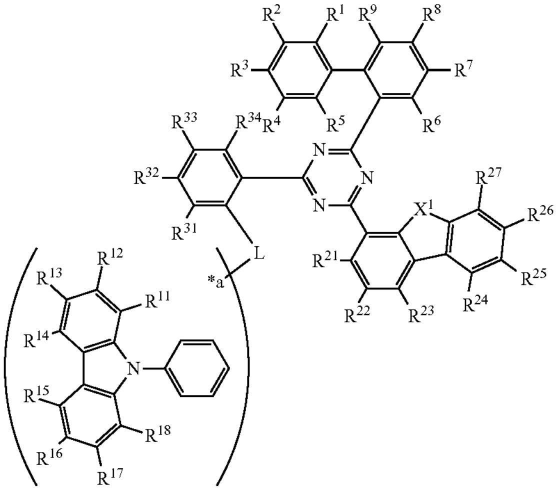

(24)

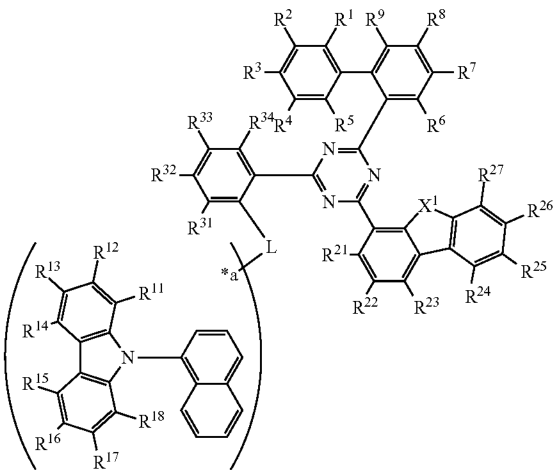

wherein $X^1$, L, *a, $R^1$ to $R^9$, $R^{11}$ to $R^{18}$, $R^{21}$ to $R^{27}$, and $R^{31}$ to $R^{34}$ are as defined for the formula (1).

9. The compound according to claim 1, wherein in the substituted or unsubstituted alkyl group having 1 to 50 carbon atoms represented by R, $R^1$ to $R^9$, $R^a$, $R^b$, $R^A$, $R^B$, and $R^C$, the alkyl group is selected from a methyl group, an ethyl group, an n-propyl group, an isopropyl group, an n-butyl group, an isobutyl group, an s-butyl group, a t-butyl group, and an n-pentyl group.

10. The compound according to claim 1, wherein in the substituted or unsubstituted aryl group having 6 to 50 ring carbon atoms represented by R, $R^1$ to $R^9$, $R^a$, $R^b$, $R^A$, $R^B$, and $R^C$, the aryl group is selected from a phenyl group, a biphenylyl group, a terphenylyl group, a naphthyl group, an anthryl group, a phenanthryl group, a phenalenyl group, a pyrenyl group, a chrysenyl group, a triphenylenyl group, a tetracenyl group, a pentacenyl group, a fluorenyl group, a fluoranthenyl group, a perylenyl group, and a 9,9'-spirobifluorenyl group.

11. The compound according to claim 1, wherein in the substituted or unsubstituted arylene group having 6 to 50 ring carbon atoms represented by L or $L^2$, the arylene group is a divalent group derived from a group selected from a phenyl group, a biphenylyl group, a terphenylyl group, a naphthyl group, a phenanthryl group, a pyrenyl group, a chrysenyl group, a triphenylenyl group, a fluorenyl group, and a 9,9'-spirobifluorenyl group by removing one hydrogen atom on an aromatic hydrocarbon ring.

12. The compound according to claim 1, wherein $R^a$ and $R^b$ are each independently selected from a substituted or unsubstituted alkyl group having 1 to 50 carbon atoms and a substituted or unsubstituted aryl group having 6 to 50 ring carbon atoms.

13. The compound according to claim 1, wherein a structure represented by the formula (10) in the compound:

(10)

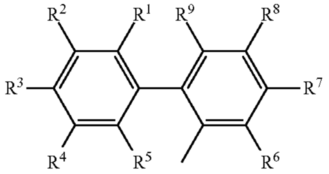

is selected from the following groups

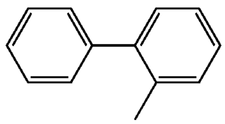

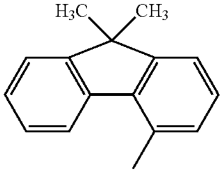

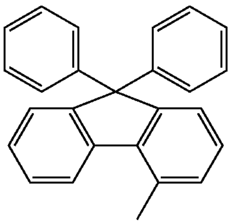

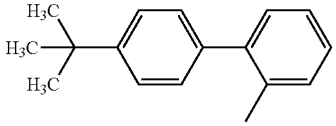

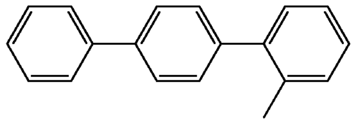

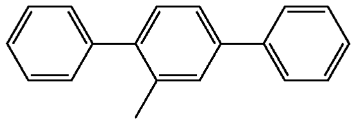

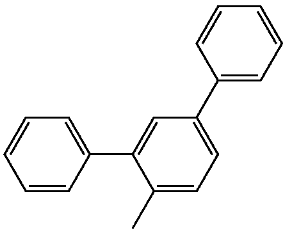

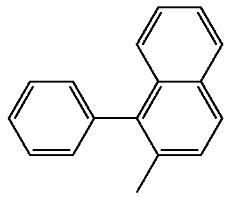

-continued

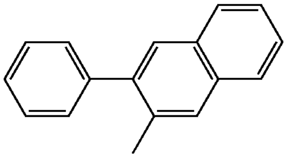

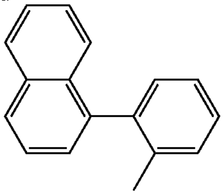

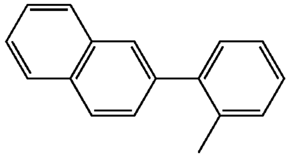
.

14. The compound according to claim 1, wherein $R^B$ and $R^C$ are each independently selected from a substituted or unsubstituted alkyl group having 1 to 50 carbon atoms and a substituted or unsubstituted aryl group having 6 to 50 ring carbon atoms.

15. The compound according to claim 1, wherein the compound represented by the formula (1) comprises at least one deuterium atom.

16. An organic electroluminescent device comprising a cathode, an anode, and an organic layer between the cathode and the anode, wherein the organic layer comprises a light emitting layer, and wherein at least one layer of the organic layer comprises the compound according to claim 1.

17. The organic electroluminescent device according to claim 16, wherein the organic layer comprises an electron transport zone between the light emitting later and the cathode, wherein the electron transport zone comprises the compound, wherein the electron transport zone comprises an electron transport layer, and wherein the electron transport layer comprises the compound.

18. The organic electroluminescent device according to claim 17, wherein the electron transport layer comprises a first electron transport layer on an anode side and a second electron transport layer on a cathode side, and wherein the second electron transport layer comprises the compound.

19. An electronic appliance comprising the organic electroluminescent device according to claim 16.

* * * * *